United States Patent
Thompson et al.

(10) Patent No.: US 11,602,449 B2
(45) Date of Patent: Mar. 14, 2023

(54) SYSTEMS AND METHODS OF PERFORMING SURGERY USING LAPLACE'S LAW TENSION RETRACTION DURING SURGERY

(71) Applicant: Standard Bariatrics, Inc., Cincinnati, OH (US)

(72) Inventors: Jonathan R. Thompson, Cincinnati, OH (US); Mark Steven Ortiz, Milford, OH (US); Saylan James Lukas, Cincinnati, OH (US); Liam Clayton Groom, Cincinnati, OH (US)

(73) Assignee: Standard Bariatrics, Inc., Cincinnati, OH (US)

( * ) Notice: Subject to any disclaimer, the term of this patent is extended or adjusted under 35 U.S.C. 154(b) by 0 days.

(21) Appl. No.: 17/089,619

(22) Filed: Nov. 4, 2020

(65) Prior Publication Data

US 2021/0128335 A1 May 6, 2021

Related U.S. Application Data

(60) Provisional application No. 62/930,254, filed on Nov. 4, 2019.

(51) Int. Cl.
*A61F 5/00* (2006.01)

(52) U.S. Cl.
CPC ............ *A61F 5/0086* (2013.01); *A61F 5/005* (2013.01)

(58) Field of Classification Search
CPC ................................ A61F 5/005; A61F 5/0086
See application file for complete search history.

(56) References Cited

U.S. PATENT DOCUMENTS

| 848,126 A | 3/1907 | Roosevelt |
| 1,413,896 A | 4/1922 | Brix |
| (Continued) | | |

FOREIGN PATENT DOCUMENTS

| CA | 2663002 A1 | 10/2009 |
| EP | 140552 A2 | 5/1985 |
| (Continued) | | |

OTHER PUBLICATIONS

AtriCure, Inc.; 510(k) Summary for AtriClip LAA Exclusion System with preloaded Gillinov-Cosgrove Clip; published Jun. 10, 2010; 6 pages.

(Continued)

*Primary Examiner* — Richard G Louis
(74) *Attorney, Agent, or Firm* — Ulmer & Berne LLP; Vance V. VanDrake, III

(57) ABSTRACT

Disclosed are embodiments of an apparatus and system for performing a sleeve gastrectomy. The apparatus can include a bougie for insertion into an interior of a stomach, the bougie having a proximal bougie end and a distal bougie end, an inflation lumen having a proximal lumen end and a distal lumen end, the inflation lumen extending from the proximal bougie end through the distal bougie end, a fluid delivery system coupled with the proximal lumen end, the fluid delivery system being operably configured to deliver positive pressure in a predetermined positive pressure range into the stomach, and a monitor coupled with the proximal lumen end operably configured for the monitoring of pressure or volume within the stomach. The bougie can be operably configured to define a resection line for the sleeve gastrectomy when the predetermined positive pressure range is achieved within the stomach

27 Claims, 30 Drawing Sheets

(56) References Cited

U.S. PATENT DOCUMENTS

| | | | |
|---|---|---|---|
| 2,659,371 | A | 11/1953 | Schnee |
| 2,686,520 | A | 8/1954 | Jarvis et al. |
| 3,017,637 | A | 1/1962 | Sampson |
| 3,490,675 | A | 1/1970 | Green et al. |
| 3,551,987 | A | 1/1971 | Wilkinson |
| 3,877,434 | A | 4/1975 | Ferguson |
| 4,216,891 | A | 8/1980 | Behlke |
| 4,269,190 | A | 5/1981 | Behney |
| 4,319,576 | A | 3/1982 | Rothfuss |
| 4,354,628 | A | 10/1982 | Green |
| 4,442,964 | A | 4/1984 | Becht |
| 4,458,681 | A | 7/1984 | Hopkins |
| 4,494,057 | A | 1/1985 | Hotta |
| 4,520,817 | A | 6/1985 | Green |
| 4,527,724 | A | 7/1985 | Chow et al. |
| 4,558,699 | A | 12/1985 | Bashour |
| 4,605,001 | A | 8/1986 | Rothfuss et al. |
| 4,605,004 | A | 8/1986 | Di Giovanni et al. |
| 4,608,981 | A | 9/1986 | Rothfuss et al. |
| 4,610,383 | A | 9/1986 | Rothfuss et al. |
| 4,617,928 | A | 10/1986 | Alfranca |
| 4,632,290 | A | 12/1986 | Green et al. |
| 4,633,861 | A | 1/1987 | Chow et al. |
| 4,676,774 | A | 6/1987 | Semm et al. |
| 4,679,557 | A | 7/1987 | Opie et al. |
| 4,705,038 | A | 11/1987 | Sjostrom et al. |
| 4,784,137 | A | 11/1988 | Kulik et al. |
| 4,803,985 | A | 2/1989 | Hill |
| 4,819,853 | A | 4/1989 | Green |
| 4,848,637 | A | 7/1989 | Pruitt |
| 4,930,503 | A | 6/1990 | Pruitt |
| 4,935,006 | A * | 6/1990 | Hasson .............. A61M 1/85 604/268 |
| 4,941,623 | A | 7/1990 | Pruitt |
| 4,951,861 | A | 8/1990 | Schulze et al. |
| 4,976,721 | A | 12/1990 | Blasnik et al. |
| 4,978,049 | A | 12/1990 | Green |
| 5,040,715 | A | 8/1991 | Green et al. |
| 5,136,220 | A | 8/1992 | Philipp |
| 5,152,744 | A | 10/1992 | Krause et al. |
| 5,176,651 | A | 1/1993 | Allgood et al. |
| 5,205,459 | A | 4/1993 | Brinkerhoff et al. |
| 5,219,111 | A | 6/1993 | Bilotti et al. |
| 5,221,036 | A | 6/1993 | Takase |
| 5,222,961 | A | 6/1993 | Nakao et al. |
| 5,258,009 | A | 11/1993 | Conners |
| 5,295,977 | A | 3/1994 | Cohen |
| 5,307,976 | A | 5/1994 | Olson et al. |
| 5,308,576 | A | 5/1994 | Green et al. |
| 5,312,410 | A | 5/1994 | Miller et al. |
| 5,327,914 | A | 7/1994 | Shlain |
| 5,333,772 | A | 8/1994 | Rothfuss et al. |
| 5,345,949 | A | 9/1994 | Shlain |
| 5,389,098 | A | 2/1995 | Tsuruta et al. |
| 5,395,030 | A | 3/1995 | Kuramoto et al. |
| 5,395,034 | A | 3/1995 | Allen et al. |
| 5,413,267 | A | 5/1995 | Solyntjes et al. |
| 5,415,334 | A | 5/1995 | Williamson et al. |
| 5,431,323 | A | 7/1995 | Smith et al. |
| 5,443,475 | A | 8/1995 | Auerbach et al. |
| 5,452,836 | A | 9/1995 | Huitema et al. |
| 5,452,837 | A | 9/1995 | Williamson et al. |
| 5,456,401 | A | 10/1995 | Green et al. |
| 5,465,895 | A | 11/1995 | Knodel et al. |
| 5,465,896 | A | 11/1995 | Allen et al. |
| 5,469,840 | A | 11/1995 | Tanii et al. |
| 5,470,006 | A | 11/1995 | Rodak |
| 5,470,009 | A | 11/1995 | Rodak |
| 5,480,089 | A | 1/1996 | Blewett |
| 5,485,952 | A | 1/1996 | Fontayne |
| 5,487,500 | A | 1/1996 | Knodel et al. |
| 5,496,333 | A | 3/1996 | Sackier et al. |
| 5,503,638 | A | 4/1996 | Cooper et al. |
| 5,507,426 | A | 4/1996 | Young et al. |
| 5,507,773 | A | 4/1996 | Huitema et al. |
| 5,514,098 | A | 5/1996 | Pfoslgraf et al. |
| 5,531,744 | A | 7/1996 | Nardella et al. |
| 5,549,621 | A | 8/1996 | Bessler et al. |
| 5,551,622 | A | 9/1996 | Yoon |
| 5,554,169 | A | 9/1996 | Green et al. |
| 5,560,530 | A | 10/1996 | Bolanos et al. |
| 5,562,702 | A | 10/1996 | Huitema et al. |
| 5,571,116 | A | 11/1996 | Bolanos et al. |
| 5,571,131 | A | 11/1996 | Ek et al. |
| 5,586,711 | A | 12/1996 | Plyley et al. |
| 5,597,107 | A | 1/1997 | Knodel et al. |
| 5,630,540 | A | 5/1997 | Blewett |
| 5,632,432 | A | 5/1997 | Schulze et al. |
| 5,636,780 | A | 6/1997 | Green et al. |
| 5,655,698 | A | 8/1997 | Yoon |
| 5,662,667 | A | 9/1997 | Knodel |
| 5,676,674 | A | 10/1997 | Bolanos et al. |
| 5,689,159 | A | 11/1997 | Culp et al. |
| 5,697,542 | A | 12/1997 | Knodel et al. |
| 5,702,409 | A | 12/1997 | Rayburn et al. |
| 5,704,534 | A | 1/1998 | Huitema et al. |
| 5,707,369 | A | 1/1998 | Vaitekunas et al. |
| 5,732,871 | A | 3/1998 | Clark et al. |
| 5,762,256 | A | 6/1998 | Mastri et al. |
| 5,779,130 | A | 7/1998 | Alesi et al. |
| 5,779,132 | A | 7/1998 | Knodel et al. |
| 5,782,396 | A | 7/1998 | Mastri et al. |
| 5,797,538 | A | 8/1998 | Heaton et al. |
| 5,810,240 | A | 9/1998 | Robertson |
| 5,814,055 | A | 9/1998 | Knodel et al. |
| 5,819,240 | A | 10/1998 | Kara |
| 5,820,009 | A | 10/1998 | Melling et al. |
| 5,865,361 | A | 2/1999 | Milliman et al. |
| 5,868,760 | A | 2/1999 | McGuckin, Jr. |
| 5,871,135 | A | 2/1999 | Williamson IV et al. |
| 5,901,895 | A | 5/1999 | Heaton et al. |
| 5,902,312 | A | 5/1999 | Frater et al. |
| 5,954,259 | A | 9/1999 | Viola et al. |
| 5,964,394 | A | 10/1999 | Robertson |
| 5,980,248 | A | 11/1999 | Kusakabe et al. |
| 5,988,479 | A | 11/1999 | Palmer |
| 6,032,849 | A | 3/2000 | Mastri et al. |
| 6,048,330 | A | 4/2000 | Atala |
| 6,099,551 | A | 8/2000 | Gabbay |
| 6,264,087 | B1 | 7/2001 | Whitman |
| 6,270,507 | B1 | 8/2001 | Callicrate |
| 6,315,184 | B1 | 11/2001 | Whitman |
| 6,325,810 | B1 | 12/2001 | Hamilton et al. |
| 6,345,754 | B1 | 2/2002 | Jeng |
| 6,439,541 | B1 | 8/2002 | Nosel et al. |
| 6,488,196 | B1 | 12/2002 | Fenton |
| 6,505,768 | B2 | 1/2003 | Whitman |
| 6,511,490 | B2 | 1/2003 | Robert |
| 6,616,446 | B1 | 9/2003 | Schmid |
| 6,716,233 | B1 | 4/2004 | Whitman |
| 6,769,590 | B2 | 8/2004 | Vresh et al. |
| 6,793,652 | B1 | 9/2004 | Whitman et al. |
| 6,835,199 | B2 | 12/2004 | McGuckin et al. |
| RE38,708 | E | 3/2005 | Bolanos et al. |
| 6,953,138 | B1 | 10/2005 | Dworak et al. |
| 6,978,921 | B2 | 12/2005 | Shelton, IV et al. |
| 6,986,451 | B1 | 1/2006 | Mastri et al. |
| 6,988,649 | B2 | 1/2006 | Shelton, IV et al. |
| 7,025,791 | B2 | 4/2006 | Levine et al. |
| 7,032,799 | B2 | 4/2006 | Viola et al. |
| 7,037,344 | B2 | 5/2006 | Kagan et al. |
| 7,044,353 | B2 | 5/2006 | Mastri et al. |
| 7,070,083 | B2 | 7/2006 | Jankowski |
| 7,128,253 | B2 | 10/2006 | Mastri et al. |
| 7,134,587 | B2 | 11/2006 | Schwemberger et al. |
| 7,175,648 | B2 | 2/2007 | Nakao |
| 7,207,472 | B2 | 4/2007 | Wukusick et al. |
| 7,225,964 | B2 | 6/2007 | Mastri et al. |
| 7,229,428 | B2 | 6/2007 | Gannoe et al. |
| 7,235,089 | B1 | 6/2007 | McGuckin, Jr. |
| 7,258,262 | B2 | 8/2007 | Mastri et al. |
| 7,278,562 | B2 | 10/2007 | Mastri et al. |
| 7,278,563 | B1 | 10/2007 | Green |
| 7,288,100 | B2 | 10/2007 | Molina Trigueros |

(56) References Cited

U.S. PATENT DOCUMENTS

| | | | |
|---|---|---|---|
| 7,308,998 B2 | 12/2007 | Mastri et al. | |
| RE40,237 E | 4/2008 | Bilotti et al. | |
| 7,398,908 B2 | 7/2008 | Holsten et al. | |
| 7,401,721 B2 | 7/2008 | Holsten et al. | |
| 7,404,508 B2 | 7/2008 | Smith et al. | |
| 7,407,075 B2 | 8/2008 | Holsten et al. | |
| 7,407,076 B2 | 8/2008 | Racenet et al. | |
| 7,422,138 B2 | 9/2008 | Bilotti et al. | |
| 7,434,716 B2 | 10/2008 | Viola | |
| 7,434,717 B2 | 10/2008 | Shelton, IV et al. | |
| 7,438,209 B1 | 10/2008 | Hess et al. | |
| 7,455,676 B2 | 11/2008 | Holsten et al. | |
| 7,467,740 B2 | 12/2008 | Shelton, IV et al. | |
| 7,472,815 B2 | 1/2009 | Shelton, IV et al. | |
| 7,481,349 B2 | 1/2009 | Holsten et al. | |
| 7,500,979 B2 | 3/2009 | Hueil et al. | |
| 7,506,791 B2 | 3/2009 | Omaits et al. | |
| 7,510,107 B2 | 3/2009 | Timm et al. | |
| 7,549,564 B2 | 6/2009 | Boudreaux | |
| 7,549,654 B2 | 6/2009 | Anderson et al. | |
| 7,565,993 B2 | 7/2009 | Milliman et al. | |
| 7,588,175 B2 | 9/2009 | Timm et al. | |
| 7,588,176 B2 | 9/2009 | Timm et al. | |
| 7,588,177 B2 | 9/2009 | Racenet | |
| 7,604,151 B2 | 10/2009 | Hess et al. | |
| 7,617,961 B2 | 11/2009 | Viola | |
| 7,635,074 B2 | 12/2009 | Olson et al. | |
| 7,641,091 B2 | 1/2010 | Olson et al. | |
| 7,645,285 B2 | 1/2010 | Cosgrove et al. | |
| 7,658,312 B2 | 2/2010 | Vidal et al. | |
| 7,665,647 B2 | 2/2010 | Shelton, IV et al. | |
| 7,669,746 B2 | 3/2010 | Shelton, IV | |
| 7,669,747 B2 | 3/2010 | Weisenburgh, II et al. | |
| 7,673,781 B2 | 3/2010 | Swayze et al. | |
| 7,673,782 B2 | 3/2010 | Hess et al. | |
| 7,690,547 B2 | 4/2010 | Racenet et al. | |
| 7,694,864 B2 | 4/2010 | Okada et al. | |
| 7,704,264 B2 | 4/2010 | Ewers et al. | |
| 7,708,684 B2 | 5/2010 | Demarais et al. | |
| 7,717,312 B2 | 5/2010 | Beetel | |
| 7,726,537 B2 | 6/2010 | Olson et al. | |
| 7,726,538 B2 | 6/2010 | Holsten et al. | |
| 7,726,539 B2 | 6/2010 | Holsten et al. | |
| 7,731,072 B2 | 6/2010 | Timm et al. | |
| 7,735,703 B2 | 6/2010 | Morgan et al. | |
| 7,744,613 B2 | 6/2010 | Ewers et al. | |
| 7,758,493 B2 | 7/2010 | Gingras | |
| 7,770,774 B2 | 8/2010 | Mastri et al. | |
| 7,775,967 B2 | 8/2010 | Gertner | |
| D624,182 S | 9/2010 | Thouement | |
| 7,793,812 B2 | 9/2010 | Moore et al. | |
| 7,794,475 B2 | 9/2010 | Hess et al. | |
| 7,815,092 B2 | 10/2010 | Whitman et al. | |
| 7,819,896 B2 | 10/2010 | Racenet | |
| 7,828,188 B2 | 11/2010 | Jankowski | |
| 7,837,079 B2 | 11/2010 | Holsten et al. | |
| 7,846,149 B2 | 12/2010 | Jankowski | |
| 7,857,184 B2 | 12/2010 | Viola | |
| 7,866,525 B2 | 1/2011 | Scirica | |
| 7,866,528 B2 | 1/2011 | Olson et al. | |
| 7,871,416 B2 | 1/2011 | Phillips | |
| 7,891,531 B1 | 2/2011 | Ward | |
| 7,891,533 B2 | 2/2011 | Green et al. | |
| 7,913,893 B2 | 3/2011 | Mastri et al. | |
| 7,918,869 B2 | 4/2011 | Saadat et al. | |
| 7,934,630 B2 | 5/2011 | Shelton, IV et al. | |
| 7,955,340 B2 | 6/2011 | Michlitsch et al. | |
| 7,959,050 B2 | 6/2011 | Smith et al. | |
| 7,963,907 B2 | 6/2011 | Gertner | |
| 7,966,799 B2 | 6/2011 | Morgan et al. | |
| 7,992,757 B2 | 8/2011 | Wheeler et al. | |
| 7,997,469 B2 | 8/2011 | Olson et al. | |
| 8,016,176 B2 | 9/2011 | Kasvikis et al. | |
| 8,020,741 B2 | 9/2011 | Cole et al. | |
| 8,028,884 B2 | 10/2011 | Sniffin et al. | |
| 8,033,442 B2 | 10/2011 | Racenet et al. | |
| 8,034,077 B2 | 10/2011 | Smith et al. | |
| 8,052,697 B2 | 11/2011 | Phillips | |
| 8,056,788 B2 | 11/2011 | Mastri et al. | |
| 8,061,577 B2 | 11/2011 | Racenet et al. | |
| 8,062,236 B2 | 11/2011 | Soltz | |
| 8,066,168 B2 | 11/2011 | Vidal et al. | |
| 8,070,034 B1 | 12/2011 | Knodel | |
| 8,070,036 B1 | 12/2011 | Knodel | |
| 8,087,563 B2 | 1/2012 | Milliman et al. | |
| 8,091,756 B2 | 1/2012 | Viola | |
| 8,096,459 B2 | 1/2012 | Ortiz et al. | |
| 8,113,406 B2 | 2/2012 | Holsten et al. | |
| 8,132,704 B2 | 3/2012 | Whitman et al. | |
| 8,141,762 B2 | 3/2012 | Bedi et al. | |
| 8,147,506 B2 | 4/2012 | Ortiz et al. | |
| 8,167,186 B2 | 5/2012 | Racenet et al. | |
| 8,172,122 B2 | 5/2012 | Kasvikis et al. | |
| 8,186,560 B2 | 5/2012 | Hess et al. | |
| 8,196,795 B2 | 6/2012 | Moore et al. | |
| 8,205,780 B2 | 6/2012 | Sorrentino et al. | |
| 8,210,415 B2 | 7/2012 | Ward | |
| 8,216,159 B1 * | 7/2012 | Leiboff | A61B 90/06 600/593 |
| 8,220,690 B2 | 7/2012 | Hess et al. | |
| 8,226,602 B2 | 7/2012 | Quijana et al. | |
| 8,245,898 B2 | 8/2012 | Smith et al. | |
| 8,252,009 B2 | 8/2012 | Weller et al. | |
| 8,256,655 B2 | 9/2012 | Sniffin et al. | |
| 8,276,801 B2 | 10/2012 | Zemlok et al. | |
| 8,292,153 B2 | 10/2012 | Jankowski | |
| 8,308,725 B2 | 11/2012 | Bell et al. | |
| 8,317,070 B2 | 11/2012 | Hueil et al. | |
| 8,322,455 B2 | 12/2012 | Shelton, IV et al. | |
| 8,328,061 B2 | 12/2012 | Kasvikis | |
| 8,328,064 B2 | 12/2012 | Racenet et al. | |
| 8,343,175 B2 | 1/2013 | Ewers et al. | |
| 8,348,127 B2 | 1/2013 | Marczyk | |
| 8,348,129 B2 | 1/2013 | Bedi et al. | |
| 8,348,130 B2 | 1/2013 | Shah et al. | |
| 8,348,131 B2 | 1/2013 | Omaits et al. | |
| 8,353,436 B2 | 1/2013 | Kasvikis | |
| 8,360,297 B2 | 1/2013 | Shelton, IV et al. | |
| 8,365,973 B1 | 2/2013 | White et al. | |
| 8,365,976 B2 | 2/2013 | Hess et al. | |
| 8,382,775 B1 | 2/2013 | Bender et al. | |
| 8,393,513 B2 | 3/2013 | Jankowski | |
| 8,393,514 B2 | 3/2013 | Shelton, IV et al. | |
| 8,403,956 B1 | 3/2013 | Thompson et al. | |
| 8,408,442 B2 | 4/2013 | Racenet et al. | |
| 8,424,739 B2 | 4/2013 | Racenet et al. | |
| 8,439,244 B2 | 5/2013 | Holcomb et al. | |
| 8,439,246 B1 | 5/2013 | Knodel | |
| 8,449,460 B2 | 5/2013 | Duke et al. | |
| 8,449,560 B2 | 5/2013 | Roth et al. | |
| 8,453,912 B2 | 6/2013 | Mastri et al. | |
| 8,453,913 B2 | 6/2013 | Laurent et al. | |
| 8,464,923 B2 | 6/2013 | Shelton, IV | |
| 8,465,507 B2 | 6/2013 | Cosgrove et al. | |
| 8,469,252 B2 | 6/2013 | Holcomb et al. | |
| 8,469,977 B2 | 6/2013 | Balbierz et al. | |
| 8,479,969 B2 | 7/2013 | Shelton, IV | |
| 8,485,412 B2 | 7/2013 | Shelton, IV et al. | |
| 8,496,155 B2 | 7/2013 | Knodel | |
| 8,496,156 B2 | 7/2013 | Sniffin et al. | |
| 8,499,993 B2 | 8/2013 | Shelton, IV et al. | |
| 8,523,041 B2 | 9/2013 | Ishitsuki et al. | |
| 8,529,585 B2 | 9/2013 | Jacobs et al. | |
| 8,540,128 B2 | 9/2013 | Shelton, IV et al. | |
| 8,540,130 B2 | 9/2013 | Moore et al. | |
| 8,544,712 B2 | 10/2013 | Jankowski | |
| 8,561,872 B2 | 10/2013 | Wheeler et al. | |
| 8,573,465 B2 | 11/2013 | Shelton, IV | |
| 8,574,243 B2 | 11/2013 | Saadat et al. | |
| 8,579,176 B2 | 11/2013 | Smith et al. | |
| 8,579,178 B2 | 11/2013 | Holsten et al. | |
| 8,590,762 B2 | 11/2013 | Hess et al. | |
| 8,596,513 B2 | 12/2013 | Olson et al. | |
| 8,608,043 B2 | 12/2013 | Scirica | |

(56) References Cited

U.S. PATENT DOCUMENTS

| | | |
|---|---|---|
| 8,608,046 B2 | 12/2013 | Laurent et al. |
| 8,613,384 B2 | 12/2013 | Pastorelli et al. |
| 8,616,431 B2 | 12/2013 | Timm et al. |
| 8,617,185 B2 | 12/2013 | Bonutti et al. |
| 8,628,544 B2 | 1/2014 | Farascioni |
| 8,628,547 B2 | 1/2014 | Weller et al. |
| 8,647,350 B2 | 2/2014 | Mohan et al. |
| 8,663,245 B2 | 3/2014 | Francischelli et al. |
| 8,668,130 B2 | 3/2014 | Hess et al. |
| 8,672,208 B2 | 3/2014 | Hess et al. |
| 8,672,830 B2 | 3/2014 | Dlugos, Jr. et al. |
| 8,701,958 B2 | 4/2014 | Shelton, IV et al. |
| 8,714,429 B2 | 5/2014 | Demmy |
| 8,720,766 B2 | 5/2014 | Hess et al. |
| 8,727,197 B2 | 5/2014 | Hess et al. |
| 8,727,199 B2 | 5/2014 | Wenchell |
| 8,733,613 B2 | 5/2014 | Huitema et al. |
| 8,740,035 B2 | 6/2014 | Mastri et al. |
| 8,758,392 B2 | 6/2014 | Crainich |
| 8,763,875 B2 | 7/2014 | Morgan et al. |
| 8,800,838 B2 | 8/2014 | Shelton, IV |
| 8,800,840 B2 | 8/2014 | Jankowski |
| 8,801,732 B2 | 8/2014 | Harris et al. |
| 8,808,161 B2 | 8/2014 | Gregg et al. |
| 8,808,325 B2 | 8/2014 | Hess et al. |
| 8,840,004 B2 | 9/2014 | Holsten et al. |
| 8,852,218 B2 | 10/2014 | Hughett, Sr. et al. |
| 8,864,009 B2 | 10/2014 | Shelton, IV et al. |
| 8,882,766 B2 | 11/2014 | Couture et al. |
| 8,899,465 B2 | 12/2014 | Shelton, IV et al. |
| 8,925,788 B2 | 1/2015 | Hess et al. |
| 8,945,163 B2 | 2/2015 | Voegele et al. |
| 8,956,390 B2 | 2/2015 | Shah et al. |
| 8,973,804 B2 | 3/2015 | Hess et al. |
| 8,978,956 B2 | 3/2015 | Schall et al. |
| 8,991,676 B2 | 3/2015 | Hess et al. |
| 8,991,677 B2 | 3/2015 | Moore et al. |
| 8,998,058 B2 | 4/2015 | Moore et al. |
| 9,011,437 B2 | 4/2015 | Woodruff et al. |
| 9,016,541 B2 | 4/2015 | Viola et al. |
| 9,033,203 B2 | 5/2015 | Woodard, Jr. et al. |
| 9,050,084 B2 | 6/2015 | Schmid et al. |
| 9,066,721 B2 | 6/2015 | Ichihara et al. |
| 9,084,600 B1 | 7/2015 | Knodel et al. |
| 9,084,601 B2 | 7/2015 | Moore et al. |
| 9,095,339 B2 | 8/2015 | Moore et al. |
| 9,113,862 B2 | 8/2015 | Morgan et al. |
| 9,113,868 B2 | 8/2015 | Felder et al. |
| 9,119,627 B2 | 9/2015 | Cosgrove et al. |
| 9,138,226 B2 | 9/2015 | Racenet et al. |
| 9,149,325 B2 | 10/2015 | Worrell et al. |
| 9,155,528 B2 | 10/2015 | Bender et al. |
| 9,168,039 B1 | 10/2015 | Knodel |
| 9,179,911 B2 | 11/2015 | Morgan et al. |
| 9,180,035 B2 | 11/2015 | Stack et al. |
| 9,211,120 B2 | 12/2015 | Scheib et al. |
| 9,216,019 B2 | 12/2015 | Schmid et al. |
| 9,254,131 B2 | 2/2016 | Soltz et al. |
| 9,289,206 B2 | 3/2016 | Hess et al. |
| 9,289,207 B2 | 3/2016 | Shelton, IV |
| 9,307,981 B2 | 4/2016 | Mikkaichi et al. |
| 9,314,362 B2 | 4/2016 | Bender et al. |
| 9,326,768 B2 | 5/2016 | Shelton, IV |
| 9,339,442 B2 | 5/2016 | Tai et al. |
| 9,345,478 B2 | 5/2016 | Knodel |
| 9,364,225 B2 | 6/2016 | Sniffin et al. |
| 9,370,362 B2 | 6/2016 | Petty et al. |
| 9,398,917 B2 | 7/2016 | Whitfield et al. |
| 9,408,604 B2 | 8/2016 | Shelton, IV et al. |
| 9,433,411 B2 | 9/2016 | Racenet et al. |
| 9,439,633 B2 | 9/2016 | O'Dea |
| 9,498,219 B2 | 11/2016 | Moore et al. |
| 9,549,733 B2 | 1/2017 | Knodel |
| 9,561,032 B2 | 2/2017 | Shelton, IV et al. |
| 9,603,595 B2 | 3/2017 | Shelton, IV et al. |
| 9,603,598 B2 | 3/2017 | Shelton, IV et al. |
| 9,615,952 B2 | 4/2017 | Scott et al. |
| 9,636,114 B2 | 5/2017 | Cole et al. |
| 9,675,355 B2 | 6/2017 | Shelton, IV et al. |
| 9,687,233 B2 | 6/2017 | Fernandez et al. |
| 9,687,237 B2 | 6/2017 | Schmid et al. |
| 9,693,816 B2 | 7/2017 | Orszulak |
| 9,700,321 B2 | 7/2017 | Shelton, IV et al. |
| 9,706,991 B2 | 7/2017 | Hess et al. |
| 9,724,091 B2 | 8/2017 | Shelton, IV et al. |
| 9,724,093 B2 | 8/2017 | Farascioni et al. |
| 9,724,096 B2 | 8/2017 | Thompson et al. |
| 9,730,692 B2 | 8/2017 | Shelton, IV et al. |
| 9,775,613 B2 | 10/2017 | Shelton, IV et al. |
| 9,795,380 B2 | 10/2017 | Shelton, IV et al. |
| 9,801,627 B2 | 10/2017 | Harris et al. |
| 9,801,628 B2 | 10/2017 | Harris et al. |
| 9,801,630 B2 | 10/2017 | Harris et al. |
| 9,808,246 B2 | 11/2017 | Shelton, IV et al. |
| 9,808,257 B2 | 11/2017 | Armenteros et al. |
| 9,820,742 B2 | 11/2017 | Covach et al. |
| 9,827,002 B2 | 11/2017 | Hausen et al. |
| 9,844,370 B2 | 12/2017 | Viola et al. |
| 9,848,873 B2 | 12/2017 | Shelton, IV |
| 9,848,875 B2 | 12/2017 | Aronhalt et al. |
| 9,848,878 B2 | 12/2017 | Racenet et al. |
| 9,855,040 B2 | 1/2018 | Kostrzewski |
| 9,861,366 B2 | 1/2018 | Aranyi |
| 9,872,682 B2 | 1/2018 | Hess et al. |
| 9,901,344 B2 | 2/2018 | Moore et al. |
| 9,901,346 B2 | 2/2018 | Moore et al. |
| 9,913,646 B2 | 3/2018 | Shelton, IV |
| 9,924,947 B2 | 3/2018 | Shelton, IV et al. |
| 9,936,953 B2 | 4/2018 | Thompson et al. |
| 9,937,001 B2 | 4/2018 | Nakamura |
| 9,980,729 B2 | 5/2018 | Moore et al. |
| 9,999,426 B2 | 6/2018 | Moore et al. |
| 9,999,431 B2 | 6/2018 | Shelton, IV et al. |
| 10,004,505 B2 | 6/2018 | Moore et al. |
| 10,045,780 B2 | 8/2018 | Adams et al. |
| 10,085,751 B2 | 10/2018 | Overmyer et al. |
| 10,085,754 B2 | 10/2018 | Sniffin et al. |
| 10,130,360 B2 | 11/2018 | Olson et al. |
| 10,130,363 B2 | 11/2018 | Huitema et al. |
| 10,172,616 B2 | 1/2019 | Murray et al. |
| 10,194,912 B2 | 2/2019 | Scheib et al. |
| 10,226,250 B2 | 3/2019 | Beckman et al. |
| 10,231,734 B2 | 3/2019 | Thompson et al. |
| 10,238,517 B2 | 3/2019 | Gingras |
| 10,245,032 B2 | 4/2019 | Shelton, IV |
| 10,258,334 B2 | 4/2019 | Adams et al. |
| 10,265,073 B2 | 4/2019 | Scheib et al. |
| 10,278,695 B2 | 5/2019 | Milo |
| 10,278,699 B2 | 5/2019 | Thompson et al. |
| 10,278,707 B2 | 5/2019 | Thompson et al. |
| 10,285,712 B2 | 5/2019 | Cosgrove, III et al. |
| 10,285,837 B1 | 5/2019 | Thompson et al. |
| 10,292,706 B2 | 5/2019 | Jankowski |
| 10,307,161 B2 | 6/2019 | Jankowski |
| 10,307,163 B2 | 6/2019 | Moore et al. |
| 10,314,580 B2 | 6/2019 | Scheib et al. |
| 10,314,589 B2 | 6/2019 | Shelton, IV et al. |
| 10,342,538 B2 | 7/2019 | Racenet et al. |
| 10,383,628 B2 | 8/2019 | Kang et al. |
| 10,390,826 B2 | 8/2019 | Badawi |
| 10,405,856 B2 | 9/2019 | Knodel |
| 10,405,860 B2 | 9/2019 | Thompson et al. |
| 10,420,559 B2 | 9/2019 | Marczyk et al. |
| 10,420,560 B2 | 9/2019 | Shelton, IV et al. |
| 10,441,283 B1 | 10/2019 | Thompson et al. |
| 10,456,571 B2 | 10/2019 | Cairns |
| 10,470,911 B2 | 11/2019 | Thompson et al. |
| 10,485,540 B2 | 11/2019 | Hodgkinson et al. |
| 10,499,912 B2 | 12/2019 | Scheib et al. |
| 10,537,325 B2 | 1/2020 | Bakos et al. |
| 10,542,986 B2 | 1/2020 | Thompson et al. |
| 10,548,597 B2 | 2/2020 | Dunki-Jacobs et al. |
| 10,610,226 B2 | 4/2020 | Shelton et al. |
| 10,624,638 B2 | 4/2020 | Thompson et al. |

(56) References Cited

U.S. PATENT DOCUMENTS

| | | | |
|---|---|---|---|
| 10,687,807 B2 | 6/2020 | Simms et al. |
| 10,687,810 B2 | 6/2020 | Shelton, IV et al. |
| 10,687,814 B2 | 6/2020 | Dunki-Jacobs et al. |
| 10,716,564 B2 | 7/2020 | Shelton, IV et al. |
| 10,758,231 B2 | 9/2020 | Harris et al. |
| 10,849,623 B2 | 12/2020 | Dunki-Jacobs et al. |
| 10,912,562 B2 | 2/2021 | Dunki-Jacobs et al. |
| 10,966,721 B2 | 4/2021 | Dunki-Jacobs et al. |
| 10,987,108 B2 | 4/2021 | Thompson et al. |
| 11,173,060 B2 | 11/2021 | Thompson et al. |
| 11,197,672 B2 | 12/2021 | Dunki-Jacobs et al. |
| 2001/0044656 A1 | 11/2001 | Williamson, IV et al. |
| 2002/0143346 A1 | 10/2002 | Mcguckin, Jr. et al. |
| 2003/0125734 A1 | 7/2003 | Mollenauer |
| 2003/0135091 A1* | 7/2003 | Nakazawa | A61B 1/313 |
| | | | 600/101 |
| 2003/0208209 A1 | 11/2003 | Gambale et al. |
| 2003/0220660 A1 | 11/2003 | Kortenbach et al. |
| 2004/0006351 A1 | 1/2004 | Gannoe et al. |
| 2004/0006372 A1 | 1/2004 | Racenet et al. |
| 2004/0068267 A1 | 4/2004 | Harvie et al. |
| 2004/0181239 A1 | 9/2004 | Dorn et al. |
| 2004/0215216 A1 | 10/2004 | Gannoe et al. |
| 2005/0006432 A1 | 1/2005 | Racenet et al. |
| 2005/0080444 A1 | 4/2005 | Kraemer et al. |
| 2005/0139633 A1 | 6/2005 | Wukusick et al. |
| 2005/0203547 A1 | 9/2005 | Weller et al. |
| 2005/0203548 A1 | 9/2005 | Weller et al. |
| 2005/0256533 A1 | 11/2005 | Roth et al. |
| 2006/0011698 A1 | 1/2006 | Okada et al. |
| 2006/0016853 A1 | 1/2006 | Racenet |
| 2006/0020277 A1 | 1/2006 | Gostout et al. |
| 2006/0036267 A1 | 2/2006 | Saadat et al. |
| 2006/0041270 A1 | 2/2006 | Lenker et al. |
| 2006/0085030 A1 | 4/2006 | Bettuchi et al. |
| 2006/0151568 A1 | 7/2006 | Weller et al. |
| 2006/0229665 A1 | 10/2006 | Wales et al. |
| 2006/0241692 A1 | 10/2006 | McGuckin et al. |
| 2007/0023477 A1 | 2/2007 | Whitman et al. |
| 2007/0027469 A1 | 2/2007 | Smith et al. |
| 2007/0029364 A1 | 2/2007 | Kruszynski et al. |
| 2007/0034666 A1 | 2/2007 | Holsten et al. |
| 2007/0034667 A1 | 2/2007 | Holsten et al. |
| 2007/0039997 A1 | 2/2007 | Mather et al. |
| 2007/0056932 A1 | 3/2007 | Whitman et al. |
| 2007/0075114 A1 | 4/2007 | Shelton et al. |
| 2007/0083233 A1 | 4/2007 | Ortiz et al. |
| 2007/0131732 A1 | 6/2007 | Holsten et al. |
| 2007/0179528 A1 | 8/2007 | Soltz et al. |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0213743 A1 | 9/2007 | McGuckin, Jr. |
| 2007/0246505 A1 | 10/2007 | Pace-Floridia et al. |
| 2007/0262116 A1 | 11/2007 | Hueil et al. |
| 2008/0015631 A1 | 1/2008 | Lee et al. |
| 2008/0023522 A1 | 1/2008 | Olson et al. |
| 2008/0033457 A1 | 2/2008 | Francischelli et al. |
| 2008/0035702 A1 | 2/2008 | Holsten et al. |
| 2008/0041918 A1 | 2/2008 | Holsten et al. |
| 2008/0058716 A1 | 3/2008 | Dubrul et al. |
| 2008/0078800 A1 | 4/2008 | Hess et al. |
| 2008/0082124 A1 | 4/2008 | Hess et al. |
| 2008/0087707 A1 | 4/2008 | Jankowski |
| 2008/0097332 A1 | 4/2008 | Greenhalgh et al. |
| 2008/0149684 A1 | 6/2008 | Viola |
| 2008/0164297 A1 | 7/2008 | Holsten et al. |
| 2008/0169329 A1 | 7/2008 | Shelton et al. |
| 2008/0169332 A1 | 7/2008 | Shelton et al. |
| 2008/0190990 A1 | 8/2008 | Holsten et al. |
| 2008/0203134 A1 | 8/2008 | Shah et al. |
| 2008/0249404 A1 | 10/2008 | Mikkaichi et al. |
| 2008/0275480 A1 | 11/2008 | Jacobs et al. |
| 2008/0294179 A1 | 11/2008 | Balbierz et al. |
| 2008/0308602 A1 | 12/2008 | Timm et al. |
| 2009/0001122 A1 | 1/2009 | Prommersberger et al. |
| 2009/0001130 A1 | 1/2009 | Hess et al. |
| 2009/0012556 A1 | 1/2009 | Boudreaux et al. |
| 2009/0020584 A1 | 1/2009 | Soltz et al. |
| 2009/0078739 A1 | 3/2009 | Viola |
| 2009/0095791 A1 | 4/2009 | Eskaros et al. |
| 2009/0101692 A1 | 4/2009 | Whitman et al. |
| 2009/0134200 A1 | 5/2009 | Tarinelli et al. |
| 2009/0173766 A1 | 7/2009 | Wenchell |
| 2009/0209946 A1 | 8/2009 | Swayze et al. |
| 2009/0209986 A1 | 8/2009 | Stewart et al. |
| 2009/0212088 A1 | 8/2009 | Okada et al. |
| 2009/0255974 A1 | 10/2009 | Viola |
| 2009/0261144 A1 | 10/2009 | Sniffin et al. |
| 2009/0308907 A1 | 12/2009 | Nalagatla et al. |
| 2010/0010512 A1 | 1/2010 | Taylor et al. |
| 2010/0072255 A1 | 3/2010 | Olson et al. |
| 2010/0072258 A1 | 3/2010 | Farascioni et al. |
| 2010/0108739 A1 | 5/2010 | Holsten et al. |
| 2010/0114124 A1 | 5/2010 | Kelleher et al. |
| 2010/0121356 A1 | 5/2010 | Hartmann et al. |
| 2010/0137904 A1 | 6/2010 | Wenchell |
| 2010/0145324 A1 | 6/2010 | Nihalani |
| 2010/0213240 A1 | 8/2010 | Kostrzewski |
| 2010/0256634 A1 | 10/2010 | Voegele et al. |
| 2010/0282820 A1 | 11/2010 | Kasvikis |
| 2010/0331866 A1 | 12/2010 | Surti et al. |
| 2011/0004062 A1 | 1/2011 | Asai et al. |
| 2011/0017800 A1 | 1/2011 | Viola |
| 2011/0036888 A1 | 2/2011 | Pribanic et al. |
| 2011/0046653 A1* | 2/2011 | Addington | A61B 5/202 |
| | | | 606/196 |
| 2011/0071555 A1 | 3/2011 | McBrayer et al. |
| 2011/0084113 A1 | 4/2011 | Bedi et al. |
| 2011/0087169 A1 | 4/2011 | Parihar et al. |
| 2011/0087279 A1 | 4/2011 | Shah et al. |
| 2011/0152895 A1 | 6/2011 | Nyuli et al. |
| 2011/0160752 A1 | 6/2011 | Aguirre |
| 2011/0178454 A1 | 7/2011 | Gagner et al. |
| 2011/0186614 A1 | 8/2011 | Kasvikis |
| 2011/0190791 A1 | 8/2011 | Jacobs et al. |
| 2011/0208211 A1 | 8/2011 | Whitfield et al. |
| 2011/0226837 A1 | 9/2011 | Baxter, III et al. |
| 2011/0278343 A1 | 11/2011 | Knodel et al. |
| 2011/0290851 A1 | 12/2011 | Shelton, IV |
| 2011/0315739 A1 | 12/2011 | Sniffin et al. |
| 2012/0035631 A1 | 2/2012 | Hughett, Sr et al. |
| 2012/0059400 A1 | 3/2012 | Williamson, IV et al. |
| 2012/0080494 A1 | 4/2012 | Thompson et al. |
| 2012/0123463 A1 | 5/2012 | Jacobs |
| 2012/0175398 A1 | 7/2012 | Sandborn et al. |
| 2012/0203247 A1 | 8/2012 | Shelton, IV et al. |
| 2012/0234899 A1 | 9/2012 | Scheib et al. |
| 2012/0234900 A1 | 9/2012 | Swayze |
| 2012/0248169 A1 | 10/2012 | Widenhouse et al. |
| 2012/0277525 A1 | 11/2012 | O'Dea |
| 2012/0286022 A1 | 11/2012 | Olson et al. |
| 2012/0289979 A1 | 11/2012 | Eskaros et al. |
| 2013/0062394 A1 | 3/2013 | Smith et al. |
| 2013/0075447 A1 | 3/2013 | Weisenburgh, II et al. |
| 2013/0075450 A1 | 3/2013 | Schmid et al. |
| 2013/0092718 A1 | 4/2013 | Soltz et al. |
| 2013/0105549 A1 | 5/2013 | Holsten et al. |
| 2013/0131440 A1 | 5/2013 | Gabriel |
| 2013/0146638 A1 | 6/2013 | Mandakolathur Vasudevan et al. |
| 2013/0146641 A1 | 6/2013 | Shelton, IV et al. |
| 2013/0146642 A1 | 6/2013 | Shelton, IV et al. |
| 2013/0153625 A1 | 6/2013 | Felder et al. |
| 2013/0153634 A1 | 6/2013 | Carter et al. |
| 2013/0153642 A1 | 6/2013 | Felder et al. |
| 2013/0161374 A1 | 6/2013 | Swayze et al. |
| 2013/0165774 A1* | 6/2013 | Nocca | A61F 5/0089 |
| | | | 600/431 |
| 2013/0172929 A1 | 7/2013 | Hess et al. |
| 2013/0193190 A1 | 8/2013 | Carter et al. |
| 2013/0214025 A1 | 8/2013 | Zemlok et al. |
| 2013/0245652 A1 | 9/2013 | Cosgrove et al. |
| 2013/0256372 A1 | 10/2013 | Baxter, III et al. |
| 2013/0256375 A1 | 10/2013 | Shelton, IV et al. |

(56) References Cited

U.S. PATENT DOCUMENTS

| | | |
|---|---|---|
| 2013/0256377 A1 | 10/2013 | Schmid et al. |
| 2013/0284791 A1 | 10/2013 | Olson et al. |
| 2013/0306704 A1 | 11/2013 | Balbierz et al. |
| 2013/0327809 A1 | 12/2013 | Shelton, IV et al. |
| 2013/0334288 A1 | 12/2013 | Shelton, IV |
| 2013/0341374 A1 | 12/2013 | Shelton, IV et al. |
| 2014/0005678 A1 | 1/2014 | Shelton, IV et al. |
| 2014/0008412 A1 | 1/2014 | Zemlok et al. |
| 2014/0018722 A1 | 1/2014 | Scott et al. |
| 2014/0027493 A1 | 1/2014 | Jankowski |
| 2014/0046345 A1 | 2/2014 | Armenteros et al. |
| 2014/0074131 A1 | 3/2014 | Armenteros et al. |
| 2014/0081176 A1 | 3/2014 | Hassan |
| 2014/0082497 A1 | 3/2014 | Chalouhi et al. |
| 2014/0107698 A1 | 4/2014 | Inge |
| 2014/0110457 A1 | 4/2014 | Zhang et al. |
| 2014/0114121 A1* | 4/2014 | Trivedi ............... A61F 5/0083 600/37 |
| 2014/0131418 A1 | 5/2014 | Kostrzewski |
| 2014/0131419 A1 | 5/2014 | Bettuchi |
| 2014/0144968 A1 | 5/2014 | Shelton, IV |
| 2014/0148731 A1 | 5/2014 | Radl et al. |
| 2014/0171744 A1 | 6/2014 | Racenet et al. |
| 2014/0183242 A1 | 7/2014 | Farascioni et al. |
| 2014/0184519 A1 | 7/2014 | Benchenaa et al. |
| 2014/0191015 A1 | 7/2014 | Shelton, IV |
| 2014/0214025 A1 | 7/2014 | Worrell et al. |
| 2014/0231489 A1 | 8/2014 | Balbierz et al. |
| 2014/0239037 A1 | 8/2014 | Boudreaux et al. |
| 2014/0257353 A1 | 9/2014 | Whitman et al. |
| 2014/0263570 A1 | 9/2014 | Hopkins et al. |
| 2014/0276932 A1 | 9/2014 | Williams et al. |
| 2014/0291379 A1 | 10/2014 | Schellin et al. |
| 2015/0048141 A1 | 2/2015 | Felder et al. |
| 2015/0083780 A1 | 3/2015 | Shelton, IV et al. |
| 2015/0133740 A1* | 5/2015 | Dierking ............ A61B 17/0218 600/249 |
| 2015/0157318 A1 | 6/2015 | Beardsley et al. |
| 2015/0173746 A1 | 6/2015 | Baxter, III et al. |
| 2015/0173755 A1 | 6/2015 | Baxter, III et al. |
| 2015/0173762 A1 | 6/2015 | Shelton, IV et al. |
| 2015/0209034 A1 | 7/2015 | Viola et al. |
| 2015/0265276 A1 | 9/2015 | Huitema et al. |
| 2015/0297224 A1 | 10/2015 | Hall et al. |
| 2015/0297227 A1 | 10/2015 | Huitema et al. |
| 2015/0320423 A1 | 11/2015 | Aranyi |
| 2015/0351764 A1 | 12/2015 | Shelton, IV |
| 2016/0058447 A1 | 3/2016 | Posada et al. |
| 2016/0058594 A1 | 3/2016 | Armenteros et al. |
| 2016/0066916 A1 | 3/2016 | Overmyer et al. |
| 2016/0067074 A1 | 3/2016 | Thompson et al. |
| 2016/0089148 A1 | 3/2016 | Harris et al. |
| 2016/0166256 A1 | 6/2016 | Baxter, III et al. |
| 2016/0183945 A1 | 6/2016 | Shelton, IV et al. |
| 2016/0199061 A1 | 7/2016 | Shelton, IV et al. |
| 2016/0199088 A1 | 7/2016 | Shelton, IV et al. |
| 2016/0213302 A1 | 7/2016 | Frushour |
| 2016/0235409 A1 | 8/2016 | Shelton, IV et al. |
| 2016/0242768 A1 | 8/2016 | Moore et al. |
| 2016/0242769 A1 | 8/2016 | Moore et al. |
| 2016/0242770 A1 | 8/2016 | Moore et al. |
| 2016/0242783 A1 | 8/2016 | Shelton, IV et al. |
| 2016/0256152 A1 | 9/2016 | Kostrzewski |
| 2016/0262744 A1 | 9/2016 | Milo et al. |
| 2016/0262750 A1 | 9/2016 | Hausen et al. |
| 2016/0262921 A1 | 9/2016 | Balbierz et al. |
| 2016/0270792 A1 | 9/2016 | Sniffin et al. |
| 2016/0287251 A1 | 10/2016 | Shelton, IV |
| 2016/0296272 A1 | 10/2016 | Heard |
| 2016/0324527 A1 | 11/2016 | Thompson et al. |
| 2016/0354085 A1 | 12/2016 | Shelton, IV et al. |
| 2016/0367250 A1 | 12/2016 | Racenet et al. |
| 2017/0007248 A1 | 1/2017 | Shelton, IV et al. |
| 2017/0014125 A1 | 1/2017 | Shelton, IV et al. |
| 2017/0027633 A1 | 2/2017 | Wham et al. |
| 2017/0055981 A1 | 3/2017 | Vendely et al. |
| 2017/0055991 A1 | 3/2017 | Kang |
| 2017/0056016 A1 | 3/2017 | Barton et al. |
| 2017/0086847 A1 | 3/2017 | DiNardo et al. |
| 2017/0095251 A1 | 4/2017 | Thompson et al. |
| 2017/0105728 A1 | 4/2017 | Scheib et al. |
| 2017/0172571 A1 | 6/2017 | Thompson et al. |
| 2017/0231633 A1 | 8/2017 | Marczyk et al. |
| 2017/0290588 A1 | 10/2017 | Thompson et al. |
| 2017/0303952 A1 | 10/2017 | Nativ et al. |
| 2017/0319210 A1 | 11/2017 | Moore et al. |
| 2017/0333041 A1 | 11/2017 | Moore et al. |
| 2017/0360447 A1 | 12/2017 | Armenteros et al. |
| 2017/0367697 A1 | 12/2017 | Shelton, IV et al. |
| 2018/0014826 A1 | 1/2018 | Scheib et al. |
| 2018/0036000 A1 | 2/2018 | Terada et al. |
| 2018/0036005 A1 | 2/2018 | Covach et al. |
| 2018/0092641 A1 | 4/2018 | Aranyi |
| 2018/0168594 A1 | 6/2018 | Shelton, IV et al. |
| 2018/0168620 A1 | 6/2018 | Huang et al. |
| 2018/0168633 A1 | 6/2018 | Shelton, IV et al. |
| 2018/0199939 A1 | 7/2018 | Thompson et al. |
| 2018/0199941 A1 | 7/2018 | Thompson et al. |
| 2018/0235625 A1 | 8/2018 | Shelton, IV et al. |
| 2018/0235626 A1 | 8/2018 | Shelton, IV et al. |
| 2018/0280020 A1 | 10/2018 | Hess et al. |
| 2018/0317905 A1 | 11/2018 | Olson et al. |
| 2019/0000455 A1 | 1/2019 | Adams et al. |
| 2019/0046186 A1 | 2/2019 | Dunki-Jacobs et al. |
| 2019/0046189 A1 | 2/2019 | Dunki-Jacobs et al. |
| 2019/0046190 A1 | 2/2019 | Dunki-Jacobs et al. |
| 2019/0046191 A1 | 2/2019 | Dunki-Jacobs et al. |
| 2019/0046192 A1 | 2/2019 | Dunki-Jacobs et al. |
| 2019/0046193 A1 | 2/2019 | Dunki-Jacobs et al. |
| 2019/0105042 A1 | 4/2019 | Huitema et al. |
| 2019/0133577 A1 | 5/2019 | Weadock et al. |
| 2019/0150924 A1 | 5/2019 | Thompson et al. |
| 2019/0209173 A1 | 7/2019 | Thompson et al. |
| 2019/0209175 A1 | 7/2019 | Thompson et al. |
| 2019/0224029 A1 | 7/2019 | Thompson et al. |
| 2019/0261985 A1 | 8/2019 | Adams et al. |
| 2019/0261991 A1 | 8/2019 | Beckman et al. |
| 2019/0269408 A1 | 9/2019 | Jankowski |
| 2019/0274677 A1 | 9/2019 | Shelton, IV |
| 2019/0274678 A1 | 9/2019 | Shelton, IV |
| 2019/0274679 A1 | 9/2019 | Shelton, IV |
| 2019/0274680 A1 | 9/2019 | Shelton, IV |
| 2019/0307450 A1 | 10/2019 | Thompson et al. |
| 2019/0343519 A1 | 11/2019 | Thompson et al. |
| 2019/0380742 A1 | 12/2019 | Hall et al. |
| 2019/0388092 A1 | 12/2019 | Thompson et al. |
| 2020/0008964 A1 | 1/2020 | Thompson et al. |
| 2020/0015822 A1 | 1/2020 | Marczyk et al. |
| 2020/0054326 A1 | 2/2020 | Harris et al. |
| 2020/0100790 A1 | 4/2020 | DiNardo et al. |
| 2020/0205810 A1 | 7/2020 | Posey et al. |
| 2020/0205827 A1 | 7/2020 | Bakos et al. |
| 2020/0206805 A1 | 7/2020 | Nalagatla et al. |
| 2020/0214703 A1 | 7/2020 | Thompson et al. |
| 2020/0229818 A1 | 7/2020 | Thompson et al. |
| 2020/0268385 A1 | 8/2020 | Dunki-Jacobs et al. |
| 2020/0297344 A1 | 9/2020 | Dunki-Jacobs et al. |
| 2020/0305865 A1 | 10/2020 | Shelton, IV |
| 2020/0305868 A1 | 10/2020 | Shelton, IV |
| 2020/0305869 A1 | 10/2020 | Shelton, IV |
| 2020/0305873 A1 | 10/2020 | Dunki-Jacobs et al. |
| 2020/0390443 A1 | 12/2020 | Thompson et al. |
| 2021/0177411 A1 | 6/2021 | Williams |
| 2021/0369330 A1 | 12/2021 | Brandt et al. |
| 2021/0393319 A1 | 12/2021 | Shelton, IV et al. |

FOREIGN PATENT DOCUMENTS

| | | |
|---|---|---|
| EP | 399699 A1 | 11/1990 |
| EP | 503662 A1 | 9/1992 |
| EP | 666057 A2 | 8/1995 |
| EP | 669104 A1 | 8/1995 |
| EP | 399699 B1 | 11/1995 |
| EP | 503662 B1 | 6/1997 |

(56) References Cited

FOREIGN PATENT DOCUMENTS

| | | | |
|---|---|---|---|
| EP | 1090592 A1 | 4/2001 |
| EP | 1616526 A1 | 1/2006 |
| EP | 1722691 A1 | 11/2006 |
| EP | 1769766 A1 | 4/2007 |
| EP | 1774916 A1 | 4/2007 |
| EP | 1806101 A1 | 7/2007 |
| EP | 1875868 A1 | 1/2008 |
| EP | 1875870 A1 | 1/2008 |
| EP | 1938759 A2 | 7/2008 |
| EP | 2005896 A2 | 12/2008 |
| EP | 2005897 A2 | 12/2008 |
| EP | 2005898 A2 | 12/2008 |
| EP | 2005899 A2 | 12/2008 |
| EP | 2005900 A2 | 12/2008 |
| EP | 2005901 A1 | 12/2008 |
| EP | 1774916 B1 | 2/2009 |
| EP | 2019633 A1 | 2/2009 |
| EP | 2090247 A1 | 8/2009 |
| EP | 2111803 A2 | 10/2009 |
| EP | 2245993 A2 | 11/2010 |
| EP | 2319424 A1 | 5/2011 |
| EP | 2382928 A1 | 11/2011 |
| EP | 2019633 B1 | 8/2012 |
| FR | 2731895 A1 | 9/1996 |
| GB | 2298905 A | 9/1996 |
| WO | 0154594 A1 | 8/2001 |
| WO | 2002060328 A1 | 8/2002 |
| WO | 03094747 A1 | 11/2003 |
| WO | 2007009099 A2 | 1/2007 |
| WO | 2007019268 A2 | 2/2007 |
| WO | 2007102152 A2 | 9/2007 |
| WO | 2008039238 A1 | 4/2008 |
| WO | 2008039249 A1 | 4/2008 |
| WO | 2008039250 A1 | 4/2008 |
| WO | 2008039270 A1 | 4/2008 |
| WO | 2008042021 A1 | 4/2008 |
| WO | 2008042022 A1 | 4/2008 |
| WO | 2008042043 A1 | 4/2008 |
| WO | 2008042044 A2 | 4/2008 |
| WO | 2008042045 A2 | 4/2008 |
| WO | 2008094210 A1 | 8/2008 |
| WO | 2008141288 A1 | 11/2008 |
| WO | 2009038550 A1 | 3/2009 |
| WO | 2010011661 A1 | 1/2010 |
| WO | 2011044032 A2 | 4/2011 |
| WO | 2011044032 A3 | 6/2011 |
| WO | 2011094700 A1 | 8/2011 |
| WO | 2012125615 A2 | 9/2012 |
| WO | 2012141679 A1 | 10/2012 |
| WO | 2013151888 A1 | 10/2013 |
| WO | 2014026170 A2 | 2/2014 |
| WO | 2014085099 A1 | 6/2014 |
| WO | 2015063609 A2 | 5/2015 |
| WO | 2015153324 A1 | 10/2015 |
| WO | 2015153340 A2 | 10/2015 |
| WO | 2016033221 A1 | 3/2016 |

OTHER PUBLICATIONS

De Petz, A; Aseptic Technic of Stomach Resections; 86 Annals of Surgery 388; Sep. 1927; 5 pages.
Dept. of Health and Human Services; CMS Description of Open Left Atrial Appendage Occlusion with "U" Fastener Implant; Mar. 9, 2011; 1 page.
European Search Report received in European Application No. 15774247; dated Dec. 23, 2016; 11 pages.
Examination Report received in Australian Application No. 2015241193; dated Dec. 11, 2018; 5 pages.
Examination Report received in Australian Application No. 2015241267; dated Feb. 25, 2019; 6 pages.
Examination Report received in Australian Application No. 2016208416; dated May 18, 2017; 4 pages.
Examination Report received in Australian Application No. 2018203527; dated Oct. 22, 2018; 5 pages.
Examination Report received in European Application No. 15772561; dated Oct. 29, 2018; 7 pages.
Harrah, J. D.; A Lung Clamp for Use with Mechanical Staplers; 28 The Annals of Thoracic Surgery 489; Nov. 1979; 2 pages.
International Preliminary Report on Patentability and Written Opinion of the International Searching Authority received in Application No. PCT/US2018/046743; dated Feb. 18, 2020; 17 pages.
International Preliminary Report on Patentability and Written Opinion of the International Searching Authority received in International Patent App. No. PCT/US2015/048740; dated Mar. 7, 2017; 8 pages.
International Search Report and Written Opinion of the International Searching Authority received in International Patent App. No. PCT/US2014/070869; dated Apr. 21, 2015; 17 pages.
International Search Report and Written Opinion of the International Searching Authority received in International Patent App. No. PCT/US2015/022904; dated Jun. 25, 2015; 6 pages.
International Search Report and Written Opinion of the International Searching Authority received in International Patent App. No. PCT/US2015/022990; dated Sep. 30, 2015; 10 pages.
International Search Report and Written Opinion of the International Searching Authority received in International Patent App. No. PCT/US2015/048740; dated Feb. 17, 2016; 12 pages.
International Search Report and Written Opinion of the International Searching Authority received in International Patent App. No. PCT/US2018/046743; dated Dec. 4, 2018; 20 pages.
Jacobs, M. et al.; Laparoscopic sleeve gastrectomy: a retrospective review of 1- and 2-year results; Surg Endosc. Apr. 24, 2010(4):781-5; doi: 10.1007/s00464-009-0619-8; Epub Aug. 19, 2009; abstract only; 2 pages.
LAAx, Inc.; 510(k) Summary for TigerPaw(R) System; published Oct. 29, 2010; 6 pages.
Parikh, M. et al.; Surgical Strategies That May Decrease Leak After Laparoscopic Sleeve Gastrectomy; 257 Annals of Surgery 231; Feb. 2013; 7 pages.
Parker, G.; A New Stomach Clamp; 26 Postgrad Med. J. 550; Oct. 1950; 1 page.
Pfiedler Enterprises; Science of Stapling: Urban Legend and Fact; Jun. 4, 2012; 38 pages.
Regan, J. P. et al.; Early Experience with Two-Stage Laparoscopic Roux-en-Y Gastric Bypass as an Alternative in the Super-Super Obese Patient; Obes Surg; 13(6):861-4; Dec. 1, 2003; abstract only; 2 pages.
Search Report received in Chinese Application No. 201480075706. 2; dated Nov. 28, 2018; 3 pages.
Steichen, F. M. et al.; Stapling in Surgery; Figures 1-11C; Year Book Medical Publishers, Inc.; 1984; 3 pages.
Supplementary European Search Report received in European Application No. 14872137; dated Mar. 28, 2017; 15 pages.
Supplementary European Search Report received in European Application No. 15772561; dated Mar. 15, 2017; 8 pages.
Supplementary Partial European Search Report received in European Application No. 14872137; dated Dec. 12, 2016; 5 pages.
Zuckerman, B. D., Food and Drug Administration; Letter to AtriCure, Inc. Addressing Indication for Use of AtriClip LAA Exclusion System w/Pre-loaded Gillnov-Cosgrove Clip; Jun. 10, 2010; 3 pages.
International Search Report and Written Opinion of the International Searching Authority received in International Patent Appln. No. PCT/US2022/021250; dated Jun. 10, 2022; 12 pages.
Communication pursuant to Article 94(3) EPC received in European Patent Appln. No. 18 845 739.4; dated Apr. 28, 2022; 9 pages.
Examination Report received in Australian Patent Appln. No. 2022204678; dated Jul. 7, 2022; 4 pages.

* cited by examiner

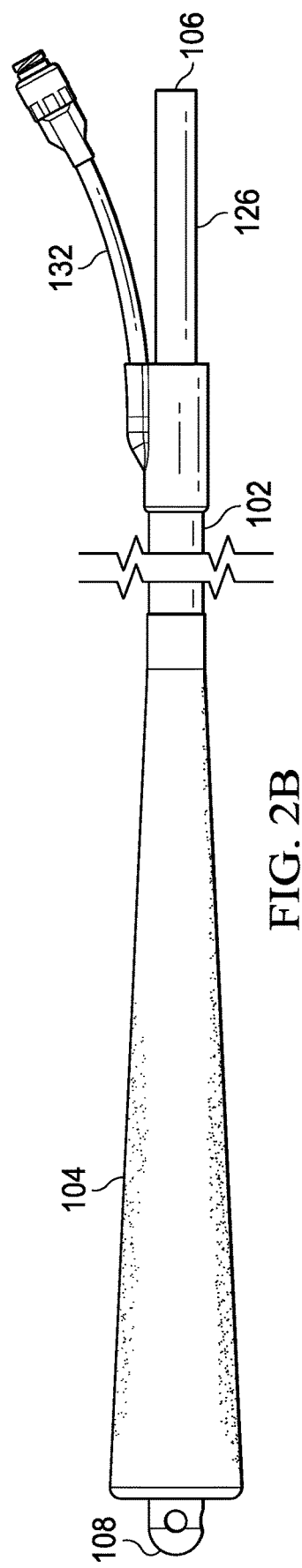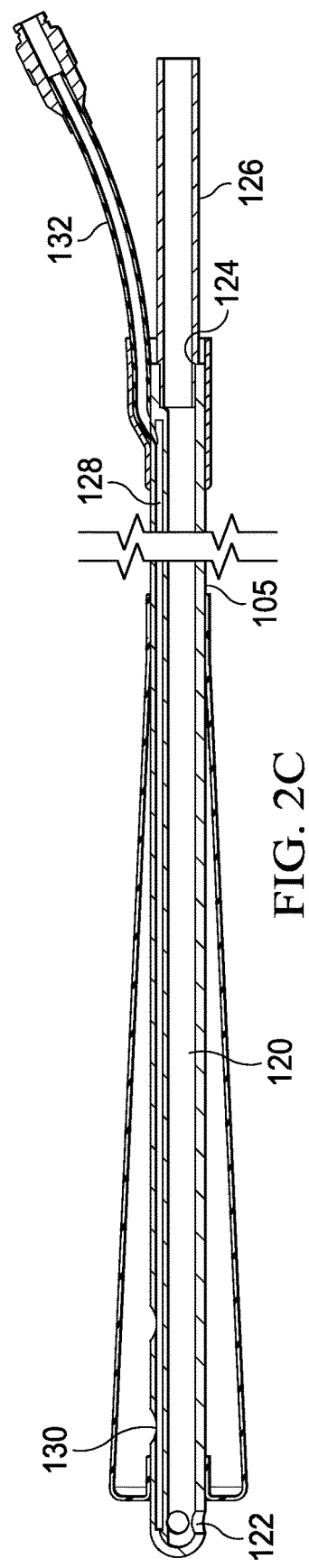
FIG. 2B
FIG. 2C

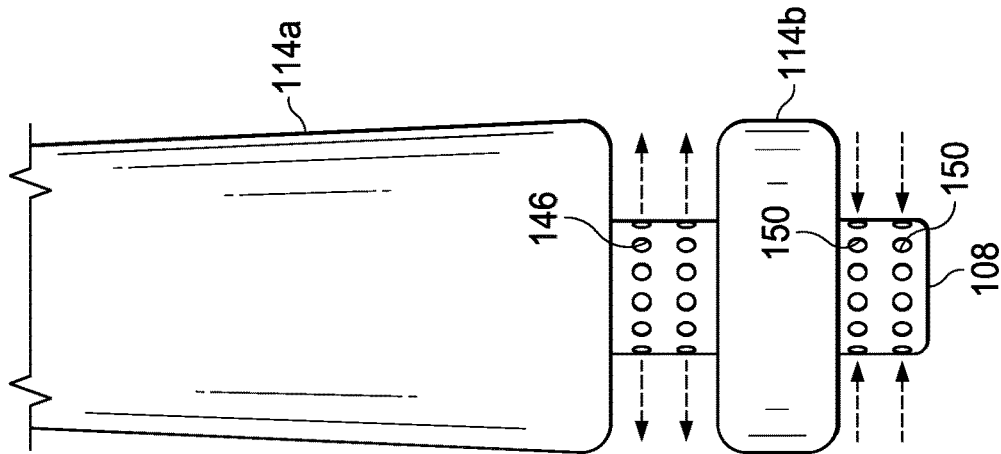
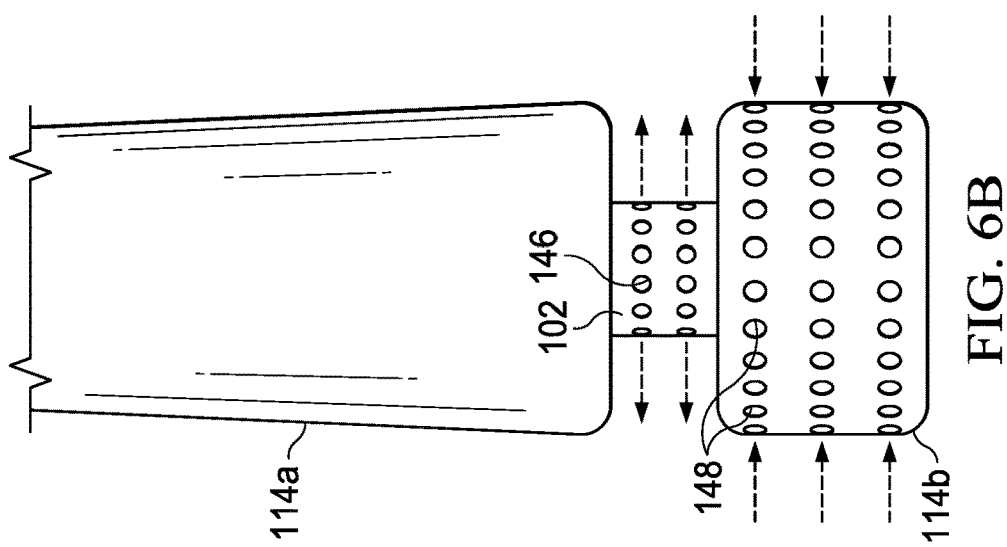
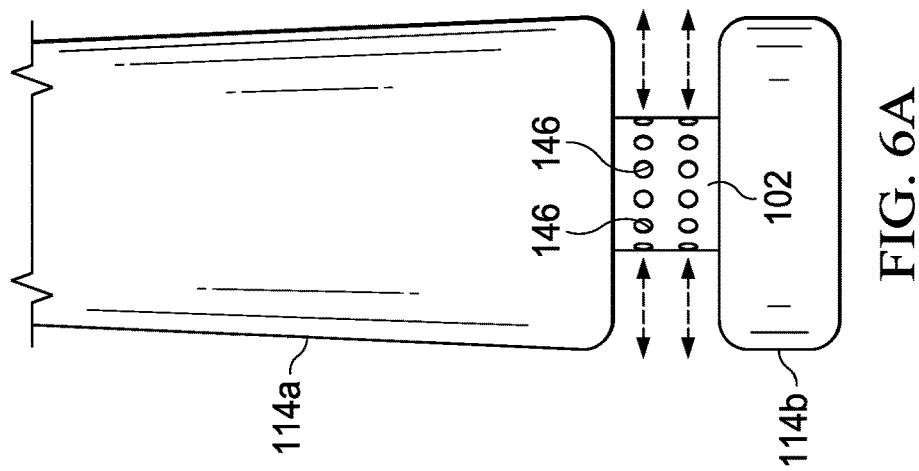

SYSTEMS AND METHODS OF PERFORMING SURGERY USING LAPLACE'S LAW TENSION RETRACTION DURING SURGERY

CROSS REFERENCE TO RELATED APPLICATIONS

This application claims the priority benefit of U.S. Provisional Patent Application No. 62/930,254, filed Nov. 4, 2019, which is hereby incorporated herein by reference in its entirety.

TECHNICAL FIELD

The examples herein may be directed to a sleeve gastrectomy, and more particularly to a bougie or medical tube inserted into the stomach and used in conjunction with a sleeve gastrectomy stapler or clamp. The example devices herein may provide proper tension of the stomach tissue during clamping of the stapler or clamp during the creation of a vertical sleeve gastrectomy.

BACKGROUND

Obesity is a disease that affects a significant portion of the world's population and leads to multiple chronic medical conditions and premature death from cardiovascular events and cancer. In particular, the United States has a current, and worsening obesity epidemic. The U.S. Centers for Disease Control and Prevention (CDC) reports that over 33% of the U.S. population is obese, with a Body Mass Index (BMI) of over 30, and another 35-40% of the US population is overweight, with a BMI of 25-30. The CDC reports that the percent of the US population being either overweight or obese by 2018 will be 75%. The CDC also reports that obesity directly costs the U.S. economy $147 billion currently, and projects that the costs will approach $315 billion by 2020.

Further, obesity has environmental, genetic, and behavioral origins but is intractable to most medical and behavioral interventions. To help reduce obesity and/or facilitate weight loss, bariatric surgery may be an option for some patients that may be overweight. Typically, bariatric surgery may be an effective long-term treatment option for patients with a BMI greater than 35. Despite the 20 million patients who are eligible for weight loss surgery in the U.S., the number of procedures per year has plateaued at about 200 thousand, eliminating any public health effect of surgery.

In recent years, a popular form of bariatric surgery may include a laparoscopic vertical sleeve gastrectomy (e.g., which may remove approximately 80% of the stomach). Laparoscopic vertical sleeve gastrectomy may be a procedure that may be safer and more effective for patients eligible for weight loss surgery. In fact, it has been accepted as the surgery that should be offered to most morbidly obese patients over, for example, laparoscopic adjustable gastric banding and laparoscopic Roux-en-Y gastric bypass. As such, the surgery has been adopted by bariatric surgeons and is now the most commonly performed weight loss surgery.

Vertical sleeve gastrectomy is typically performed using standard laparoscopic equipment. The greater curvature of the stomach is mobilized using vessel-sealing devices, sealing the gastric branches of the gastroepiploic vessels and the short gastric vessels. The posterior adhesions of the stomach are also divided so the stomach is fully mobilized while the blood supply to the lesser curvature remains intact.

Following mobilization of the stomach a calibration tube is typically introduced into the stomach through the mouth. Resection is accomplished by applying a series of staples from a laparoscopic linear surgical stapler, for example, along the calibration tube in a staple line. The staple line may be important in sleeve gastrectomy as the amount of weight lost and complications or consequences may be a direct result of the quality of the resultant sleeve gastrectomy pouch formed from the staple line (e.g., the portion of the stomach not rescinded by the staple line). The complications or consequences may include gastroesophageal reflux disorder (GERD), weight loss failure or weight regain, food intolerance, staple line bleed, leak, and/or the like.

The stomach resection line is long (e.g., up to 22 cm). While the stomach is being stapled, sections of the stomach are retracted. Each section may be, for example, 3 cm in length and requires incorporation of equal amounts of the anterior and posterior sides of the stomach. Stomach tissue can be modelled as a series of ropes or elastic fibers. These must be pulled in the correct traction force vector relative to the clamp or stapler with 4 dimensions or axes of direction (i.e., up/down or anterior/posterior; left/right; caudad/cephalad; and rotation) and 1 dimension of magnitude. Maintaining proper tension during each clamp or staple is important to produce a sleeve gastrectomy pouch (e.g., from the staple line) without negatively affecting or interfering with the natural elasticity of the tissue.

To help produce a repeatable sleeve gastrectomy pouch, a sleeve gastrectomy shaping tube may be used. Unfortunately, the surgeon must still manually manipulate the stomach to apply tension while planning the resection line using existing methods.

SUMMARY

Disclosed are embodiments of an apparatus for performing a sleeve gastrectomy, where the apparatus can include a bougie for insertion into an interior of a stomach, the bougie having a proximal bougie end and a distal bougie end, an inflation lumen having a proximal lumen end and a distal lumen end, the inflation lumen extending from the proximal bougie end through the distal bougie end, a fluid delivery system coupled with the proximal lumen end, the fluid delivery system being operably configured to deliver positive pressure in a predetermined positive pressure range into the stomach, and a monitor coupled with the proximal lumen end operably configured for the monitoring of pressure or volume within the stomach. The bougie can be operably configured to define a resection line for a sleeve gastrectomy when the predetermined positive pressure range is achieved within the stomach.

The bougie can include at least one balloon portion positioned at the distal bougie end. The inflation lumen can be used for both inflation and suction. The fluid delivery system can be a hand pump or a foot pump. The monitor can be a visual indicator or an audible indicator. The monitor can include a control system for metering a fluid delivered through the inflation lumen. The bougie can include at least one sensor coupled with the distal bougie end for monitoring a pressure or volume within the stomach. The distal bougie end can include a shaping portion that can be a balloon or an articulating tip. The distal bougie end can include an overtube. The inflation lumen can be a multi-lumen catheter. The predetermined positive pressure range can be from 15 mmHG to 20 mmHG.

Disclosed are embodiments of an apparatus for performing a sleeve gastrectomy, where the apparatus can include a bougie for insertion into an interior of a stomach, the bougie having a proximal bougie end and a distal bougie end, an inflation lumen having a proximal lumen end and a distal lumen end, the inflation lumen extending from the proximal bougie end through the distal bougie end, a fluid delivery system coupled with the proximal lumen end, the fluid delivery system being operably configured to deliver a predetermined range of positive pressure into the stomach, and a control system coupled with the proximal lumen end for the metering and monitoring of pressure or volume within the stomach. The bougie can be operably configured to cooperate with a stapler or clamp to define a resection line for a sleeve gastrectomy when the predetermined positive pressure range is achieved within the stomach.

Embodiments of a system for performing a sleeve gastrectomy can include a first medical device, the first medical device having a bougie for insertion into an interior of a stomach, the bougie having a proximal bougie end and a distal bougie end, an inflation lumen having a proximal lumen end and a distal lumen end, the inflation lumen extending from the proximal bougie end through the distal bougie end, a pump coupled with the proximal lumen end, the pump being operably configured to deliver a predetermined positive pressure range into the stomach, a monitor coupled with the proximal lumen end for the monitoring of pressure or volume of the stomach, and a shaping portion, the shaping portion being positioned at the distal bougie end, wherein the shaping portion is operably configured to position a portion of the stomach. The system can include a second medical device, the second medical device being a stapler or clamp positioned externally on the stomach laterally adjacent to the first medical device. In the system, the first medical device and the second medical device can be operably configured to define a resection line for a sleeve gastrectomy when the predetermined positive pressure range is achieved within the stomach and the second medical device can be operably configured to clamp the stomach along the resection line.

Example methods for performing a sleeve gastrectomy can include the steps of providing a first medical device including a tube for insertion into an interior of a stomach, the tube having a proximal end and a distal end, the distal end comprising a shaping portion; providing an inflation lumen for the introduction of positive pressure into the stomach; providing a second medical device, the second medical device being a stapler or clamp positioned externally on the stomach laterally adjacent to the first medical device; introducing positive pressure into the stomach via the inflation lumen; defining a resection line for a sleeve gastrectomy, wherein the resection line is defined at least partially by the position of the second medical device relative to the first medical device when a predetermined positive pressure range is provided via the inflation lumen; and clamping the stomach using the second medical device along the resection line.

Methods can include a bougie including the inflation lumen. The first medical device can comprise a bougie having a first balloon portion, the first balloon portion having a first balloon inflation lumen. The first balloon portion can be a non-compliant balloon having a predetermined shape in an inflated configuration. Methods can include an indicator associated with the predetermined positive pressure range of the stomach being achieved. The indicator can be a visual or audible indicator signaling that a positive pressure within the stomach is below the predetermined positive pressure range, above the predetermined positive pressure range, or within the predetermined positive pressure range. The predetermined positive pressure range can be from 1 mmHG to 25 mmHG. The predetermined positive pressure range can be from 15 mmHg to 20 mmHg. The method can include providing a release for when a pressure within the stomach is greater than the predetermined positive pressure range. The first medical device can include a suction portion and an inflation portion, where the suction portion is operably configured to urge a first portion of the stomach proximate the suction portion and the inflation portion is operably configured to inflate the stomach to the predetermined positive pressure range. The suction portion can be positioned proximate the GE junction of the stomach. The suction portion can be positioned proximate the antrum of the stomach. The suction portion of the first medical device can extend from a portion proximate the GE junction of the stomach to a portion proximate the antrum of the stomach. The inflation lumen can be selectively configured to provide suction. The distal end of the first medical device can include an articulating member, the articulating member being operably configured to position the antrum relative to the second medical device.

Example methods where defining a resection line comprises applying a first amount of compression to the stomach with the second medical device when the positive pressure is introduced into the stomach, and applying a second amount of compression to the stomach when pressure within the stomach has reached the predetermined positive pressure range, wherein the second amount of compression is greater than the first amount of compression and the second amount of compression is operably configured to immovably retain the stomach. Example methods where the step of clamping includes providing a first clamping force with the second medical device prior to the resection line being defined, and a second clamping force with the second medical device after the resection line is defined to immovably secure the stomach therein. Example methods where the step of clamping includes first clamping a lower portion of the stomach, defining the resection line, and clamping the full length of the stomach using the second medical device. Example methods where the step of clamping the stomach with the second medical device comprises stapling the stomach and resecting a portion of the stomach.

In example methods, the first medical device can comprise a plurality of balloon portions. The distal end of the first medical device can be operably configured to articulate. The first medical device can include at least one sensor to measure the pressure or volume within the stomach. The first medical device or the second medical device include a sensor to measure tension, pressure, or volume of the stomach.

Example methods in accordance with embodiments described herein can include the steps of providing a first medical device including a tube for insertion into an interior of a stomach, the tube having a proximal end, a distal end, and at least one balloon portion, the distal end comprising a shaping portion; providing an inflation lumen for the introduction of positive pressure into the stomach, wherein the inflation lumen is coupled with a pump, a pressure gauge, and a pressure release valve; providing a second medical device, the second medical device being a stapler or clamp positioned externally on the stomach laterally adjacent to the first medical device; introducing positive pressure into the stomach via the inflation lumen until a predetermined range of pressure is achieved; defining a resection line for a sleeve gastrectomy, wherein the resection line is defined at least partially by the position of the second medical device relative to the first medical device when the predetermined positive pressure range is achieved; clamping the stomach using the second medical device along the resection line; stapling the stomach using the second medical device along the resection line; and resecting a portion of the stomach using the second medical device to form a sleeve gastrectomy.

Example methods can include a bougie, the bougie including the inflation lumen. The first medical device can comprise a bougie having at least one balloon portion, the at least one balloon portion having at least one balloon inflation lumen. Example methods can include an indicator for determining when the predetermined positive pressure range of the stomach has being achieved. The indicator can be a visual or audible indicator signaling that a positive pressure within the stomach is below the predetermined threshold range, above the predetermined threshold range, or within the predetermined threshold range. The predetermined positive pressure range can be from 1 mmHG to 25 mmHG. The predetermined positive pressure range can be from 15 mmHg to 20 mmHg.

In example methods, the first medical device can include a suction portion and an inflation portion, where the suction portion is operably configured to urge a first portion of the stomach proximate the suction portion and the inflation portion is operably configured to inflate the stomach to the predetermined positive pressure range. The suction portion can be positioned proximate the GE junction of the stomach, proximate the antrum of the stomach, or can extend from a portion proximate the GE junction of the stomach to a portion proximate the antrum of the stomach. The inflation lumen can be selectively configured to provide suction. The distal end of the first medical device can include an articulating member, the articulating member being operably configured to position the antrum relative to the second medical device. The first medical device can include at least one sensor to measure pressure or volume within the stomach.

BRIEF DESCRIPTION OF THE DRAWINGS

The present disclosure will be more readily understood from a detailed description of some example embodiments taken in conjunction with the following figures:

FIG. 2B depicts an elevation view of the first medical device of the system of FIG. 1.

FIG. 2C depicts a cross-sectional view of the first medical device of FIG. 2A taken along section 2C-2C.

FIG. 6A depicts an elevation view of a distal portion of a first medical device capable of applying suction according to an embodiment.

FIG. 6B depicts an elevation view of a distal portion of a first medical device capable of applying suction according to another embodiment.

FIG. 6C depicts an elevation view of a distal portion of a first medical device capable of applying suction according to another embodiment.

DETAILED DESCRIPTION

Various non-limiting embodiments of the present disclosure will now be described to provide an overall understanding of the principles of the structure, function, and use of the apparatuses, systems, methods, and processes disclosed herein. One or more examples of these non-limiting embodiments are illustrated in the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment," or "in an embodiment" in places throughout the specification are not necessarily all referring to the same embodiment. Furthermore, the particular features, structures or characteristics may be combined in any suitable manner in one or more embodiments.

Figure 1:
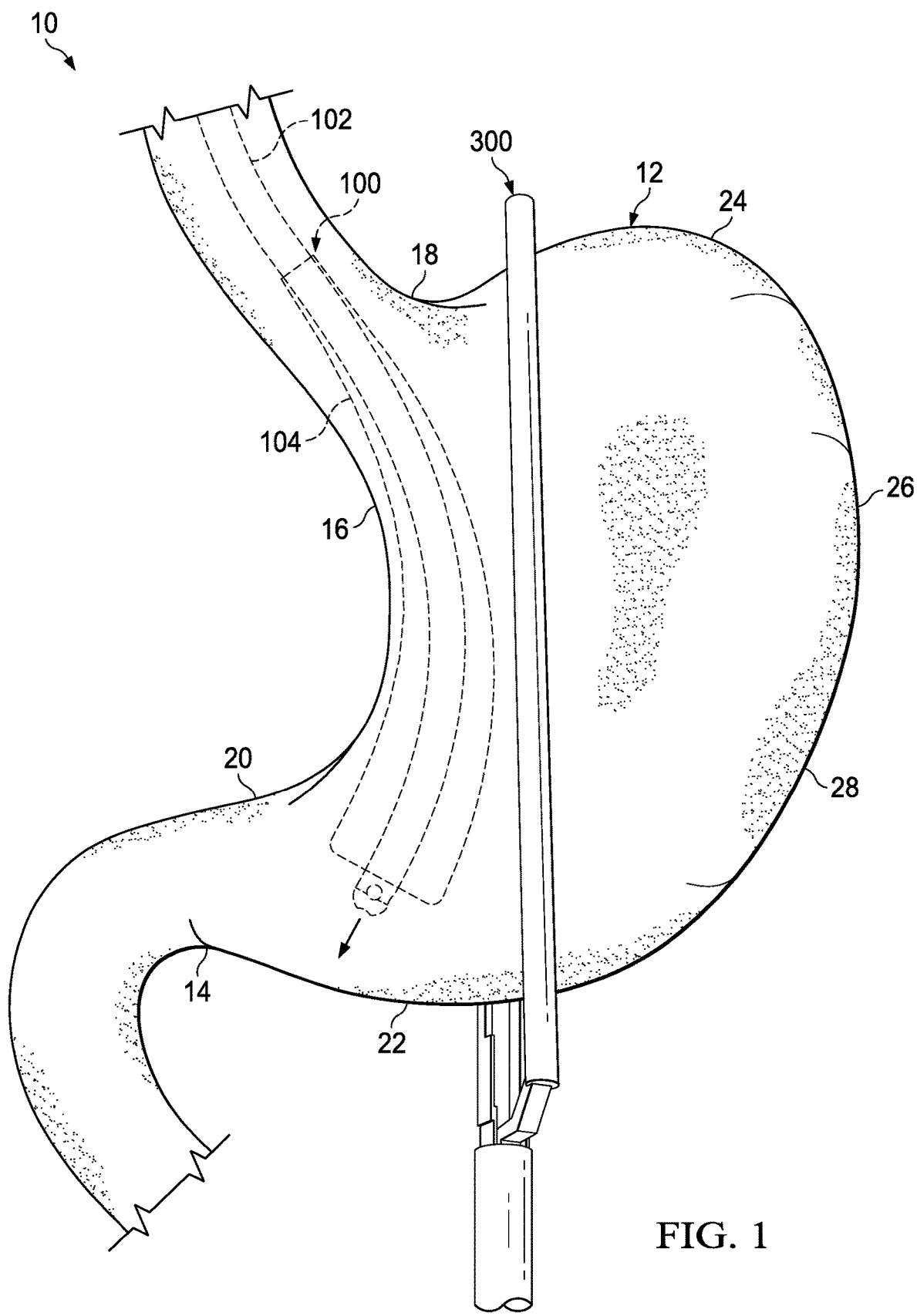
FIG. 1 depicts a perspective view of a system according to an embodiment, the system including a first medical device and a second medical device positioned relative to a stomach.

As described herein, systems and/or methods may be provided for performing a sleeve gastrectomy without disturbing the natural tension lines of the stomach tissue. Additionally, the systems and/or methods described herein may allow for proper sizing of the resulting sleeve gastrectomy pouch. Referring to FIG. 1, some embodiments include a system 10 including a first medical device 100, such as a bougie, and a second medical device 300, such as a clamp or stapler. According to an example herein, the first and second medical devices 100, 300 may be used to perform a vertical sleeve gastrectomy. The sleeve gastrectomy (e.g., resection of part of the stomach) may be performed along a path, such as a resection line, to produce a resultant sleeve gastrectomy pouch ("sleeve") of the stomach 12. For example, a first medical device 100 may be positioned in an interior of the stomach 12. The first medical device 100 may include or have a first diameter along a first portion thereof (e.g., a bougie or tube, such as an orogastric tube) and a second diameter that may be larger than the first diameter along a second portion thereof (e.g., a shaping portion, an inflated portion, or a radially-outward projecting portion). The first medical device 100 may be positioned, for example, by inserting the first medical device into a mouth of a patient to access the interior of the stomach 12 and positioning the second portion at a landmark of the stomach 12, as discussed further below. The second medical device 300 may be positioned on an exterior of the stomach 12 relative to or based on an interaction with the first medical device 100 (e.g., adjacent to, near, in proximity to, and/or interaction with the second portion of the first medical device) such that the second medical device 300 may be configured to demonstrate or create a path such as a resection line or staple line) along the stomach 12 at which the sleeve gastrectomy may be performed. Positive pressure may be introduced to the lumen of the stomach 12, which is used to generate tension on the stomach wall according to the Law of Laplace (T=P*R where T=tension, P=pressure, R=radius). The tension may be uniform in the anterior/posterior plane (e.g., across a transverse cross-section of the stomach), although the tension would vary along the length of the stomach as the radius varies. The Law of Laplace governs how a balloon inflates. The second medical device 300 may be clamped partially or wholly while the stomach 12 is inflated.

Although some examples herein describe the second medical device 300 as a stapler, the disclosure is not so limited. For example, the second medical device 300 may be a clamp, such as a full length 23 cm clamp configured to extend the full length of the stomach. The second medical device 300 may include a first jaw 302 or first clamp member and a second jaw 304 or second clamp member. The anatomical structure has a first side and a second side. In an embodiment, the first jaw 302 may have a first end, a second end and a cartridge housing a plurality of staples, the cartridge having a cartridge face that may be positionable on the first side of the stomach, and the second jaw 304 may have a first end, a second end, and an anvil having an anvil face that may be positionable on the second side of the stomach. The second medical device may include an end effector (e.g., including the jaws 302, 304) having a distal end 306 and a proximal end 308. Examples of suitable second medical devices are disclosed in U.S. Pat. Nos. 9,936,953, 10,278,707, and 10,548,597, each of which is hereby incorporated herein by reference in its entirety.

Figure 2A:
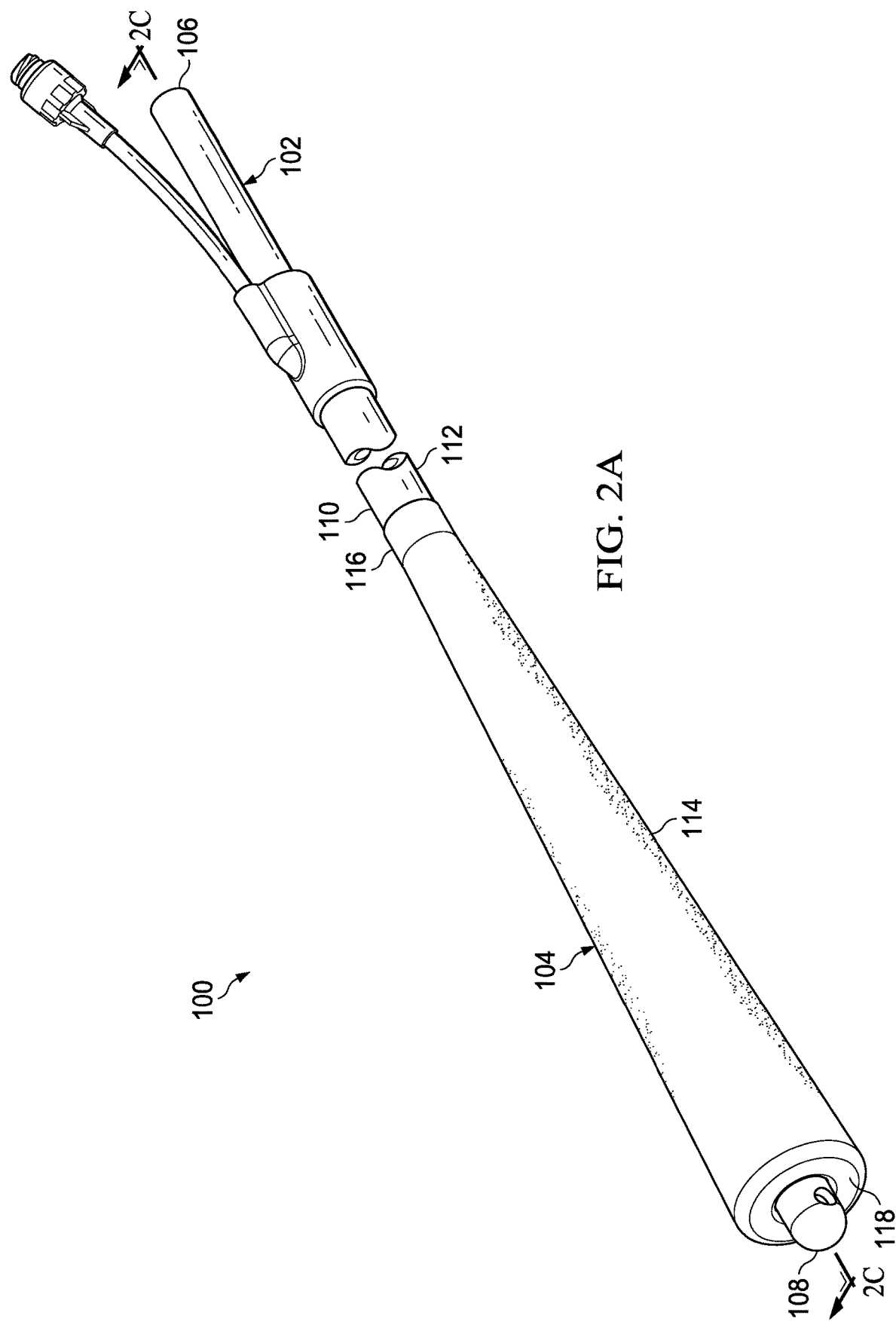
FIG. 2A depicts a perspective view of the first medical device of the system of FIG. 1.

The first medical device 100 may be a shaping bougie, catheter, or tube, such as an orogastric tube. With reference to FIGS. 2A-2C, the first medical device 100 includes a tube portion 102 and a shaping portion 104. The tube portion 102 may be generally cylindrical in shape and may be made of, for example, rubber, silicone, polyurethane, a plastic polymer, and/or any other suitable material. In an embodiment, the diameter of the tube portion 102 is constant. In another embodiment, the diameter of the tube portion 102 varies.

The tube portion 102 may be hollow, solid, define multiple internal lumen and/or the like in one or more examples. The tube portion 102 may comprise a body 105 including a proximal end 106 that may be closer to a surgeon or other user to a distal end 108 that may be farther away from the surgeon. A section of the tube portion 102, ending at the distal end 108, or the distal bougie end, may be long enough to allow for easy insertion into the mouth, esophagus, and stomach, and/or may enable or allow the distal end 108 to be navigated down towards the pylorus 14 of the stomach. The first medical device 100 may include an intragastric section 110 that, when in use, is positioned in the stomach 12 adjacent the lesser curvature 16. The intragastric section 110 may include a proximal end 112 (i.e., distal of the proximal end 106 of the tube portion 102). The location of the proximal end 112 may not be fixed along the length of the tube portion 102. The distal end 108 of the tube portion 102 may also be the distal end of the intragastric section 110. In some embodiments, the first medical device 100 may include lights or other visualization features to improve the use of the first medical device 100 as a guide (e.g., to aid with visualization through the stomach wall). The size of the tube portion may be, in various examples, in a range of 16 French (Fr) to 40 Fr, 16 Fr to 20 Fr, or 32 Fr to 40 Fr. Examples of a suitable tube portion 102 is a 18 Fr bougie, a 34 Fr bougie, or a 38 Fr bougie.

Still referring to FIGS. 2A-2C, in an embodiment, the shaping portion 104 may comprise, for example, one or more inflatable balloons 114 or collapsible portions. In various embodiments, the shaping portion 104 may be adjustable between a first state having a first average diameter and a second state having a second average diameter. Where embodiments discussed herein refer to a balloon that may have an inflated or deflated state, the balloon may be interchangeable with a collapsible portion that may have an expanded or retracted state. The balloon 114 may be relaxed or deflated prior to use and insertion of the first medical device 100 in the stomach. In such an example (e.g., prior to insertion and use), the tube portion 102 and the balloon 114 in the relaxed or deflated state may have a substantially constant diameter. The balloon 114 may be inflated to an inflated state after insertion of the first medical device 100 into the stomach to the appropriate position. For example, a proximal end 116 of the shaping portion 104 may be positioned adjacent to the GE junction 18 or the incisura angularis (IA) 20. The distal end 118 of the shaping portion 104 may be, for example, positioned adjacent to the antrum 22. According to an example, the balloon 114 in the inflated state may have the second average diameter. In some embodiments, when the shaping portion 104 is inflated or expanded, the diameter of the shaping portion 104 may vary along the length. For example, the inflated diameter at the distal end 118 of the shaping portion 104 may be greater than the diameter at the proximal end 116. The size of the inflated or expanded shaping portion 104 may, in an embodiment, be determined based on the desired size of the resulting sleeve. An example of a suitable shaping portion 104 is a balloon with a maximum diameter of 2.5 cm. In another example, the maximum diameter of the shaping portion 104 may be about 3.2 cm. In an embodiment, the area of the shaping portion 104 configured to have the maximum diameter may be located adjacent the distal end 108 of the tube portion 102. For example, the area of the shaping portion 104 configured to have the maximum diameter may be located about 20 mm or less from the distal end 108 of the tube portion 102. The minimum diameter of the shaping portion may be, in an embodiment, about the diameter of the tube portion 102 (e.g., slightly larger than the tube portion 102 diameter to allow the shaping portion 104 to extend around the tube portion 102). In an example embodiment, the tube portion 102 is a 34 Fr catheter, and the shaping portion 104 includes a tapered balloon 114 having a minimum diameter at the proximal end 116 of slightly greater than the diameter of the 34 Fr catheter, which increases along a length of 21 cm to the distal end 118 where the maximum diameter is 3.2 cm. The length of the shaping portion 104 may vary. In an embodiment, the length of the shaping portion 104 may be in a range of about 4 cm to about 21 cm, 15 cm to 20 cm, or about 21 cm.

The shaping portion 104, in combination with positive pressure in the stomach lumen, may enable the stomach tissue to have a proper and uniform tension applied to the stomach wall when the second medical device 300 is clamped to the stomach. The tension may be uniform or symmetric around a diameter (e.g., a transverse cross-section) of the resultant sleeve. For example, the first medical device 100 may be placed with the balloon 114 adjacent the incisura angularis 20 in the deflated state. The second medical device 300 may then be placed in apposition but not fully clamped, the balloon 114, which may be compliant or non-compliant, may be inflated to the inflated state. The stomach lumen is also inflated, as described further below, which creates uniform tension in the stomach tissue of the intended sleeve prior to clamping. Once the desired tension is reached, at a pressure of 20 mmHG for example, the second medical device 300 is clamped. After clamping, the balloon 114 may be deflated such that the first medical device 100 may be removed before or after stapling. In some embodiments, the cross-sectional area of the IA 20 in the resulting sleeve may be maintained or increased in comparison with a sleeve formed by prior methods that may cause a narrowing in the cross-sectional area of the IA 20.

According to one embodiment, the shaping portion 104 may be integrally formed as a unitary monolithic structure as part of the tube portion 102, for example, during manufacturing. In additional or alternative examples, the shaping portion 104 may be separately coupled and/or fixedly attached to the tube portion 102 and/or may include multiple separate pieces. The shaping portion 104 may be unitary or may be segmented. In various embodiments, the one or more balloons 114 can be compliant, semi-compliant, noncompliant, or combinations thereof. If the shaping portion 104 is segmented, each segment may vary in shape and size.

In use, the shaping portion 104 may be placed relative to one or more desired anatomic landmarks. The desired landmark may vary based on the type of first medical device or application. Examples of desired landmarks include the incisura angularis 20, the pylorus 14, and the gastroesophageal (GE) junction 18. The shape of the shaping portion 104 may vary based on the desired landmark. In various embodiments, the shaping portion 104 may be a cylinder positioned at the incisura angularis 20, a frustrum positioned at the pylorus 14, or a long cone or teardrop shape that can be considered a sleeve mold, although the shapes are not so limited.

In an embodiment, the system may include one or more fluid circuits, such as a fluid delivery system, to provide positive pressure to the shaping portion and/or the stomach lumen. One or both of the tube portion 102 and the shaping portion 104 may be coupled to a fluid source such as a foot pump or hand pump. For example, the tube portion 102 may define a lumen 120 extending between a distal aperture 122 or distal lumen end and a proximal aperture 124 or proximal lumen end. When in use, the distal aperture 122 may open into the stomach lumen, and the proximal aperture 124 may be coupled to a fluid source (e.g., via a connecting tube 126). The tube portion 102 may also define a lumen 128 fluidically coupling the interior of the balloon 114 (e.g., via an aperture 130) and a fluid source (e.g., via a coupling 132). The fluid may be a gas (e.g., ambient air, central air, $CO_2$, or nitrogen) or a liquid (e.g., an aqueous solution, such as saline, or water). Where the tube portion 102 and the shaping portion 104 are coupled to separate fluid sources, the fluid sources may be the same or different. As described below, components other than the first medical device 100 may be coupled to a fluid circuit.

Figure 3:
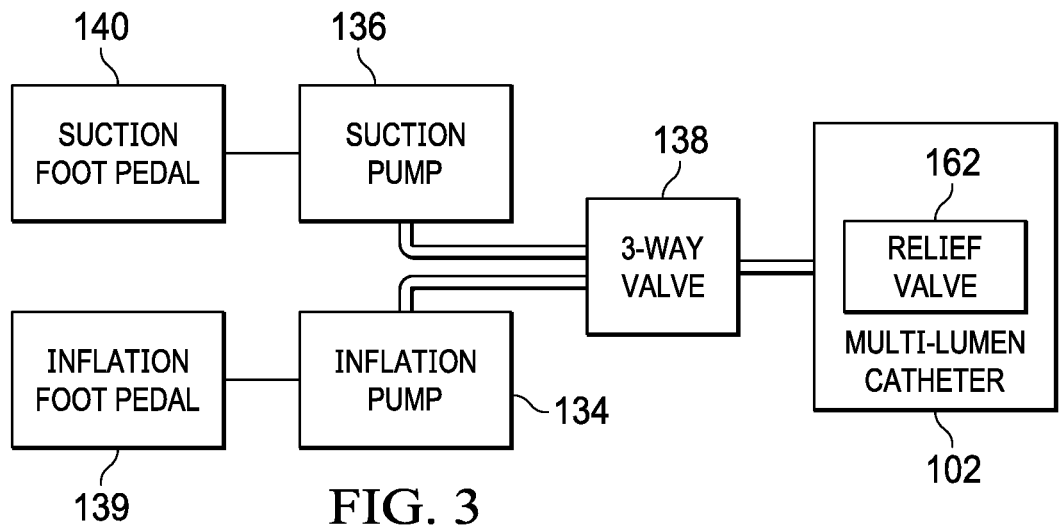
FIG. 3 is a flow chart depicting a fluid delivery system according to an embodiment.
Figure 4A:
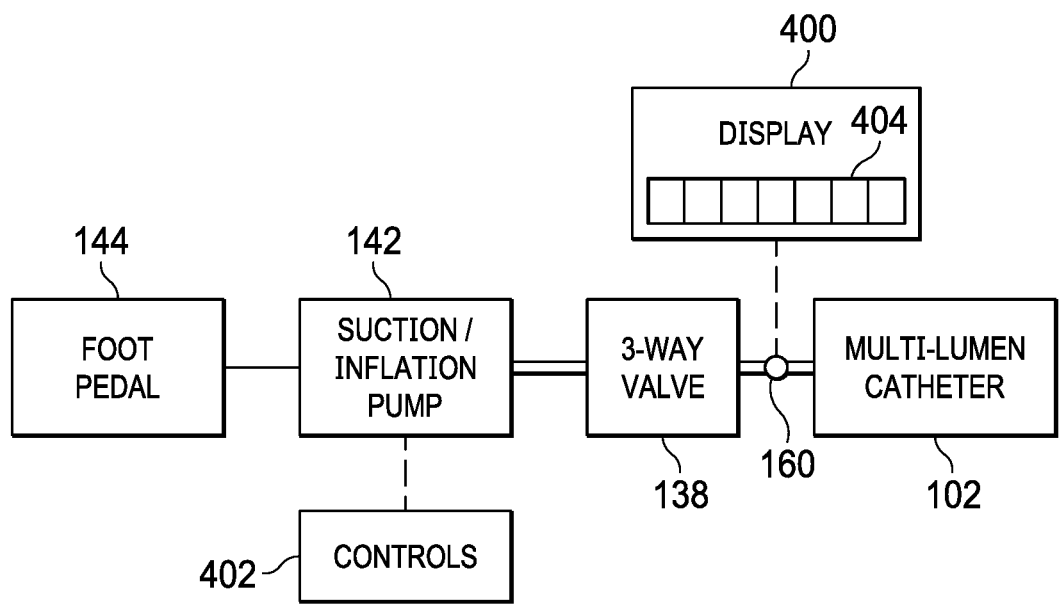
FIG. 4A is a flow chart depicting a fluid delivery system according to another embodiment.
Figure 4B:
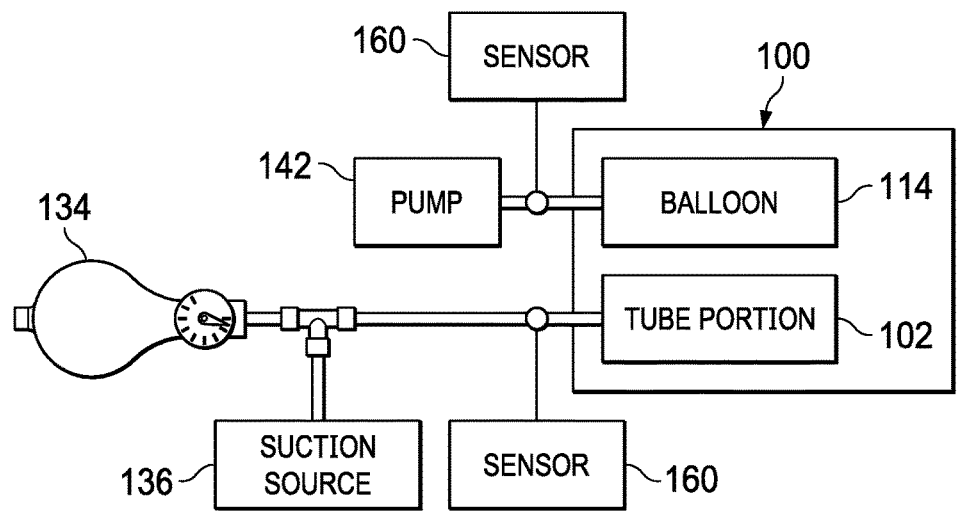
FIG. 4B is a flow chart depicting a fluid delivery system according to another embodiment.
Figure 4C:
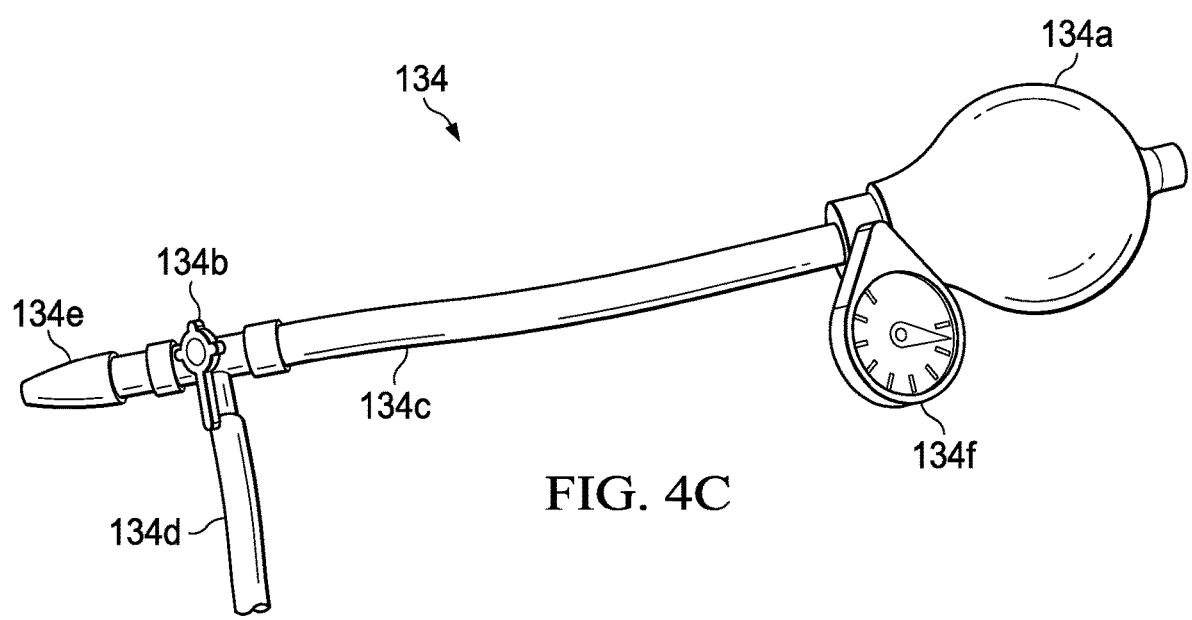
FIG. 4C depicts a perspective view of a hand pump according to an embodiment.

In various embodiments, the one or more fluid circuits or fluid delivery systems may be coupled to a pump system. For example, the tube portion 102, the shaping portion 104, and/or a separate catheter in communication with the stomach lumen can be coupled with a pneumatic pump to provide positive pressure and/or suction. For example, as shown in FIG. 3, a system including a multi-lumen catheter (e.g., the tube portion 102) is coupled to an inflation pump 134 and a suction pump 136 through a three-way valve 138. The pumps 134, 136 may be controllable by mechanical means, such as an inflation foot pedal 139 and a suction foot pedal 140. The pump may also be configured to control suction. Suitable pumps include, without limitation, a foot pump, a hand pump, an electric motor pump, or a combination thereof. A mechanical foot pump may include, for example, a bellows and one or more pedals. A hand pump may include a stopcock that may be turned after clamping. A motorized pump may include switches or pedals for positive pressure or suction. In an example, the pump system may include a pump configured to apply both inflation and suction. As shown in FIG. 4A, a system including a multi-lumen catheter (e.g., the tube portion 102) is coupled to a pump 142 through a three-way valve 138. The three-way valve 138 may be a part of the pump 142 or a separate component. The pump 142 may be controllable by mechanical means, such as a foot pedal 144. Although one pedal 144 is shown and may be configured to control both suction and inflation, more than one may be included. FIG. 4B illustrates an embodiment including a first and second fluid delivery system. The first fluid delivery system is coupled to the tube portion (e.g., lumen 120) including a sensor 160, a hand pump 134 (see FIG. 4C), and a sensor 160. The second fluid delivery system includes an inflation/suction pump 142 and a sensor 160 coupled to the balloon 114 of the shaping portion. FIG. 4C depicts an example hand pump 134 including a bulb 134a coupled to a 2-way stopcock 134b via tubing 134c. The 2-way stopcock 134b is also coupled to an adapter 134d to be connected to a suction source and an adapter 134e to be coupled to the first medical device 100. The hand pump 134 may also include a pressure gauge 134f. Alternative to pedals, in an embodiment, buttons may be incorporated into the second medical device 300 to inflate and deflate the stomach, as discussed further below.

The pump 142 can be associated with a monitor or control system for the monitoring and metering of the fluid to be delivered such that the stomach is not overinflated. The monitor can include a visual or audible indicator of when the stomach pressure or stomach volume if, for example, above a desirable predetermined range, below a predetermined range, or within the predetermined range. The monitor or control system can include a release valve set at a pressure above the desirable predetermined range to offgas fluid to return the stomach volume or pressure to an acceptable range. The control system may include any suitable features to provide a constant volume or pressure within the stomach, which may differ from prior techniques that insufflate the stomach to test for leaks and the like. Prior insufflation testing methods may use relatively high pressures, such as above 25 mmHg, to test for leaks without the need to meter or maintain such a pressure within a defined range. Such pressures in insufflation test applications, which can exceed 50 mmHg to 75 mmHg may be too high for use with the presently described systems. Embodiments described herein can include suitable feedback sensors and the like with the first medical device or bougie to allow the control system to adjust pressure or volume in accordance with embodiments described herein.

In an embodiment, the first medical device may be configured to maintain a higher pressure in the shaping portion 104 than the stomach lumen during the sleeve gastrectomy procedure. The maximum pressure of the shaping portion 104 may be in a range of, for example, 40 mmHg to 70 mmHg. The maximum pressure of the stomach lumen may be, for example, up to 20 mmHg (the physiologic 'pain' pressure of the stomach), in a range of about 20 mmHg to about 100 mmHg, or up to 100 mmHg. If the surgery is being performed laparoscopically, the pneumoperitoneum will need to be accounted for (e.g., 10 mmHg to 20 mmHg). This pressure allows the stomach to inflate but not be unnaturally deformed. Further, the tension provided by the pressure has a direction and magnitude natural to the stomach tissue. The tension relieves the surgeon from the necessity of manipulating the tissue and potentially disrupting the natural tension pattern of the stomach tissue, although the surgeon may still manipulate the tissue manually if desired. The direction of the tension vector is generally at a right angle to the longitudinal axis of the second medical device 300 (e.g., longitudinal axis of the jaws 302, 304), which may provide a better resection line. The pressure used to inflate the shaping portion 104 may vary. In an example, the pressure used to inflate a balloon with water may be about 115 mmHg.

Figure 5A:
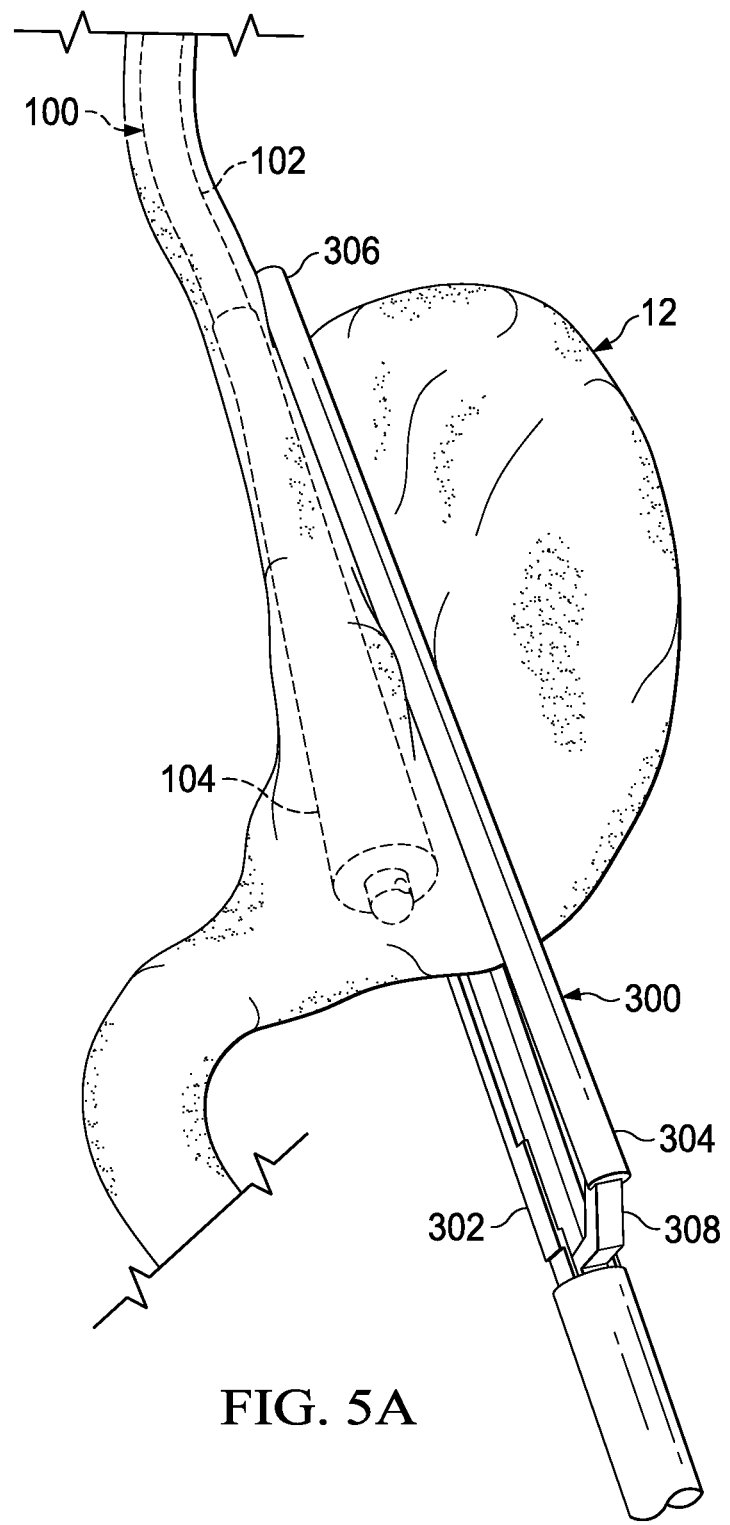
FIG. 5A depicts a perspective view of the system of FIG. 1 where the first medical device is positioned in the stomach lumen and the second medical device is positioned outside the stomach adjacent to the first medical device in an example method of creating a resection path during a sleeve gastrectomy.
Figure 5B:
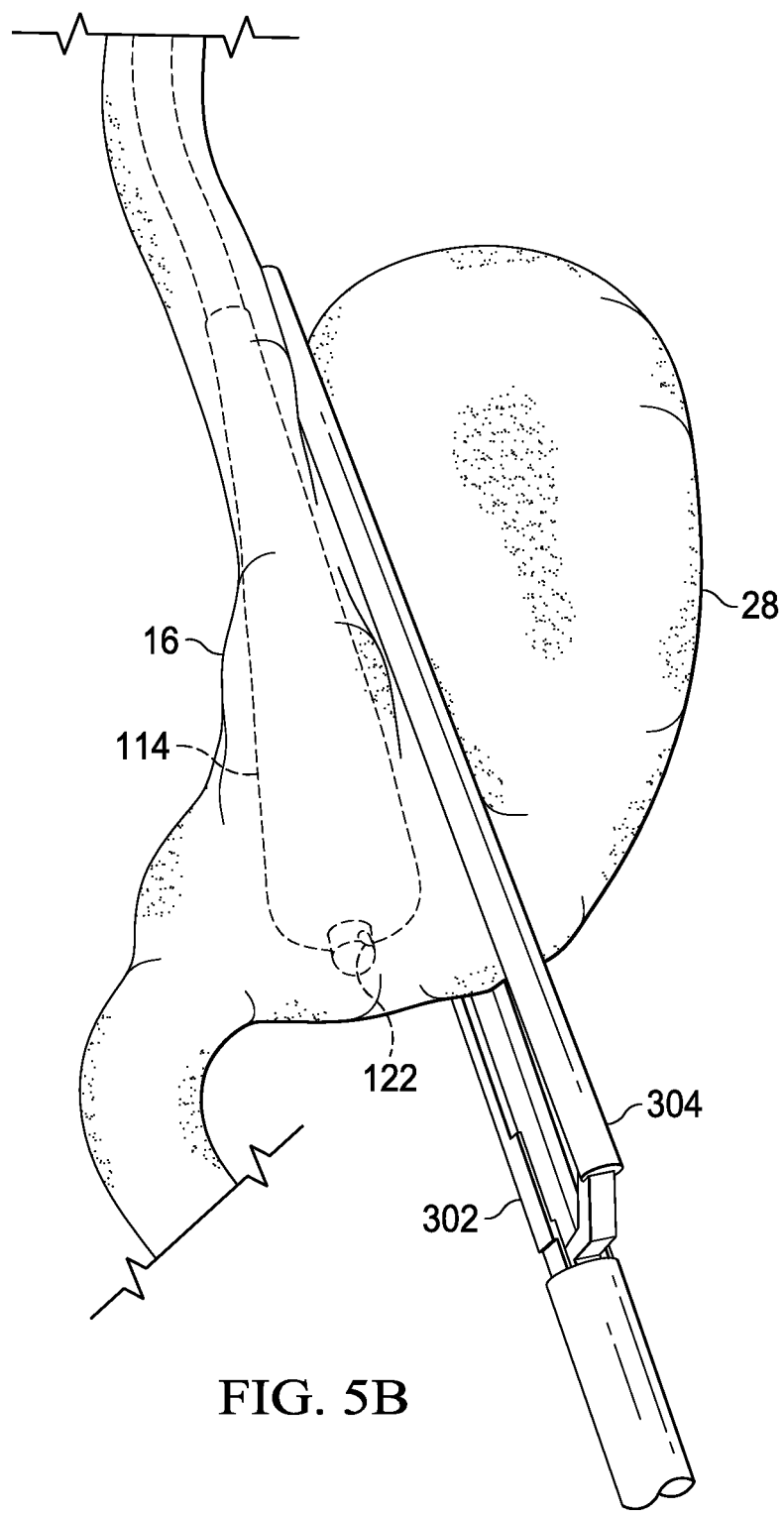
FIG. 5B depicts a perspective view of the system of FIG. 1 where the shaping portion of the first medical device is inflated and the stomach lumen is being pressurized.
Figure 5C:
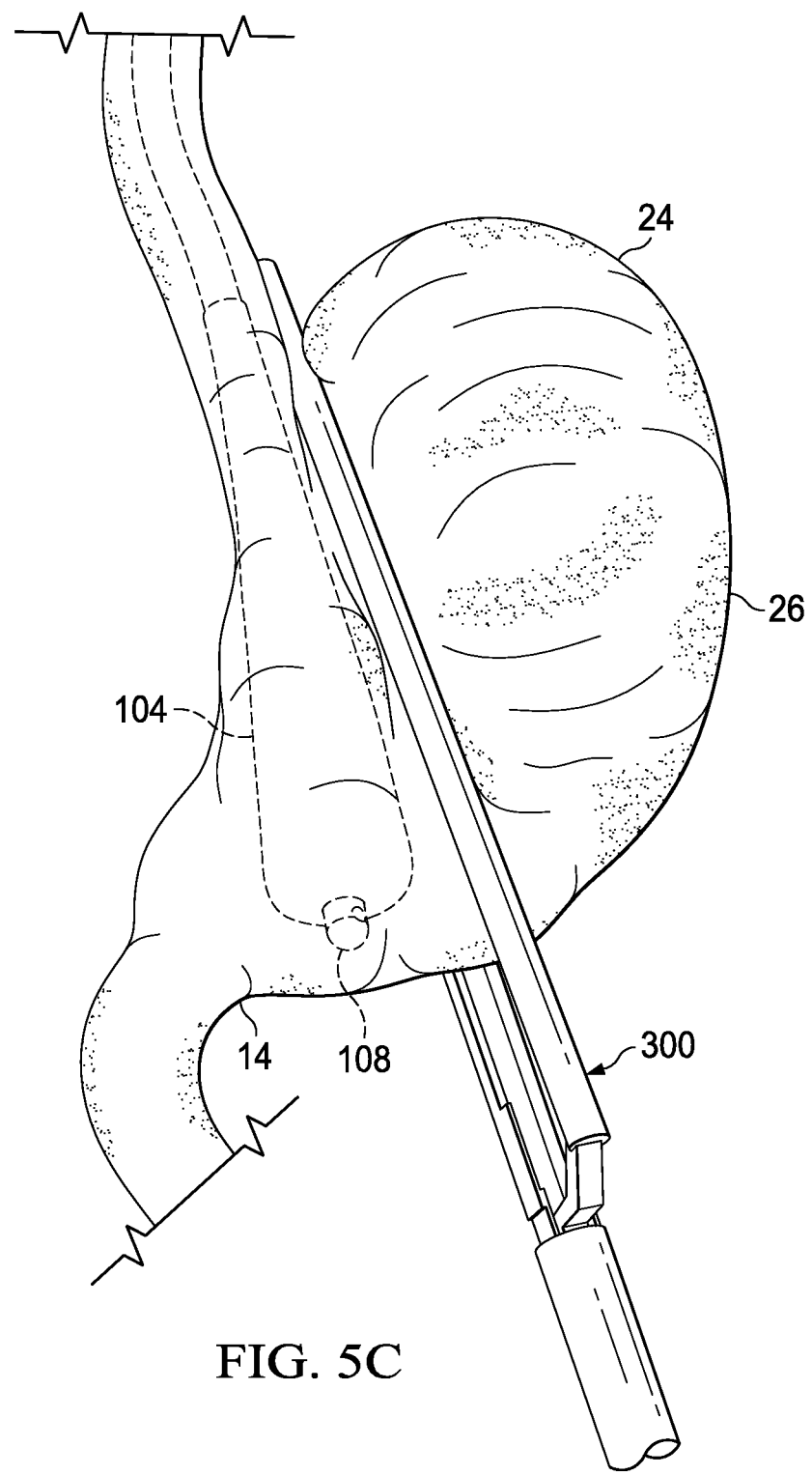
FIG. 5C depicts a perspective view of the system of FIG. 1 where the pressure in the stomach has increased to urge the second medical device against the first medical device.

Referring now to FIGS. 5A-5E, an example method or procedure that may be performed using the first medical device 100 and second medical device 300 is shown. In an example method of creating a sleeve gastrectomy, the first medical device 100 is inserted in a stomach 12. The first medical device 100 is placed along the lesser curvature 16 adjacent to one or more desired anatomic landmarks. Next, a second medical device 300, such as a full-length 23 cm clamp or stapler, is placed across the length of the stomach (FIG. 5A). The lumen 120 is connected to positive pressure. The positive pressure may be applied to begin inflating the stomach (FIG. 5B). The positive pressure generates the most tension in the widest portion of the stomach according to the Law of Laplace (T=PR). The first medical device 100 may also include a shaping portion 104 that is inflated using positive pressure. Methods of controlling and monitoring the positive pressure are described above.

Figure 5D:
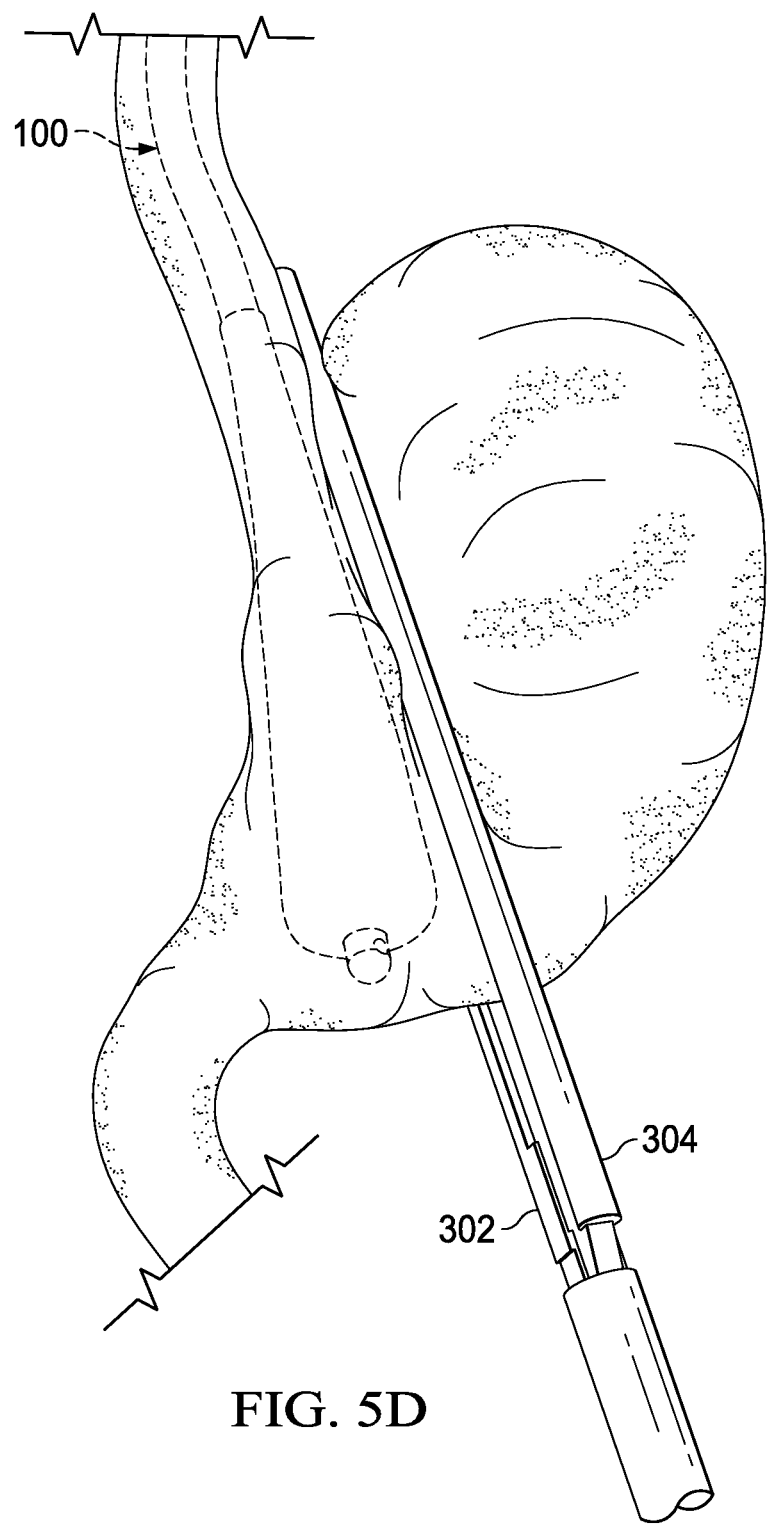
FIG. 5D depicts a perspective view of the system of FIG. 1 where the second medical device has been clamped.
Figure 5E:
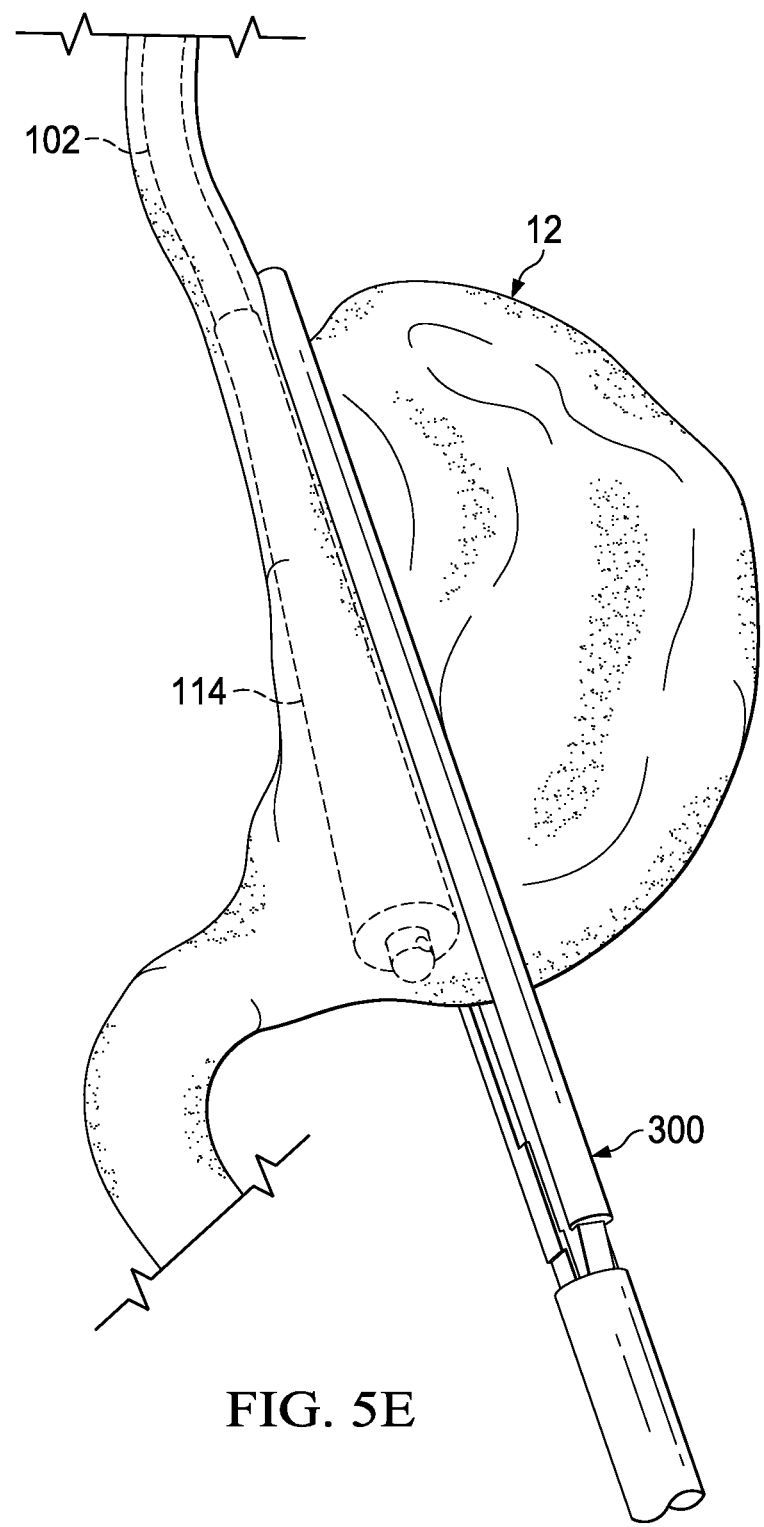
FIG. 5E depicts a perspective view of the system of FIG. 1 where the shaping portion of the first medical device and the stomach lumen have been deflated.

Once more than half of the inflated stomach radius resides lateral to the second medical device 300 (i.e., in a direction away from the first medical device 100), the balloon-like stomach urges the second medical device 300 to become adjacent and snug against the shaping portion 104 of the first medical device 100. As the stomach inflates (FIG. 5C), the growing pressure in the larger portion of the stomach causes the second medical device 300 to move towards the first medical device 100 and pushes the tissue between the first and second medical devices 100, 300 against the shaping portion 104, while uniform tension is applied to the stomach wall. The tissue along the lesser curvature 16 of the stomach may also be drawn towards the shaping portion 104. If too much tissue moves to the remnant side of the stomach due to the increasing pressure, the pressure may be reduced manually or automatically to allow proper sizing of the desired sleeve before clamping. If desired, the surgeon may manipulate the tissue during inflation to control the shape and size of the resulting sleeve. The second medical device 300 may then be partially or fully clamped (FIG. 5D). The stomach lumen may be suctioned (FIG. 5E) before or after fully clamping the second medical device 300. The first medical device 100 may be removed from the stomach after clamping but before stapling. If the stomach is suctioned, positive pressure may be reintroduced to perform a leak test. The stomach may be stapled and cut (i.e., resected) along the resection line defined by the second medical device 300. Embodiments herein may allow for stapling and cutting along a straight resection line while the resulting sleeve is curved along the staple line. While examples herein may describe the second medical device 300 as a full-length stapler, the disclosure is not so limited. In an embodiment, the second medical device is a less-than-full-length stapler. The first activation of the stapler may be done before or after the positive pressure is applied to the stomach lumen. The stapler may then be advanced across the length of the stomach while the stomach is inflated. The first medical device 100 acts as a guide to the surgeon.

Laplace retraction allows for each 'rope' or 'elastic band' of the stomach to be pulled in the correct direction as the positive pressure provides tension along the natural stomach distension vectors, preventing the surgeon from having to manually manipulate the stomach (e.g., using a laparoscopic grasper) in an attempt to create the desired tension. The pressure also pulls every gastric fiber simultaneously, not relying on the segments of tissue that a laparoscopic grasper can grab at one time. Additionally, if the second medical device 300 was initially positioned over a folded piece of stomach, the positive pressure can flatten out all parts of the stomach, preventing the clamping/stapling of folded stomach. Stapling folded stomach tissue can lead to staple line failure and leak. The resultant sleeve may have, for example, a diameter of 1 to 3 cm near a first landmark (e.g., the IA), 2 to 6 cm near a second landmark (e.g., the size of the antrum measured from the pylorus), and 0 to 2 cm near a third landmark (e.g., measured from the edge of the GE junction notch) of the stomach. In another example, the resultant sleeve may have a diameter of 1 cm to 2 cm at the fundus, a diameter of 2 cm to 3 cm at the body at the incisura angularis, and a diameter of 3 cm to 6 cm at the antrum.

With reference to FIGS. 6A-6C, in various embodiments, the first medical device 100 may be configured to provide suction. The first medical device 100 may include a lumen opening to the outside of the first medical device 100 (e.g., lumen 120). One or more suction apertures may be distributed along the length of the catheter. Alternatively, the lumen may extend through the first medical device 100, and suction openings may be provided at a distal end of the lumen. The first medical device 100 or other component providing suction may include a suction control valve that may be used to regulate when and how suction may be applied. Embodiments may incorporate the serial or simultaneous use of suction and inflation to create a desired sleeve geometry.

With further reference to FIGS. 6A-6C, in some embodiments, the shaping portion 104 may include an area in communication with the stomach lumen configured to allow for inflation or suction between two balloons 114. For example, the shaping portion 104 may include a first balloon 114a and a second balloon 114b separated by a section of the tube portion 102. The shape of the first and second balloons 114a,b may be the same or may be different. In an example embodiment, the first balloon 114a may have a tapered shape (e.g., conical frustum shape) and the second balloon 114b may have, for example, a disc shape. When positioned in the stomach, the first balloon 114a may extend from the GE junction 18 to the IA 20, and the second balloon 114b may be adjacent the antrum 22. The section of the tube portion 102 between the first and second balloons 114a,b may be in communication with the stomach lumen. For example, as shown in FIG. 6A, the section may include suction apertures 146, such as holes, mesh, or other porous features, that allow air to pass in and out of the tube portion 102. The tube portion 102 may have multiple lumens including, in an embodiment, a lumen coupling the holes, mesh, or other porous features with an inflation and/or suction pump (e.g., lumen 120). Referring to FIG. 6B, in an embodiment, one or both of the balloons 114a,b may also include suction apertures 148 and be coupled to a suction pump. Additionally, the section of the tube portion 102 between the first and second balloons 114a,b may also be coupled to a pump capable of applying positive pressure in addition to applying suction. In an embodiment, as shown in FIG. 6C, a section of the tube portion 102 distal of the second balloon 114b may include suction apertures 150. The suction apertures 150 may be independently operable from the suction apertures 146. For example, suction may be applied through the suction apertures 150 while positive pressure is applied through the suction apertures 146 or vice versa.

Still referring to FIGS. 6A-6C, suction may be applied to the section between the first and second balloons when the balloons are in a deflated state, an inflated state, or when the balloons are transitioning between those two states. For example, suction may be applied between the first and second balloons 114a,b to help bring tissue closer to the first and second balloons 114a,b while the stomach lumen is being inflated and the second medical device 300 is being urged by the balloon-like stomach to become snug against the first medical device 100. In another example, suction may be applied between the first and second balloons 114a,b to help deflate the stomach lumen before the second medical device 300 has been clamped or the lumen of the desired sleeve after the second medical device 300 has been clamped.

In some embodiments, an additional catheter or other tube separate from the first medical device 100 is in fluid communication with the stomach lumen. The catheter may provide positive pressure in the stomach lumen. In various embodiments, the catheter may also be configured to provide a suction force. For example, a needle may be inserted into the portion of the stomach to be removed during the gastrectomy procedure ("remnant portion"), where the needle is coupled to a pump capable of suction and/or inflation. A grasper may be used to control the position of the stomach, for example, when a catheter or needle is inserted other than through the esophagus.

Figure 7:
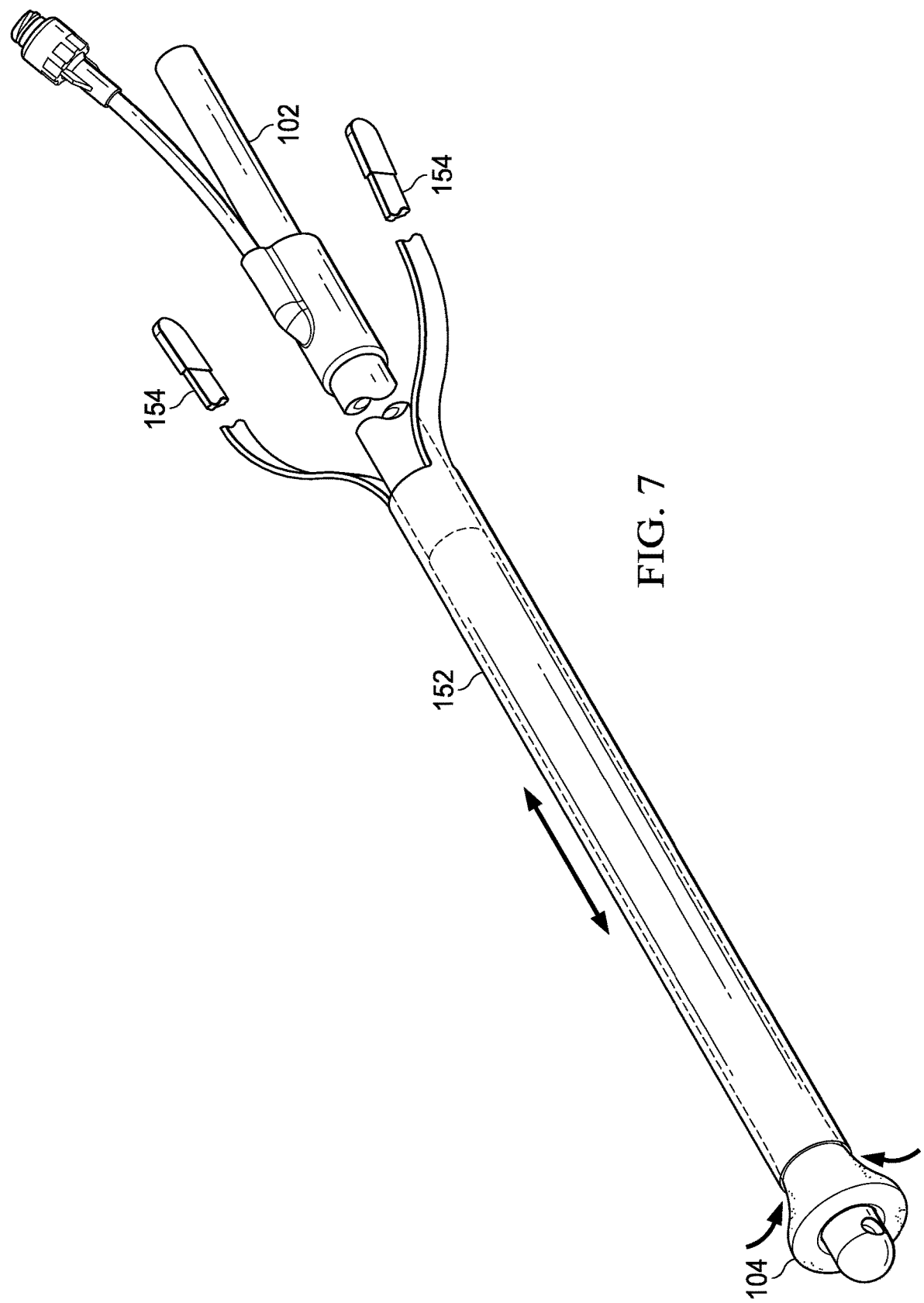
FIG. 7 depicts a perspective view of a first medical device including an overtube in accordance with an embodiment.

Referring now to FIG. 7, in some embodiments, the first medical device 100 may include an overtube 152. The overtube 152 can be more rigid than the shaping portion 104 and may be slid over the exterior of the shaping portion 104. The overtube 152 may be used during insertion of the first medical device 100 into the stomach. In an embodiment, the overtube 152 is flexible enough to act as an introducer sheath. Additionally, in some embodiments, the overtube 152 may optionally include peel-away handles 154 for the surgeon or other user to pull. The handles 154 can be small finger grips, such as those commonly used on transcatheter cardiovascular devices, which allow the overtube 152 to be removed by pulling it back. The peel-away function can allow the overtube 152 to slide back over a catheter bifurcation hub. If the overtube 152 is still positioned on the shaping portion 104 when it is inflated, the overtube 152 can alter the shape and pressure distribution of the shaping portion 104. The overtube 152 may be used to ensure that the stapler is positioned about 1 cm from the GE junction 18 at the top of the resection line.

Figure 8:
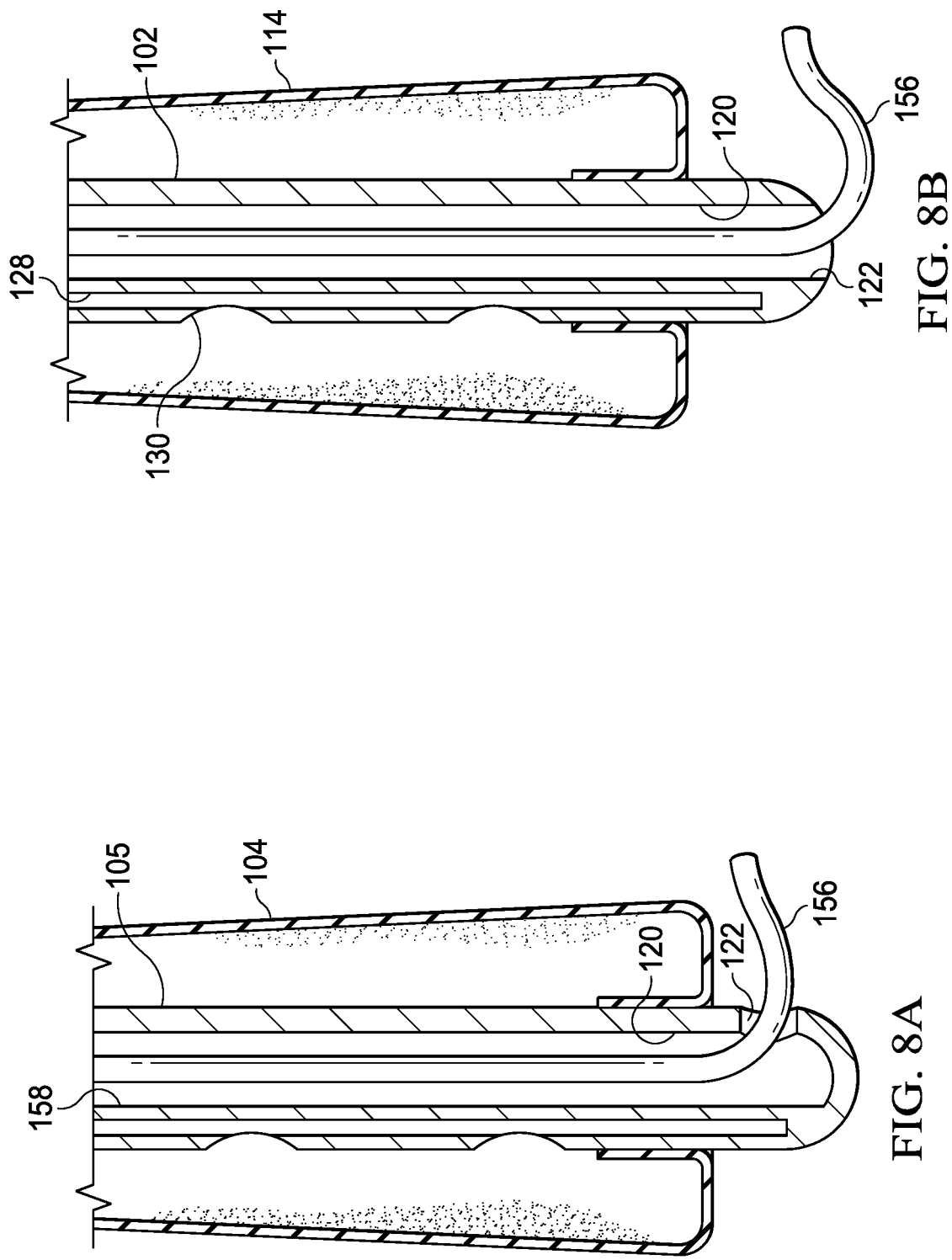
FIG. 8A depicts a cross-sectional view of a first medical device including a gastroscope in according to an embodiment.
FIG. 8B depicts a cross-sectional view of a first medical device including a gastroscope in accordance with another embodiment.

With reference to FIGS. 8A and 8B, in some embodiments, the first medical device 100 is configured to allow another device, such as a gastroscope 156, to pass through the first medical device 100. For example, the gastroscope 156 may extend through the lumen 120 of the first medical device 100 and out of the distal aperture 122 (FIG. 8A). In another embodiment, the first medical device 100 may include a channel 158 extending through a portion or the entirety of the length through which the gastroscope 156 may pass (FIG. 8B). The channel 158 may be coextensive with the lumen 120. Although not shown in FIG. 8B, in an embodiment, the first medical device 100 may include a separate lumen opening to the stomach lumen to control the pressure therein.

In various embodiments, the system may include one or more sensors 160, such as pressure sensors, flow sensors, volume sensors, etc. The sensors may be digital or mechanical. A sensor may be an in-line sensor. A suitable example pressure sensor is a 0-5 psi Omega™ digital pressure transducer (PX26-005GV). The one or more sensors may include a display or may be in communication with a display 400, monitor, or control system, such as one discussed below. For example, mechanical sensors may use a spring or column of fluid to display the measured pressure (e.g., stomach pressure, back-pressure on the inflated shaping portion, suction, etc.). The display may include an indicator to identify whether the measured pressure is low, high, or in an acceptable range. For example, a color-coded range can be used to correlate the measured pressure or volume in the stomach lumen to the desired tension of the stomach tissue.

In various embodiments, any sensor(s) can communicate data via a wireless or wired connection one or more of the first medical device, the second medical device, or a remote device, such as a display. For example, information collected by the sensor(s) can be transmitted using wireless connections (e.g., Bluetooth, Wi-Fi, a cellular network, a satellite, etc.) or wired connections (e.g., cable, copper or fiber optics, etc.).

The system, in some embodiments, may be configured to control or detect a volume of inflation. As discussed above, the system may include a monitor or control system for the monitoring and metering of the fluid to be delivered. The volume of inflation detected and/or controlled may be the volume of the stomach lumen and/or the volume of the shaping portion. Ultimately, the volume of the resultant sleeve may also be controlled. The fluid source may be a syringe or other container with a known volume of fluid. For example, a 60 mL or 100 mL syringe may be used as a fluid source for the inflation of the stomach lumen. The fluid source may be configured to provide an indication of the volume of fluid used to inflate the stomach lumen (e.g., measurements on a syringe or container). In another embodiment, the pump may be used to apply discrete volumes of fluid. A hand pump, for example, may have a known volume of fluid per application (e.g., squeeze). As another example, an electric pump may have a known flow rate, and the system may be configured to detect the volume used based on the time the pump was activated. In some embodiments, a flow meter or flow sensor may be used to measure the flow of fluid into the stomach lumen. Where a compressed fluid (e.g., compressed air) is used as a fluid source, the system may be configured to measure a pressure drop (e.g., with a pressure sensor) in the compressed fluid container to determine the volume of fluid used. The system may also include, in example embodiments, an integrated valve that discontinues fluid flow when a predetermined volume in the stomach lumen is reached. In an embodiment, the integrated valve may be in communication with the controls or a sensor.

In some embodiments, the system will include controls 402 for controlling the inflation and/or suction. For example, one or more of the first medical device 100, the second medical device 300, or a remote device may include controls in wireless or wired communication with the pump system. In an embodiment, the controls 402 can include a monitor or control system for the monitoring and metering of the fluid to be delivered as discussed above. In an embodiment, the second medical device 300 includes switches or buttons to control the inflation and/or suction of the balloon and inflation and/or suction inflation of the stomach lumen. The controls 402 may include, for example, a power button or a "zero" or tare button.

In various embodiments, the system may include a display 400. The display 400 may be configured to show data, such as pressure data relating to the shaping portion and/or the stomach lumen. The display 400 may be on one of the first medical device 100, the second medical device 300, or a separate display device. In an embodiment, the display device may include controls (e.g., controls 402) in wireless or wired communication with the inflation/suction system. The display 400 may also be configured to show data history (e.g., in a graph updating in real-time) or recent changes in the data. In an embodiment, the display device may have a hook or a handle. For example, the display device may be hangable from an IV pole. The display, in some embodiments, may be in communication with a camera and be configured to show the video feed (e.g., from gastroscope 156). In another embodiment, the display device may be a remote device such as a mobile phone or computer. The display 400 may include an indicator 404 to identify whether the measured pressure is low, high, or in an acceptable range. For example, a color-coded range can be used to correlate the measured pressure in the stomach lumen to the desired tension of the stomach tissue. The display 400 may be configured to provide a signal, such as an audio or visual signal. A signal may be provided for various reasons, such as when the tissue tension is at a predetermined value, if there is too much tension, if there is too little tension, etc.

In some embodiments, the relative maximum pressure of the shaping portion and the stomach lumen may be controlled based on the materials, dimensions, resistance, and fluid flow rates of the system. The system can include one or more relief valves 162. Additionally or alternatively, in an example embodiment, the first medical device 100 may include a first relief valve, such as a pop-off or check valve, set at a predetermined maximum pressure of the shaping portion 104. In an embodiment, the first relief valve may be in fluid communication with the lumen of the stomach as well as the lumen of the shaping portion 104. For example, the first relief valve may open into a lumen that opens into the stomach lumen. The first relief valve may vent the excess fluid into the lumen of the stomach. In this configuration, the shaping portion 104 will fill with fluid until the maximum pressure is reached causing additional fluid to vent into the stomach lumen, thus increasing the pressure in the stomach lumen. Due to the first relief valve, the shaping portion 104 maintains a higher pressure than that in the stomach lumen. Further, in some embodiments, the first medical device 100 or other component providing inflation may include a relief valve to prevent over-pressurization of the stomach lumen. The second relief valve may be set to a predetermined maximum pressure of the stomach. The predetermined maximum pressure of the stomach lumen is lower than the predetermined maximum pressure of the shaping portion. A suitable example of a relief valve is a flutter valve (a.k.a. duckbill or Heimlich valve). In some embodiments, a relief valve may provide an indication (e.g., audible or visible) that the predetermined pressure has been reached (e.g., maximum balloon pressure or maximum pressure in the stomach lumen).

In some embodiments, techniques or devices may be used to move more of the antrum to the remnant portion than would otherwise exist due to the positive pressure in the stomach lumen alone. The size of the antrum in the desired sleeve may be actively reduced. In an embodiment, the second medical device may be partially clamped on a bottom part of the stomach (i.e., distal relative to the first medical device, proximal relative to the second medical device). For example, the proximal end of the second medical device may be clamped from the bottom end of the stomach extending upwardly along a portion of the antrum, while the distal end of the second medical device remains unclamped. The shaping portion of the first medical device may be inflated or expanded before the first, partial clamp is made. The location of the partial clamp may be determined based on the desired size of the antrum in the resulting sleeve. The second medical device may be repositioned or angled such that the distal end of the second medical device is near the GE junction. The stomach lumen may be inflated as described above. The second medical device may be urged against the first medical device, and the remainder of the second medical device may then be clamped. Partially clamping the proximal end of the second medical device before inflating the stomach lumen allows for precise control of the size of the antrum in the resulting sleeve.

In another example embodiment, a bottom portion of the stomach may be stapled along the resection line before the stomach lumen is inflated. For example, the bottom end of the stomach extending upwardly along a portion of the antrum may be stapled. The location of the resection line and stapling may be determined based on the desired size of the antrum in the resulting sleeve. The bottom portion of the stomach may be stapled using the second medical device or a separate stapler. The shaping portion of the first medical device may be inflated or expanded before the initial stapling. Afterwards, the second medical device may be positioned or angled such that the distal end of the second medical device is near the GE junction. The stomach lumen may be inflated as described above. The second medical device may be urged against the first medical device, and the remainder of the second medical device may then be clamped. The remainder of the stomach along the resection line may be stapled. Partially stapling the bottom end of the stomach before inflating the stomach lumen allows for precise control of the size of the antrum in the resulting sleeve. Due to the partial stapling at the bottom of the stomach, the resection line may not be a straight line.

Figure 9:
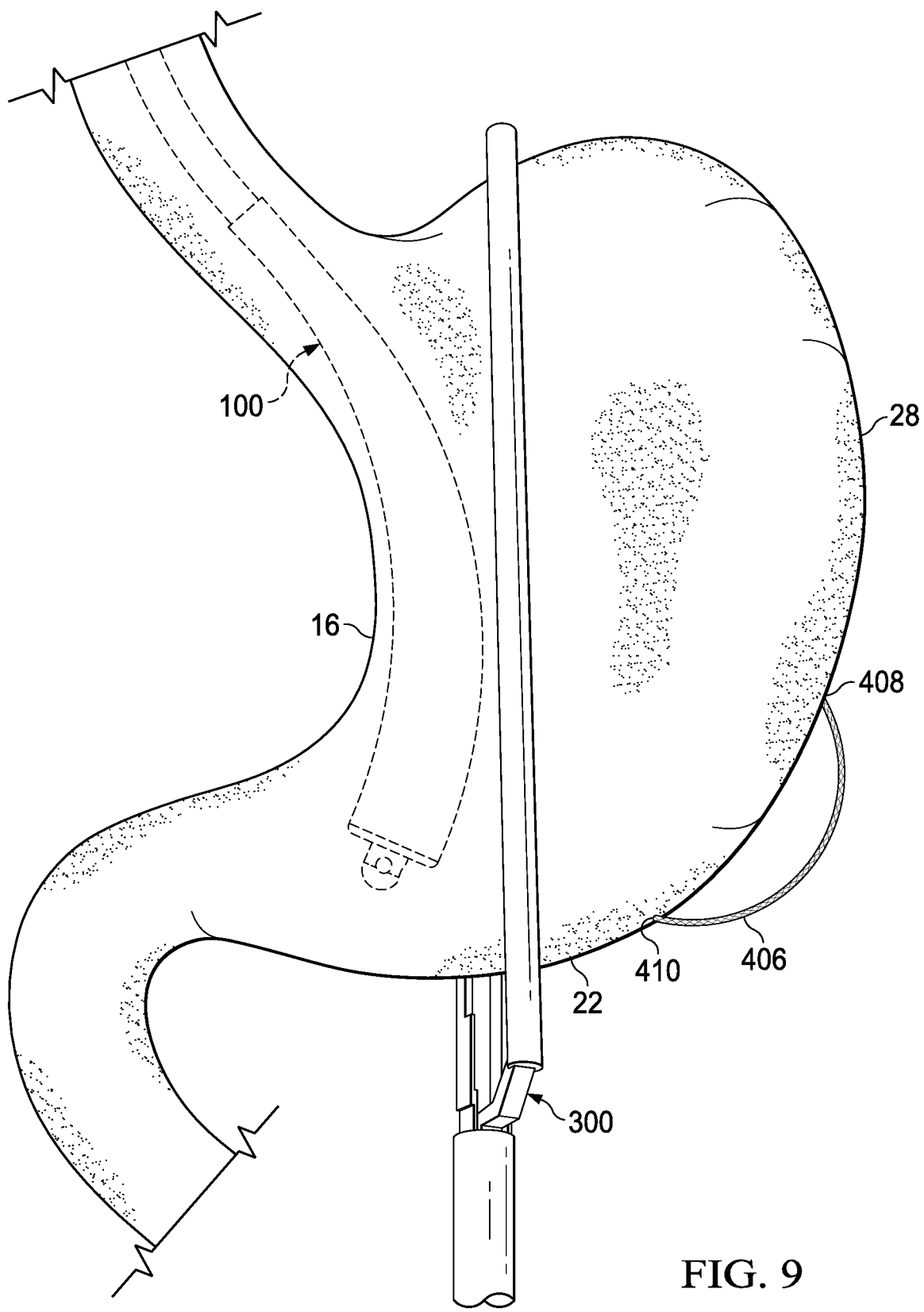
FIG. 9 depicts a perspective view of a system according to an embodiment, the system including a first medical device and a second medical device positioned relative to a stomach, and a connector attached to two sections of the stomach tissue.

With reference to FIG. 9, in some embodiments, a connector 406 may be coupled to two segments of the stomach to pull the antrum through the second medical device 300. For example, a connector 406 may be coupled at one end 408 to a first section of the stomach (e.g., the fundus 24 or body 26 adjacent or along the greater curvature 28) and at the other end 410 to the antrum 22 (e.g., adjacent or along the greater curvature 28). When the stomach inflates, the first section of the stomach will expand further than the antrum due to the increased volume in the first section. As the first section continues to expand, the connector will pull the antrum tissue along with the first section resulting in a smaller portion of the antrum remaining in the desired sleeve (e.g., to the right of the second medical device). The connector can be rigid (e.g., a suture) or a semi-compliant material. For example, the connector 406 can be an elastomeric material or spring element capable of being anchored to the stomach (e.g., with surgical clips or other mechanical means) either integrated into the connector 406 or applied directly to the connector 406. The connector 406 can be implantable or removable; it will be removed with the remnant portion of the stomach.

In various embodiments, the distal end 306 of the second medical device 300 may be initially clamped from the top end of the stomach (e.g., approximately 1 cm from the GE junction) extending downwardly along a portion of the stomach, while the proximal end 308 of the second medical device 300 remains unclamped. The top end of the stomach may be clamped while the shaping portion 104 of the first medical device 100 is inflated or expanded and while the stomach lumen is inflated. The pressure in the stomach lumen may be increased after the top end of the stomach is clamped. In an embodiment, the positive pressure in the stomach lumen may be in a range of about 1 mmHg to about 5 mmHg when the top of the stomach is partially clamped, and the pressure may be increased to be in a range of about 20 mmHg to about 25 mmHg. For example, the pressure after the top end of the stomach is clamped may be increased to about 20 mmHg or about 25 mmHg. The direction of expansion of the stomach will be affected by the partial clamp at the top of the stomach. The antrum 22 will expand further due to the increased pressure causing more of the tissue to move through the second medical device 300 to the remnant side. Once the desired amount of antrum 22 remains in the sleeve, the second medical device 300 may be fully clamped. Partially clamping the distal end 306 of the second medical device 300 before inflating the stomach lumen further allows for precise control of the size of the antrum 22 in the resulting sleeve.

In some embodiments, the proximal end 112 of the intragastric section 110 of the first medical device 100 may be configured to anchor the tissue at the top end of the stomach. For example, the first medical device 100 may be configured to provide suction at or near the proximal end 112. The suction may allow the first medical device 100 to hold the adjacent tissue in place. While the shaping portion 104 of the first medical device 100 is inflated or expanded and while the stomach lumen is inflated, the top end of the stomach may be suctioned to the proximal end 112 of the first medical device 100. In an embodiment, the negative pressure used to hold the stomach tissue in place may be in a range of about 20 mmHg to about 200 mmHg, in a range of about 115 mmHg to about 135 mmHg, or about 125 mmHg. The pressure in the stomach lumen may be increased after the top end of the stomach is anchored in place. In an embodiment, the positive pressure in the stomach lumen may be in a range of about 1 mmHg to about 5 mmHg when the top of the stomach is suctioned, and the pressure may be increased to be in a range of about 20 mmHg to about 25 mmHg. For example, the pressure after the top end of the stomach is suctioned in place may be increased to about 20 mmHg or about 25 mmHg. The direction of expansion of the stomach will be affected by the suction at the top of the stomach. The antrum 22 will expand further due to the increased pressure causing more of the tissue to move through the jaws 302, 304 of the second medical device 300 to the remnant side. Once the desired amount of antrum 22 remains in the sleeve, the second medical device 300 may be clamped, and the suction at the proximal end 112 of the first medical device 100 may be discontinued. Anchoring the top end of the stomach before inflating the stomach lumen further allows for precise control of the size of the antrum 22 in the resulting sleeve. Examples of suction being applied by the first medical device 100 are described herein (e.g., FIGS. 6B, 6C, and 10).

In various embodiments, the stomach may be overinflated such that a portion of the first medical device 100 moves partially through the jaws 302, 304 of the second medical device 300 before the second medical device 300 is clamped. Initially, the second medical device 300 is in an open position, and the stomach lumen is inflated. The pressure in the stomach lumen is increased until the tissue along the lesser curvature 16 of the stomach is tensioned to the point where it pushes at least a portion of the first medical device 100 through the open jaws 302, 304 of the second medical device 300. For example, a middle portion of the intragastric section 110 of the first medical device 100 may move through the jaws 302, 304. The pressure in the stomach lumen is then reduced, allowing the first medical device 100 to return to the right (or the sleeve side) of the second medical device 300. The shaping portion 104 of the first medical device 100 is then inflated or expanded. The pressure in the stomach lumen is increased to urge the second medical device 300 against the first medical device 100, as described above, and then clamped. When the stomach was inflated to the point where the first medical device 100 partially moves through the open jaws 302, 304, tissue from the antrum 22 also moves through the jaws 302, 304 to the remnant side. This process may result in more antrum tissue in the remnant side than would otherwise exist.

Figure 10:
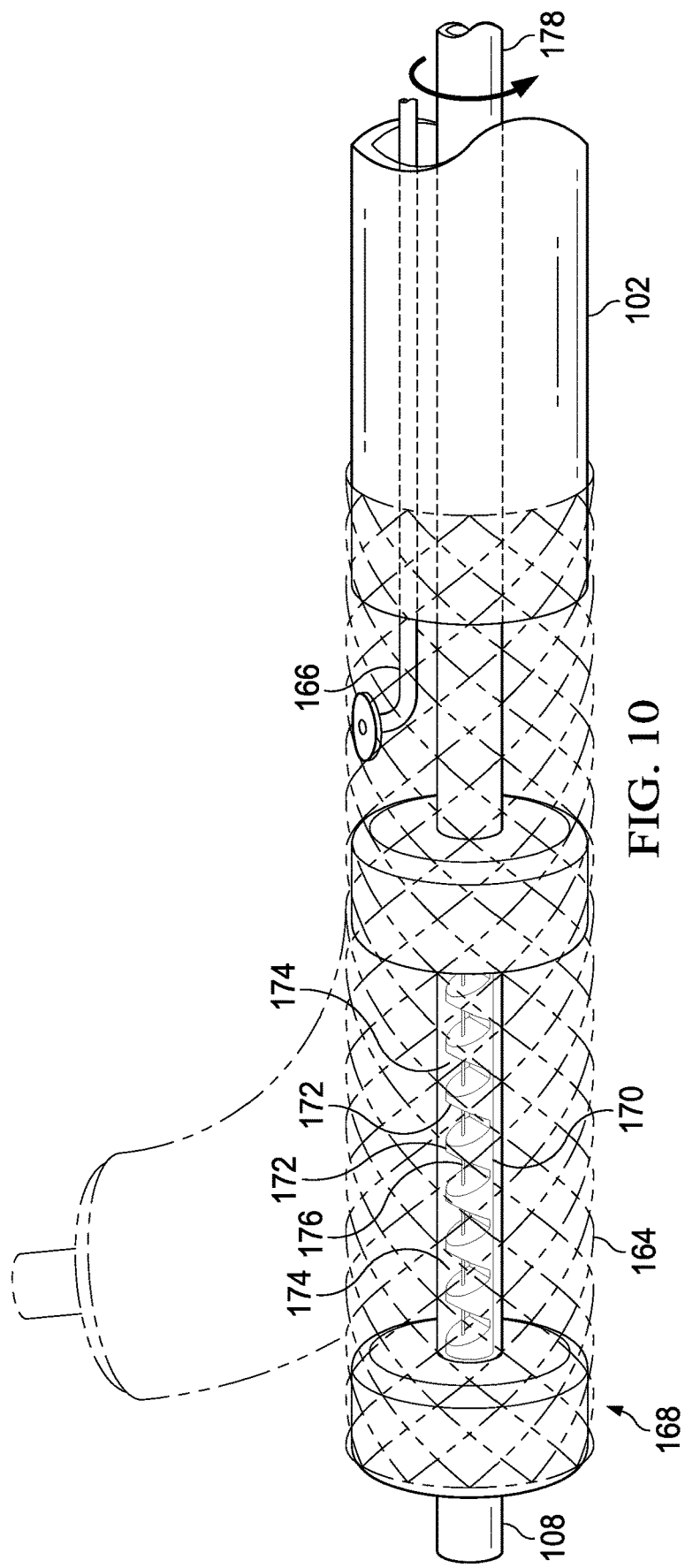
FIG. 10 depicts a perspective view of a first medical device including an articulating tip in accordance with an embodiment.

In various embodiments, the first medical device 100 may be configured to anchor a section of the antrum 22 to a distal portion of the first medical device 100. Afterwards, the distal portion of the first medical device 100 may be moved towards the second medical device 300. For example, the first medical device 100 may be configured to apply suction, for example, at a distal portion thereof. An example embodiment is described above in reference to FIG. 6B. As shown in FIG. 10, in an embodiment, the first medical device 100 may include mesh 164 (or other suction apertures) coupled by a lumen 166 to a pump. In an embodiment, the mesh 164 may be about 30 mm to about 70 mm from the distal tip. The mesh 164 may begin, in some embodiments, at the distal end 108 of the tube portion 102. In an embodiment, the mesh 164 may extend about 21 cm from the distal end 108. The mesh 164 may be continuous or segmented. The pump may apply a negative pressure through the lumen 166 causing tissue adjacent to the mesh 164 to be suctioned against the mesh 164. In an embodiment, the negative pressure used to hold the stomach tissue in place may be in a range of about 20 mmHg to about 200 mmHg, in a range of about 115 mmHg to about 135 mmHg, or about 125 mmHg. The suction may anchor the tissue, such as antrum tissue, to the distal portion of the first medical device 100. As described further below, the distal portion of the first medical device 100 may be moved towards the second medical device 300 before the second medical device 300 is clamped, which allows for more precise control of the size and shape of the resulting sleeve.

Still referring to FIG. 10, the first medical device 100 may include an articulating tip 168 in various embodiments. The first medical device 100 may include an elongate arm 170 including a plurality of ribs 172. The ribs 172 define a plurality of spaces 174 that allow the elongate arm 170 to bend in at least one direction. The first medical device 100 also includes a tensioning element 176 coupled to a distal portion of the elongate arm 170. The tensioning element 176 may be flexible, such as a wire, thread, rod, etc. In an embodiment, the tensioning element 176 extends through the ribs 172, as well as the spaces 174 between the ribs 172. The elongate arm 170 and/or the tensioning element 176 may extend through a conduit 178 that extends through the tube portion 102. For example, the proximal end of the tensioning element 176 may extend out of the tube portion 102 to be manipulated by a surgeon. The distal end of the tensioning element 176 may move between a first position and a second position. For example, the distal end of the tensioning element 176 may be pulled proximally from the first position to the second position, which causes the ribs 172 to move closer to one another (i.e., the spaces 174 between the ribs 172 become smaller or disappear). The second position of the articulating tip 168 is shown in dashed line in FIG. 10. When the tensioning element 176 is allowed to move distally towards its first position, the ribs 172 move away from each other (i.e., the spaces 174 between the ribs 172 become larger). Those skilled in the art will appreciate that other articulating techniques may be used.

For clarity purposes, a shaping portion 104 is not shown in FIG. 10, although it is contemplated that the mesh 164 may be distal of the shaping portion 104 or may extend over the shaping portion 104. For example, in an embodiment, the mesh 164 may cover at least a portion of a balloon 114 and may be flexible such that it expands when the balloon 114 is inflated. Additionally, as discussed above, the first medical device 100 may also include a lumen (e.g., lumen 120) that is configured to control inflation of the stomach lumen. In use, the first medical device 100 may be inserted into the stomach lumen. The articulating tip 168 may be tensioned such that the articulating tip 168 bends towards the lesser curvature 16 of the stomach. Suction may be applied to the mesh 164 to anchor antrum tissue to the articulating tip 168. Suction may be applied before or after the shaping portion 104 is inflated or expanded. Inflating or expanding the shaping portion 104 after the tissue has been anchored may help move the antrum tissue further due to the changing shape of the shaping portion 104. The articulating tip 168 may then be released to its first position. As the articulating tip 168 moves away from the lesser curvature 16 (i.e., towards the second medical device 300), the anchored tissue of the antrum 22 moves at the same time. The stomach lumen may then be inflated to urge the second medical device 300 against the first medical device 100, and the second medical device 100 may be clamped. As described above, anchoring the antrum tissue and moving it towards the second medical device 300 allows for more precise control of the size of the antrum in the resulting sleeve.

In addition or alternative to the articulating tip 168 described above, various techniques may be used to straighten the first medical device after tissue has been anchored to it. In an embodiment, the shaping portion of the first medical device may be a non-compliant balloon material (e.g., nylon, polyester, etc.) or a semi-compliant balloon material (e.g., Pebax®, high-durometer polyurethane, etc.).

Initially, while the shaping portion 104 is deflated, the tube portion 102 is inserted into the stomach and positioned against the lesser curvature 16 of the stomach through tissue manipulation. The balloon 114 may be uninflated or inflated to a low or medium pressure before suction is applied at the distal portion to anchor the tissue. In an embodiment, the initial low or medium pressure may be enough pressure to demonstrate the correct sleeve size but not enough to straighten out the balloon 114. After the tissue is anchored, the balloon may be inflated to a high pressure, which may straighten the balloon 114 and moves the antrum tissue further through the jaws 302, 402. A non-compliant or semi-compliant balloon may be used, for example, in combination with an articulating tip 168 as described above.

Figure 11A:
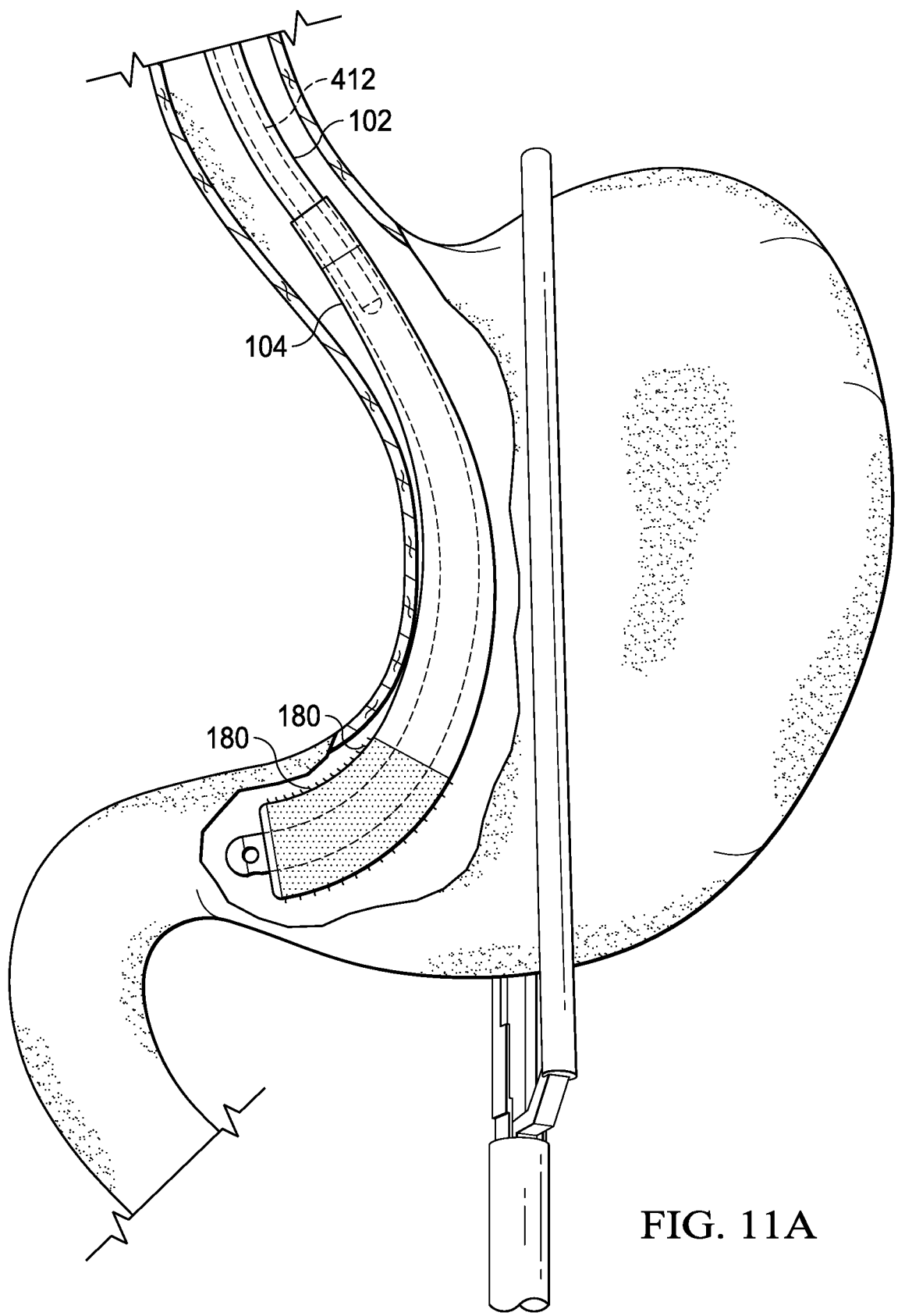
FIG. 11A depicts a perspective view of a first medical device including a tissue anchor in accordance with an embodiment.
Figure 11B:
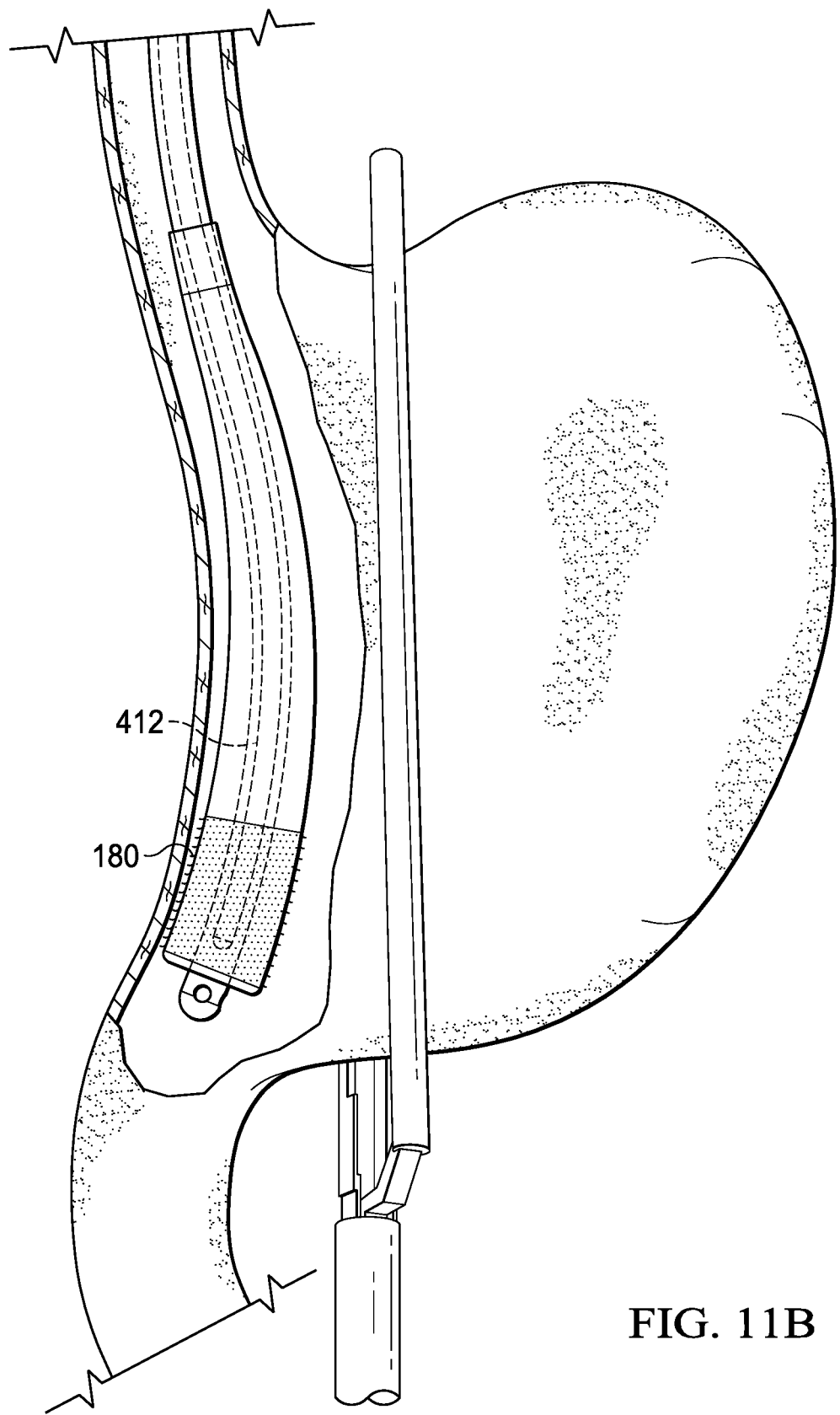
FIG. 11B depicts a perspective view of the first medical device of FIG. 11B and a stylet used to straighten the first medical device after tissue has been anchored to the tissue anchor.

In some embodiments, an additional device may be used to straighten the first medical device after tissue has been anchored to it. As shown in FIGS. 11A and 11B, in an example embodiment, the first medical device 100 may have a naturally curved distal portion, and a stylet 412 may be inserted through the first medical device 100 to straighten or move the curved portion towards the second medical device 300. In use, the first medical device 100 may be inserted into the stomach lumen where the distal portion curves toward the lesser curvature 16 of the stomach. The tissue, such as antrum tissue, may be anchored to the distal portion (e.g., using suction as described above). A stylet 412 or other rigid component (e.g., more rigid than the tube portion 102) may be inserted through the first medical device 100. As the stylet 412 enters the distal portion of the first medical device 100, the distal portion will straighten out or move towards the second medical device 300 (as shown in FIG. 11B). As described above, anchoring the antrum tissue and moving it towards the second medical device 300 allows for more precise control of the size of the antrum 22 in the resulting sleeve.

In various embodiments, techniques other than suction may be used to anchor tissue to a portion of the first medical device. As shown in FIGS. 11A and 11B, in an embodiment, an anchor 180 may be positioned on a distal portion of the first medical device 100. The anchor 180 may be configured to "grab" adjacent tissue (e.g., the mucosa). The anchor 180 may include, without limitation, hooks (e.g., similar to those used in hook-and-loop fasteners), a barb, a clip, a magnet, a suture, or a combination thereof. An overtube or introducer sheath may be used when inserting a first medical device 100 including an anchor 180, which can reduce the chance of unintentionally anchoring tissue before the first medical device is in proper position 100.

Figure 12A:
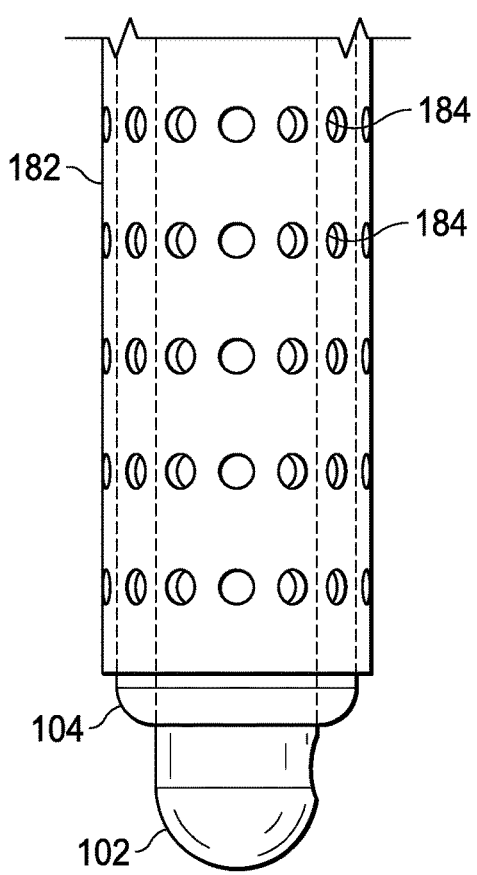
FIG. 12A depicts an elevation view of a first medical device including a perforated sheath in accordance with an embodiment.
Figure 12B:
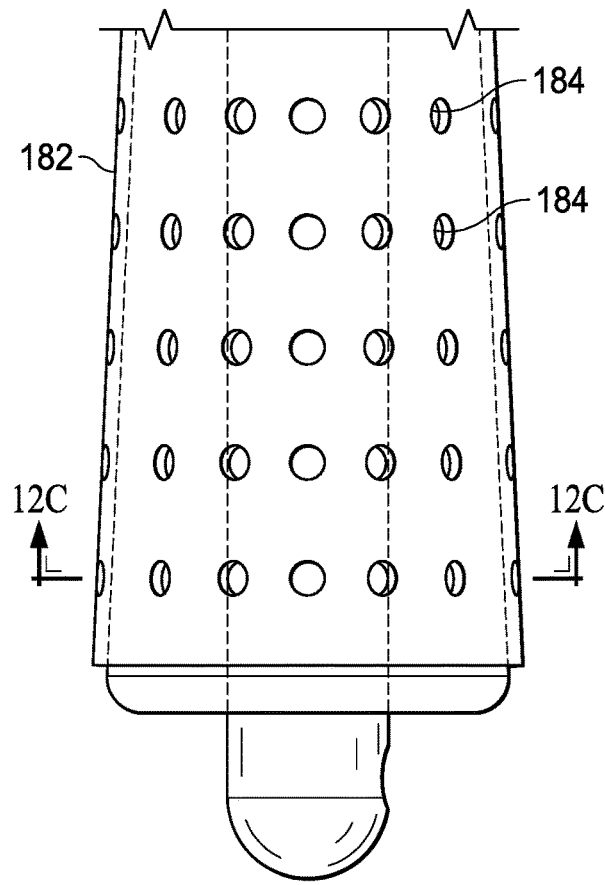
FIG. 12B depicts an elevation view of the first medical device of FIG. 12A with the shaping portion in an expanded state.
Figure 12C:
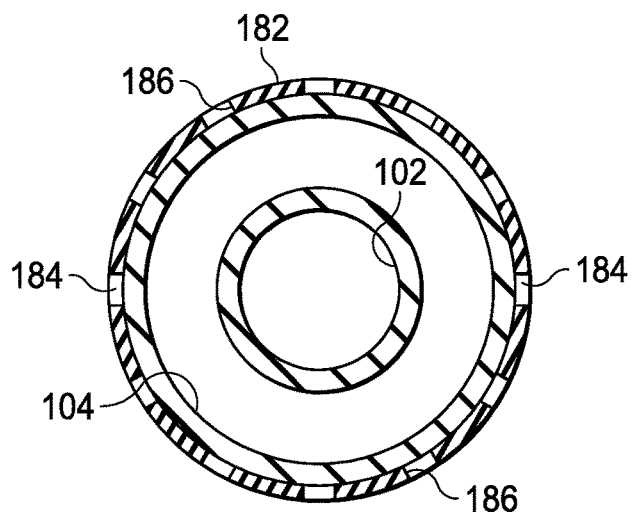
FIG. 12C depicts a cross-sectional view of the first medical device of FIG. 12A with the shaping portion in an expanded state.

In various embodiments, alternative techniques may be used to apply suction to anchor tissue to a portion of the first medical device. As shown in FIGS. 12A-12C, the first medical device 100 may include a perforated sheath 182. The perforated sheath 182 may extend from the distal end 108 of the first medical device 100 proximally along a length of the first medical device 100. Suction apertures 184 (e.g., holes, or other openings, e.g., mesh) may be positioned along a portion or an entirety of the perforated sheath 182. In example embodiments, the perforations can extend between about 30 mm to about 70 mm from the distal end or about 21 cm from the distal end. The perforations may begin, in some embodiments, at the distal end of the perforated sheath 182. In an embodiment, the perforations may extend about 21 cm from the distal end of the perforated sheath 182. The perforated sheath 182 may be continuous or segmented. The suction apertures 184 are coupled to a pump. The perforated sheath 182 may extend over the shaping portion 104 or a portion thereof. At least a portion of the perforated sheath 182 may be flexible or expandable such that, when the shaping portion 104 is inflated or expanded, the adjacent portions of the perforated sheath 182 also expand (FIG. 12B). In an embodiment, as shown in FIG. 12C, the perforated sheath 182 may include grooves 186 (e.g., channels or other lumens) coupling the suction apertures 184 to the pump. The grooves 186 may be rigid to maintain the connection between the suction apertures 184 and the pump when the perforated sheath 182 is expanded by the shaping portion 104. In other words, the expansion of the shaping portion 104 does not cause the grooves 186 to collapse thereby cutting off the suction. After the antrum tissue is anchored to the first medical device 100 by suction, the distal portion of the first medical device 100 may be moved towards the second medical device. For example, the first medical device may include an articulating tip 168 or a stylet 412 may be used, as discussed above. An overtube, such as overtube 152, may be positioned over the perforated sheath 182. For example, an overtube may be used as an introducer sheath when inserting or removing the first medical device 100 from the stomach lumen.

Figure 13:
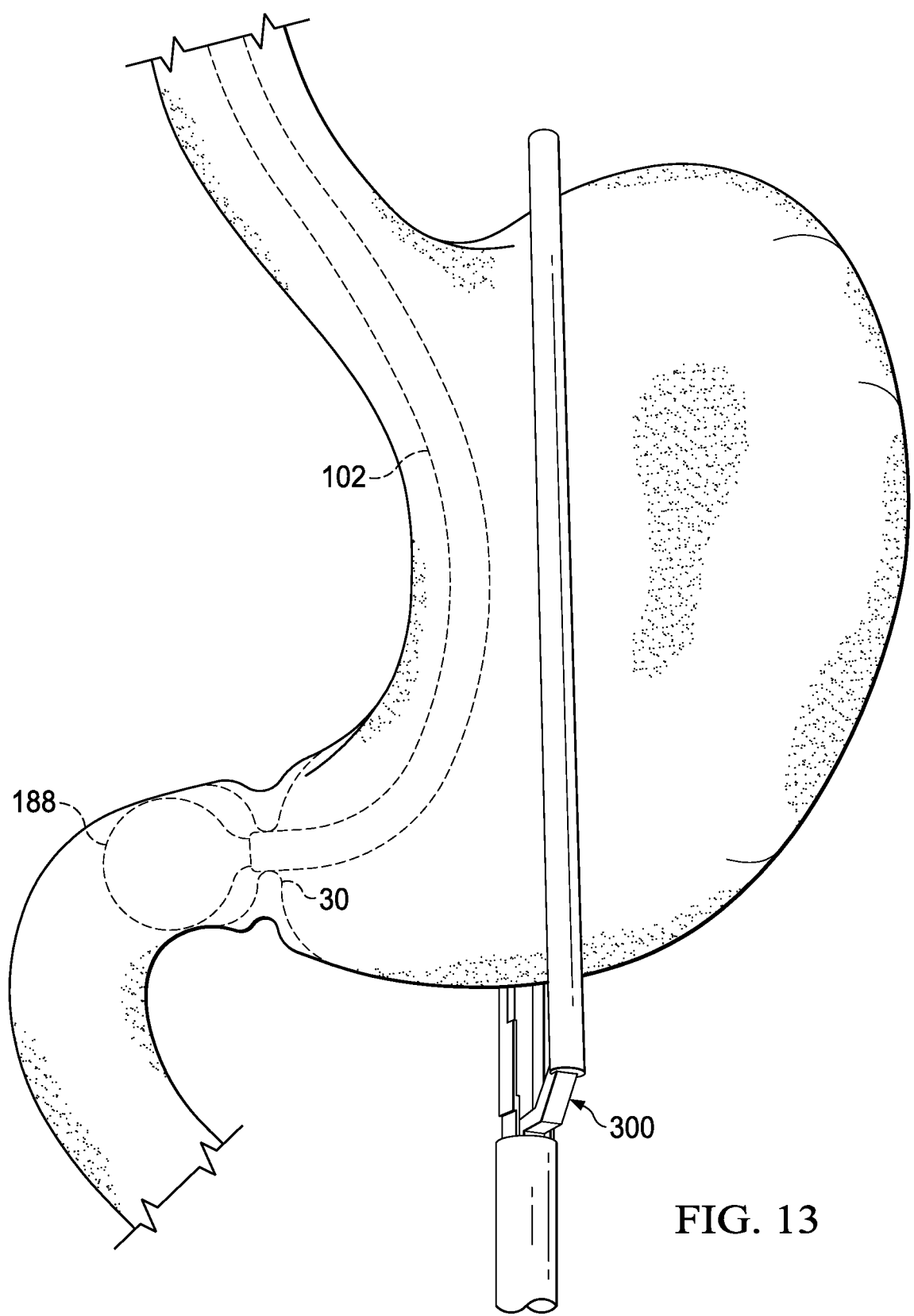
FIG. 13 depicts a perspective view of a first medical device including an inflatable balloon extending through the pyloric sphincter in accordance with an embodiment.

In addition or alternative to the suction or anchors described above, various techniques may be used to anchor tissue to a portion of the first medical device. In various embodiments, a temporary soluble adhesive coating may be included on a portion of the first medical device (e.g., on a portion of a balloon that, when expanded, is adjacent the antrum). In other embodiments, a temporary soluble adhesive may be exuded through pores on the first medical device. As shown in FIG. 13, in another embodiment, the first medical device 100 may include an inflatable or expandable portion 188 in addition to and separate from the shaping portion 104 (not shown). The inflatable or expandable portion 188 may be extended through the pyloric sphincter 30 and inflated or expanded such that it cannot be easily removed through the pyloric sphincter 30. As the distal portion of the first medical device 100 is moved towards the second medical device 300, the inflatable or expandable portion 188 pulls the pyloric sphincter 30 and the surrounding tissue in the same direction. It will be appreciated that any techniques described herein to anchor tissue to the first medical device may be used with techniques described herein to move a portion of the first medical device toward the second medical device. It will also be appreciated that other techniques may be used to perform the anchoring or the movement.

Figure 14A:
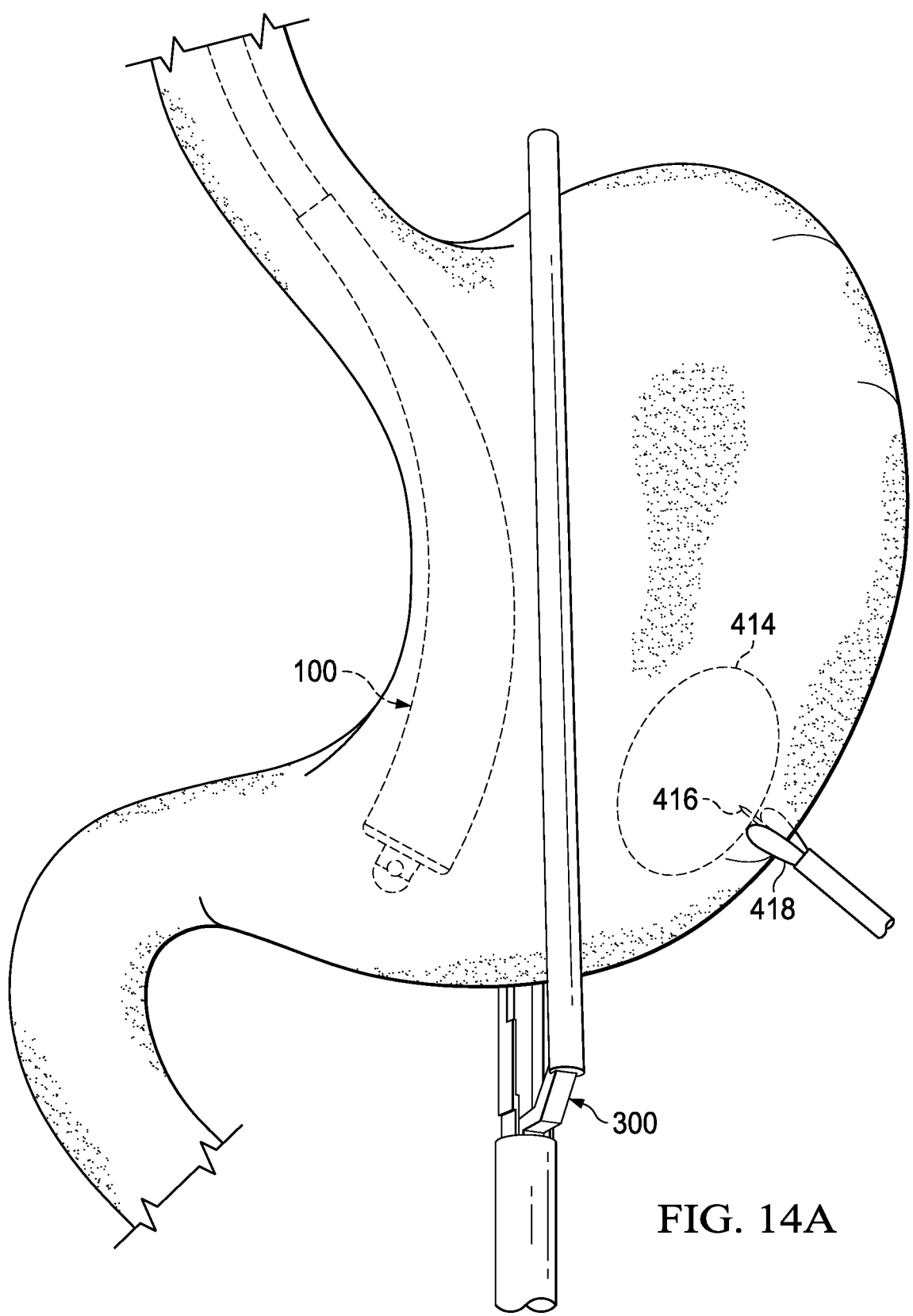
FIG. 14A depicts a perspective view of the system of FIG. 1 including an inflatable balloon inserted into the stomach lumen on the remnant side.
Figure 14B:
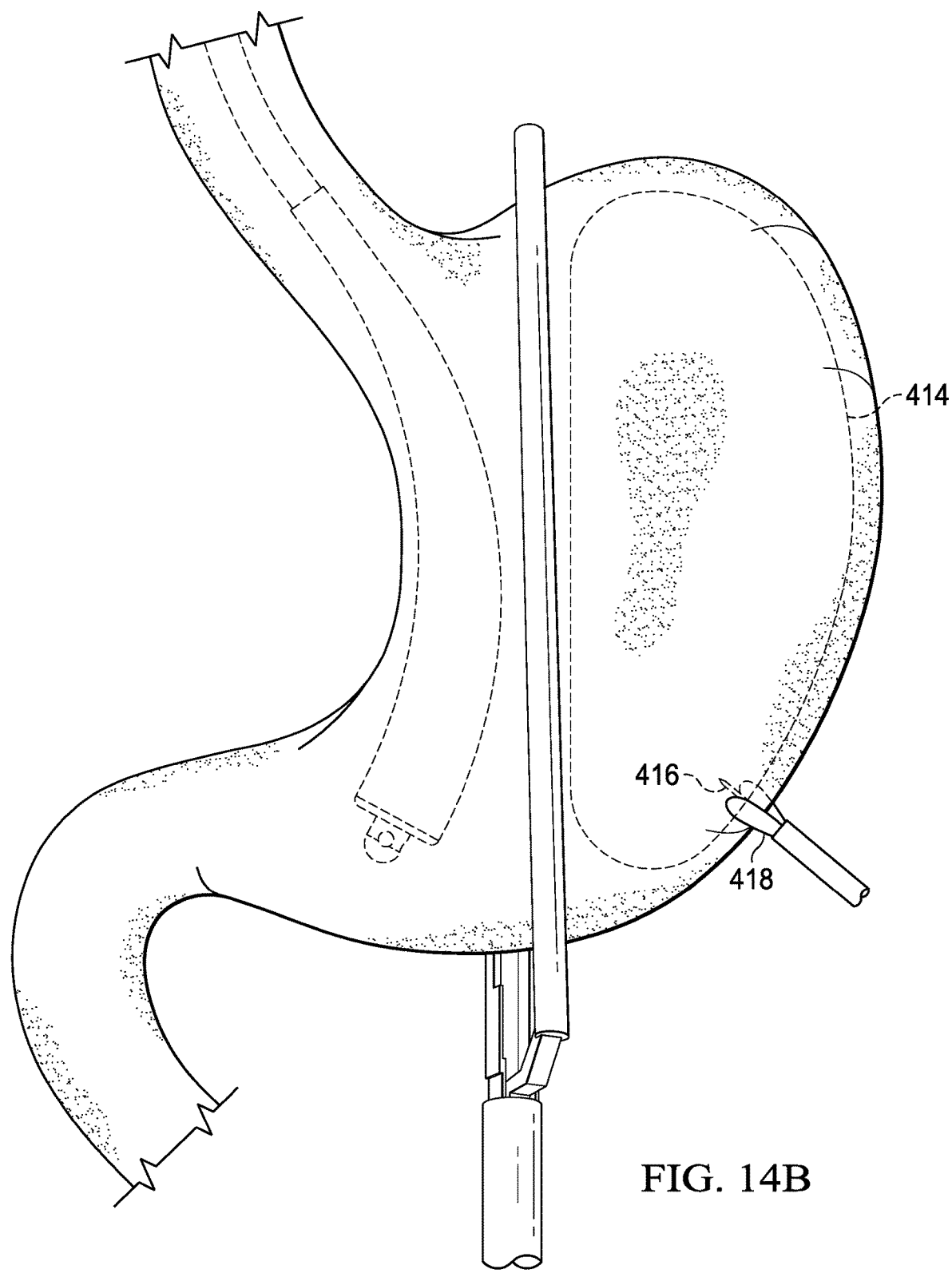
FIG. 14B depicts a perspective view of the system of FIG. 14A after the balloon has been inflated.

In some embodiments, inflation of the stomach may be at least partially controlled from the desired remnant portion of the stomach. For example, a needle may be inserted in the stomach lumen on the opposite side of the second medical device 300 from the first medical device 100 (e.g., through the fundus 24 or body 26 near the greater curvature 28) to apply inflation or suction. As shown in FIGS. 14A and 14B, in another embodiment, an inflatable or expandable component, such as a balloon 414, may be inserted into the stomach lumen on the opposite side of the second medical device 300 from the first medical device 100. The balloon 414 may be inserted through a needle 416 or catheter. The balloon 414 may be inflated to urge the second medical device 300 towards the first medical device 100. In an embodiment, the shape of the balloon 414 may be determined based on the shape of the desired sleeve. For example, the portion of the balloon 414 adjacent the antrum 22 may be shaped to move a desired portion of the antrum tissue through the jaws 302, 304 of the second medical device 300. Graspers 418 may be used to control the stomach to prevent unintentional injury (e.g., unintentionally pulling out the needle 416 before the balloon 414 is fully deflated).

Figure 15:
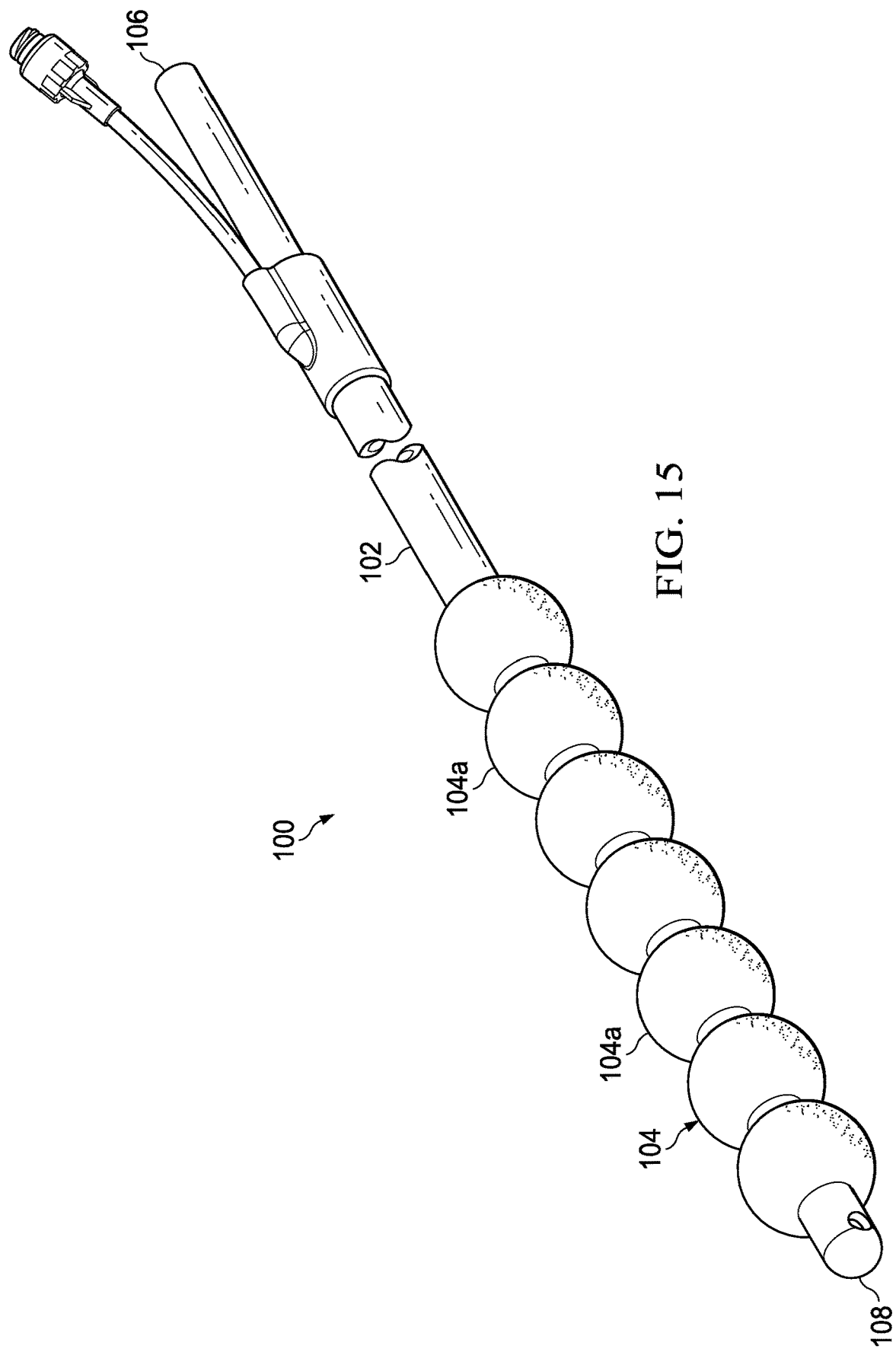
FIG. 15 depicts a perspective view of a first medical device including a segmented shaping portion in accordance with an embodiment.

In various embodiments, the system may use dynamic feedback. The system may be configured, in some embodiments, to automatically control pressurization of the stomach lumen based on the feedback. As an example, the system may use dynamic feedback to determine when to clamp the second medical device. The second medical device may be clamped manually or automatically based on the feedback. In an embodiment, as shown in FIG. 15, the shaping portion 104 can include one or more segments 104a. Each segment 104a of the shaping portion 104 may be coupled with a fluid source, for example, through separate lumens (e.g., lumen 128). Each segment 104a may also be in communication with one or more sensors 160 (e.g., shown in FIGS. 4A and 4B), such as a pressure transducer coupled to the respective fluid source or lumen. After the first medical device 100 is positioned in the stomach, each segment may be independently filled with a fluid under pressure. A catheter in communication with the stomach lumen (e.g., part of the first medical device 100 or a separate component as described above) is coupled to a pump. Fluid is introduced to the stomach lumen thus increasing the pressure and tension according to the Law of Laplace, as described above.

Still referring to FIG. 15, as the stomach lumen is pressurized and the second medical device is urged against the first medical device, the tissue surrounding the first medical device 100 will press against each segment 104a. The backpressure at each segment 104a will vary based upon the magnitude of the tissue tension as a function of the inflation pressure and as the second medical device is clamped. Each segment 104a may have a predetermined backpressure value that indicates that the desired tissue tension has been achieved for the respective segment 104a and related area of the sleeve. Once the predetermined pressure is reached, the second medical device 300 is closed for that segment 104a of the desired sleeve. Where the shaping portion 104 includes more than one segment 104a, the stomach continues to be tensioned with positive pressure in the lumen until the predetermined pressure of the next shaping portion segment 104a is reached (again indicating the desired tissue tension has been achieved in that segment 104a of the sleeve). When that desired tension is reached, that portion of the second medical device 300 is closed. This is continued until the entire second medical device 300 is closed, thus ensuring the entire sleeve was formed to have the desired tension lines. Having multiple segments 104a allows for different shapes for different portions of stomach (e.g., body 26, IA 20, antrum 22). In an embodiment where the pressure data is being displayed to the surgeon, the pressure of the shaping portion 104 or individual segments 104a may be 'zeroed' after inflating the shaping portion and before inflating the stomach lumen. This may all the surgeon or other user to easily visualize small changes in backpressure, which may be small relative to the overall pressure keeping the balloon inflated.

Figure 16A:
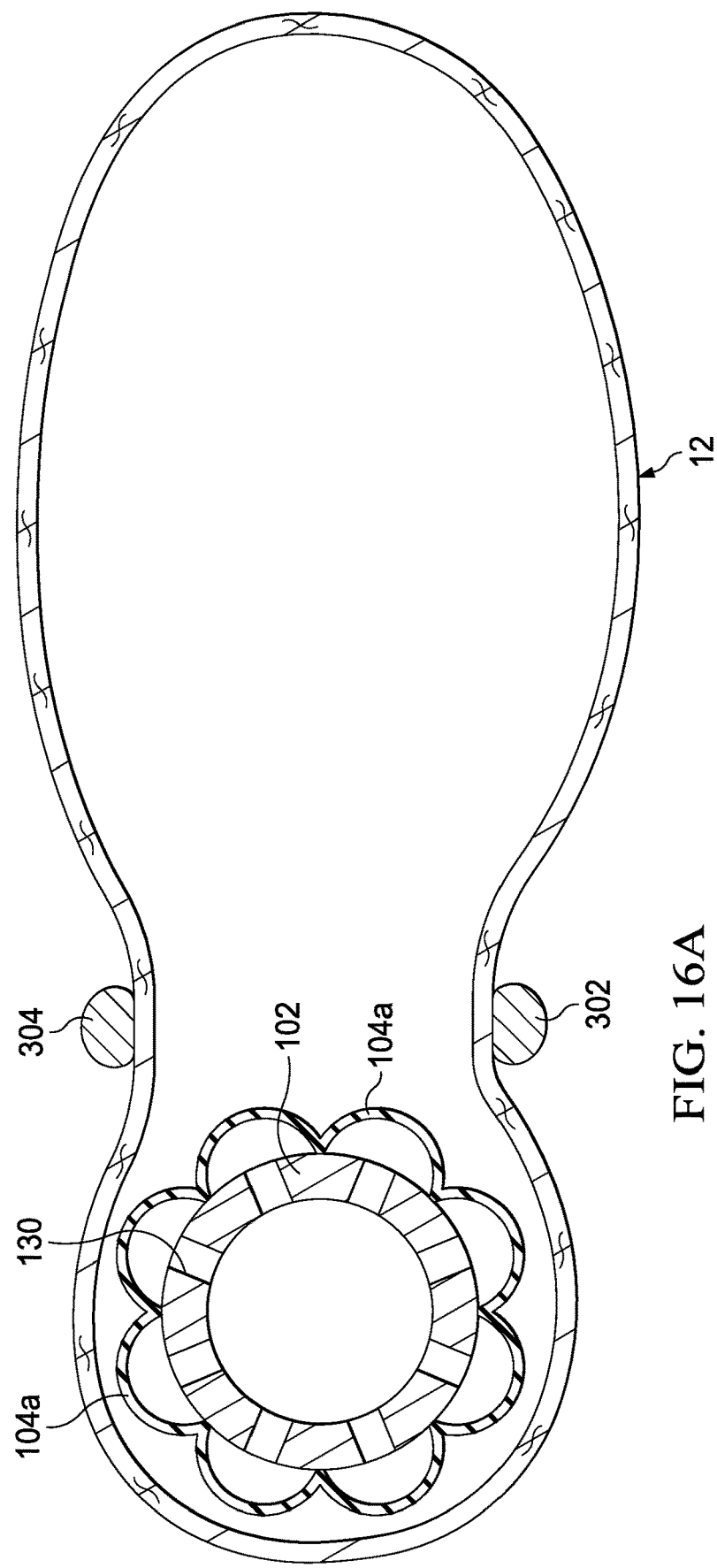
FIG. 16A depicts a cross-sectional view of a first medical device including suction zones in accordance with an embodiment, where the second medical device is in a first position.
Figure 16B:
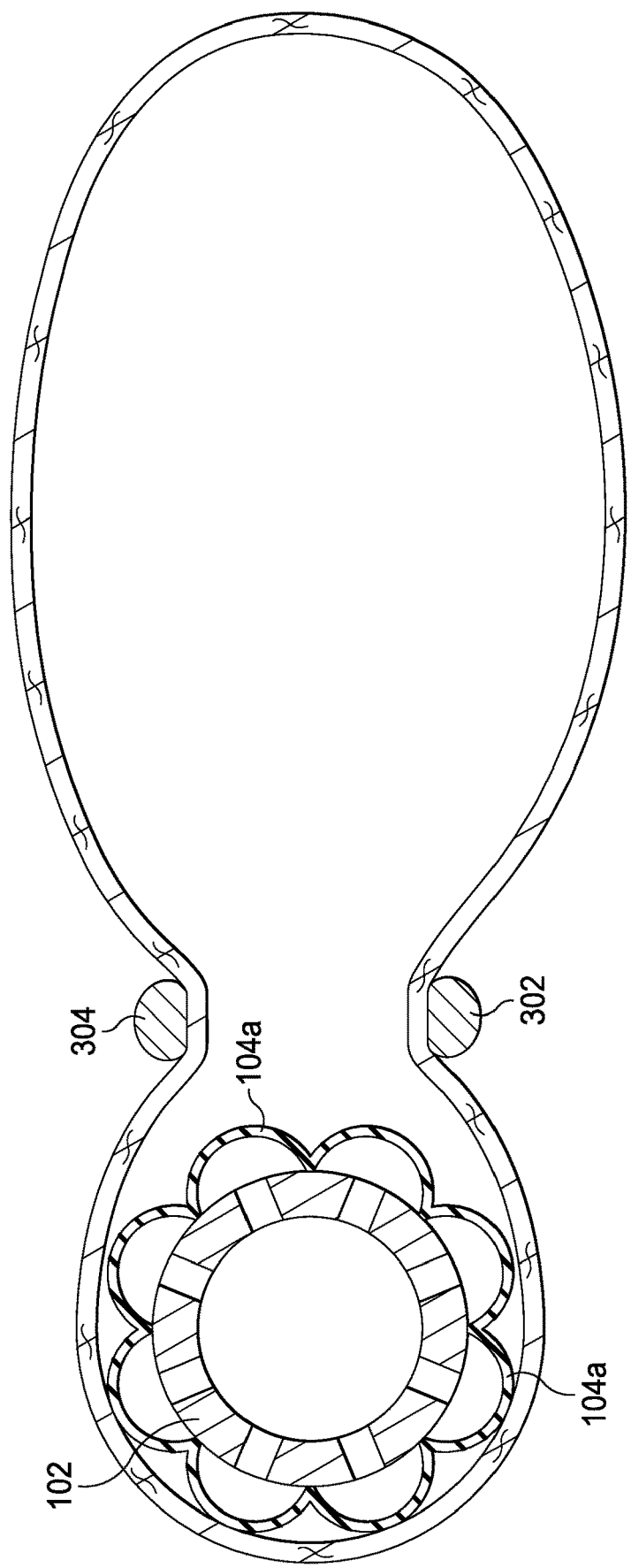
FIG. 16B depicts a cross-sectional view of the first medical device of FIG. 16A, where the second medical device is in a second position.
Figure 16C:
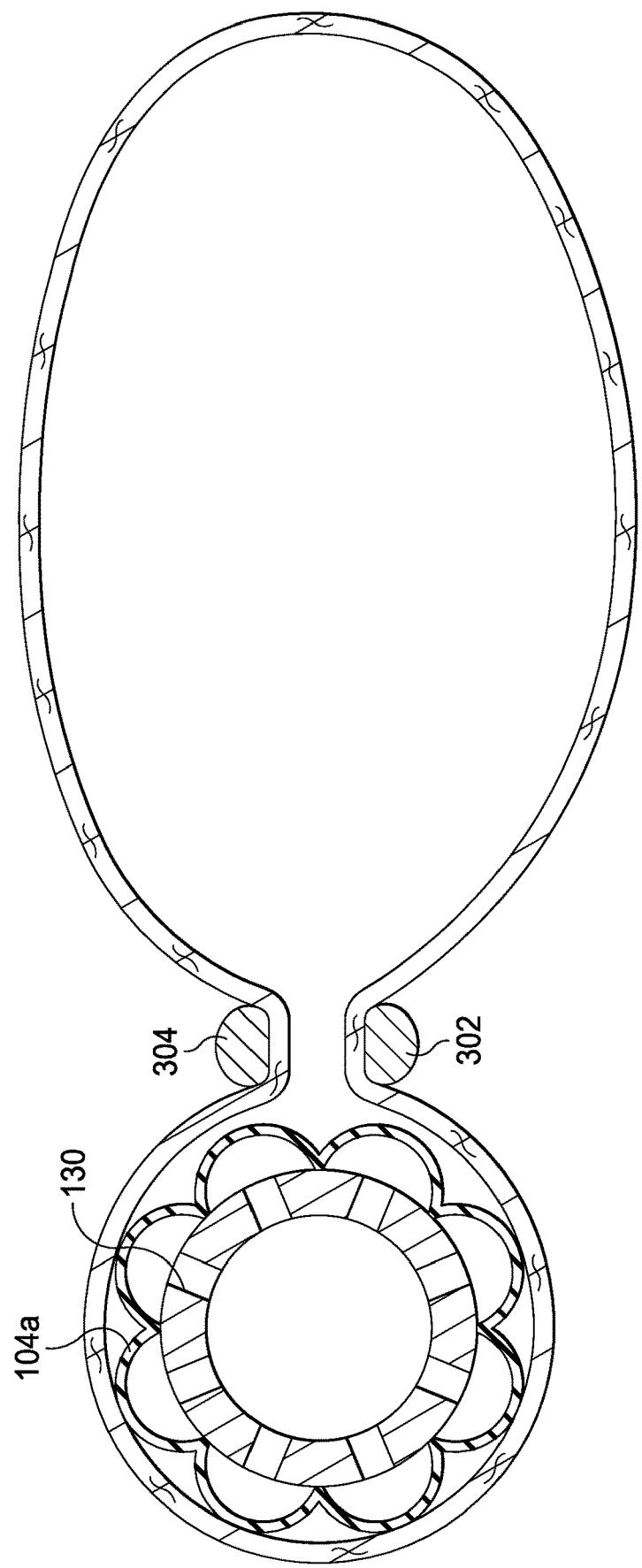
FIG. 16C depicts a cross-sectional view of the first medical device of FIG. 16A, where the second medical device is in a third position.

Referring now to FIGS. 16A-16C, in an example embodiment, the shaping portion 104 may be segmented along the length thereof. Each segment 104a may be coupled to a pump and one or more sensors, as discussed above. Based on the magnitude of the backpressure each segment 104a is experiencing, the system and/or the surgeon may be able to determine the position of the surrounding tissue before clamping the second medical device. For example, the segments 104a adjacent the lesser curvature 16 experiencing a relatively high backpressure may indicate that the lesser curvature 16 of the stomach is in the desired position relative to the first medical device 100 (FIG. 16B). Additionally, all of the segments 104a experiencing a relatively high backpressure may be an indication that the tissue surrounding the first medical device 100 is in the desired position and the second medical device 300 may be clamped (FIG. 16C).

In various embodiments, the system may use dynamic feedback to reach the desired pressure in both the shaping portion and the stomach lumen. For example, the system may adjust the inflation (e.g., add more pressure or use suction to reduce pressure) of the stomach lumen and/or the shaping portion based on feedback from the first medical device. The pressure may be adjusted manually or automatically based on the feedback. The first medical device could include one or more segments coupled to one or more sensors, such as with the configurations in FIGS. 15-16C. The measured backpressure at the one or more segments may be used in determining whether to increase, maintain, or reduce pressure in the stomach lumen. In some embodiments, inflation and suction may be alternated to position portions of the stomach tissue relative to the second medical device as desired. The backpressure on the shaping portion may slightly increase after the second medical device is clamped.

Figure 17A:
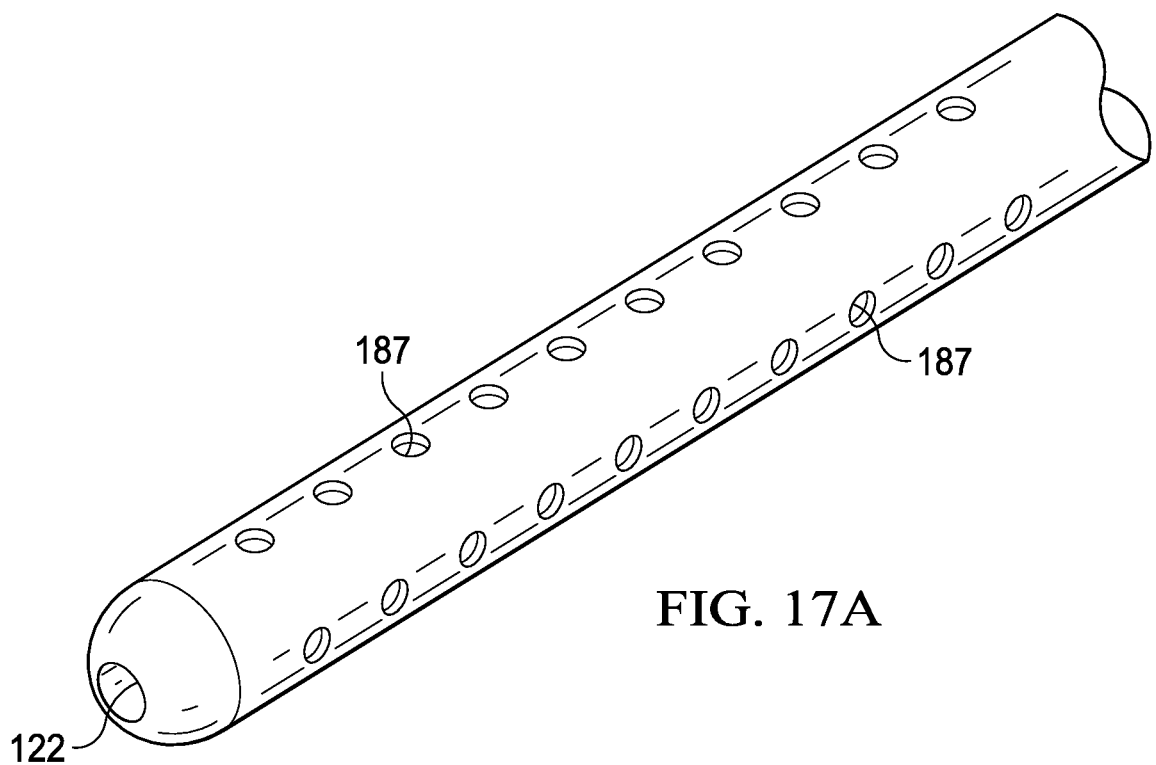
FIG. 17A depicts a perspective view of a tube portion of a first medical device including suction zones in accordance with an embodiment.
Figure 17B:
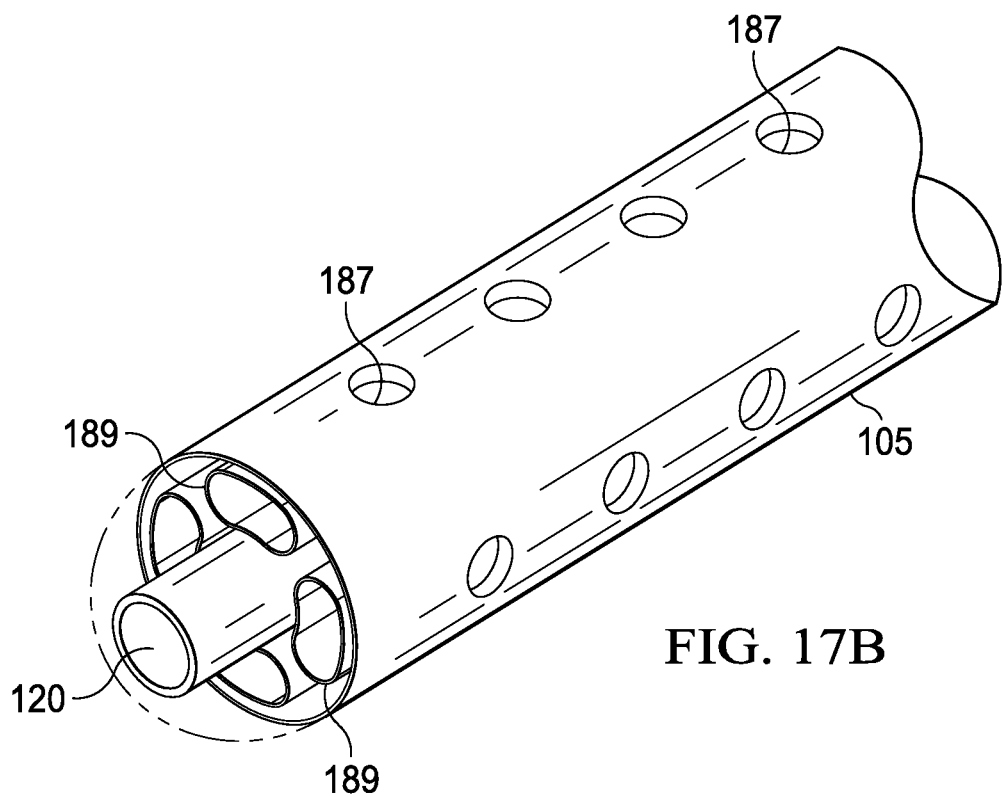
FIG. 17B depicts a perspective view of the tube portion of FIG. 17A with the cap removed.
Figure 18A:
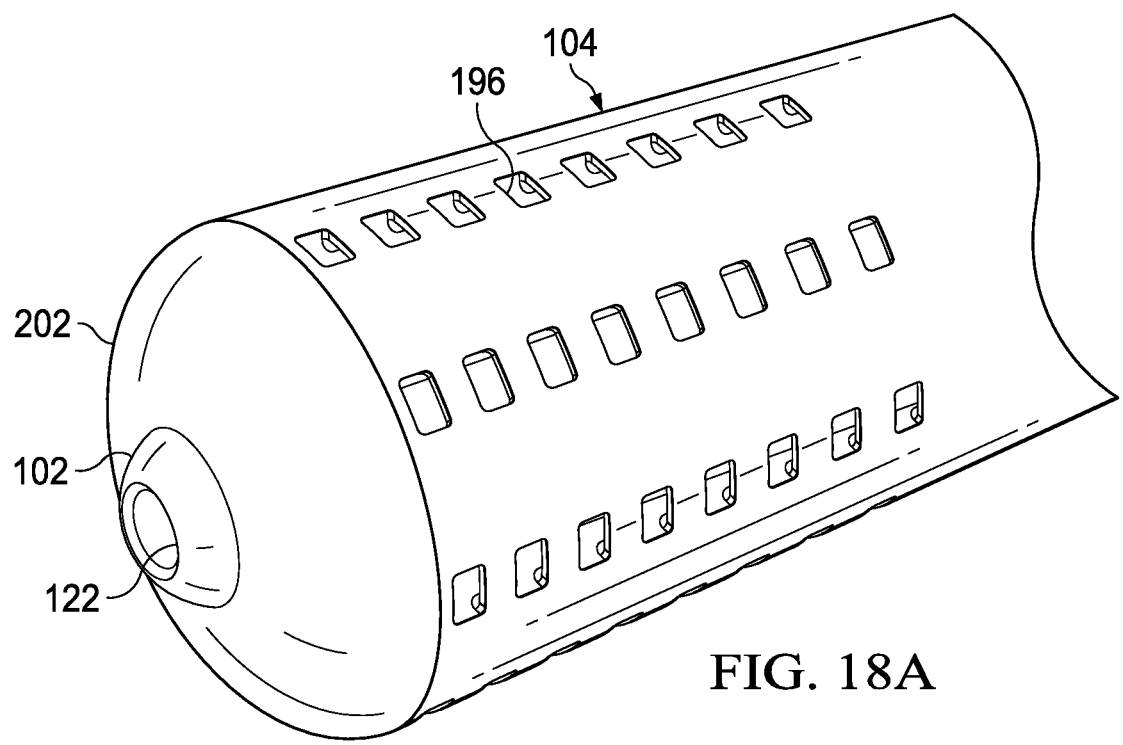
FIG. 18A depicts a perspective view of a first medical device including suction zones in accordance with an embodiment.
Figure 18B:
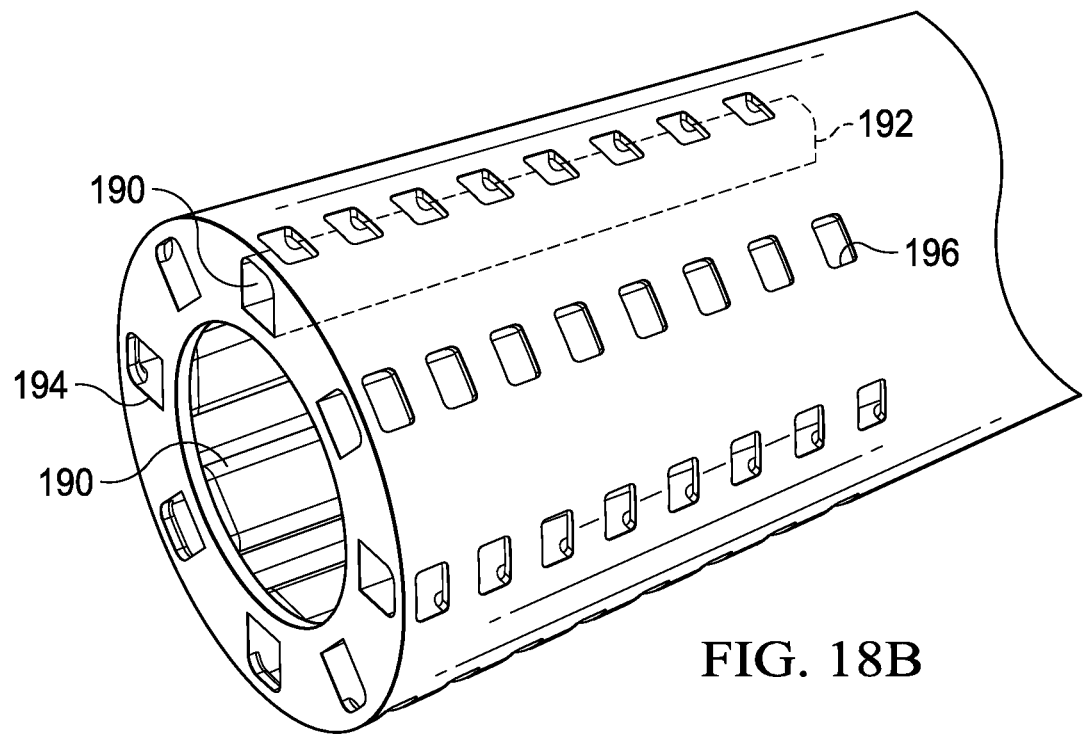
FIG. 18B depicts a perspective view of a shaping portion of the first medical device of FIG. 18A.
Figure 18C:
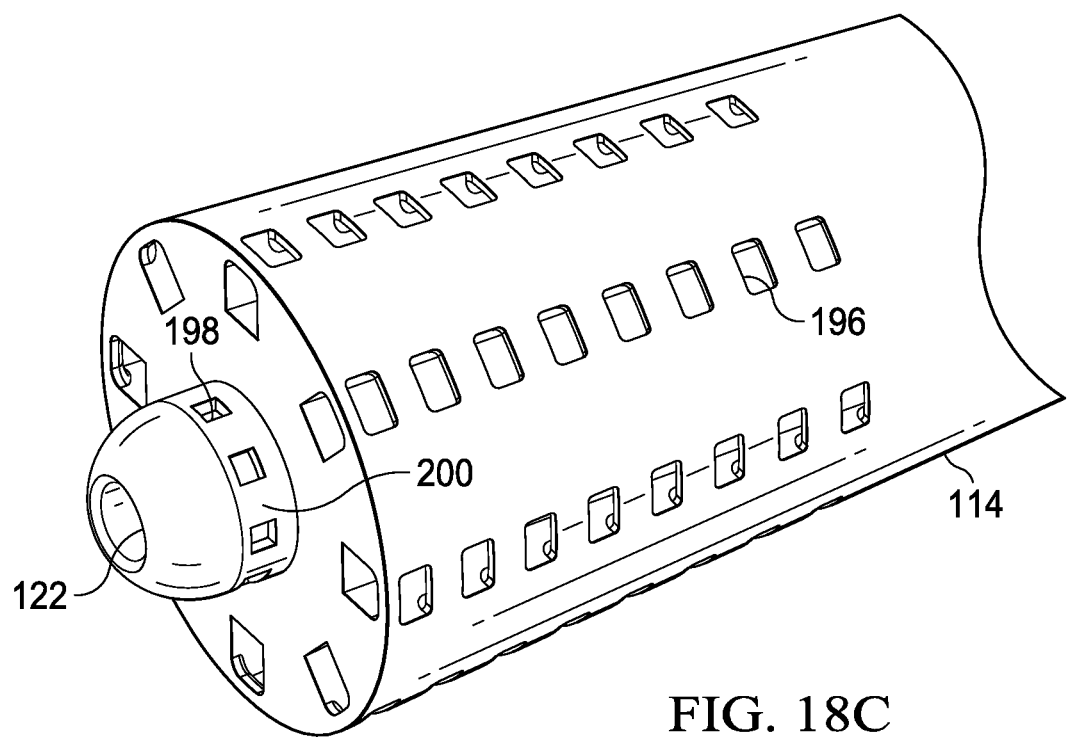
FIG. 18C depicts a perspective view of the shaping portion and the tube portion of the first medical device of FIG. 18A.
Figure 18D:
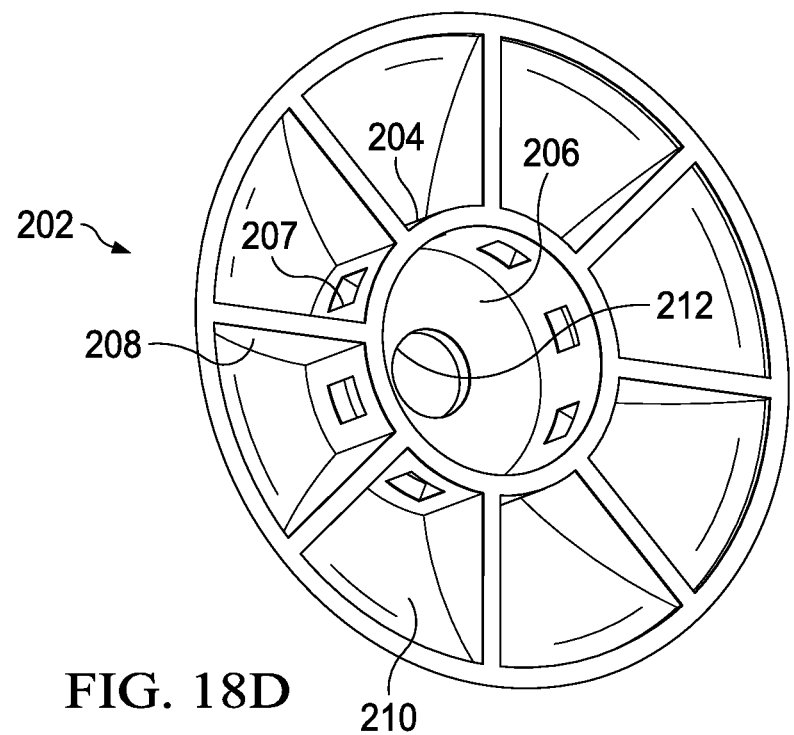
FIG. 18D depicts a perspective view of a manifold cap of the first medical device of FIG. 18A.

In various embodiments, feedback other than backpressure on the first medical device may be used to determine when to clamp the second medical device. For example, the first medical device may be configured to determine whether the tissue surrounding the first medical device is properly tensioned. The first medical device may be configured to measure suction in zones along the length of the first medical device. The shaping portion, for example, can include more than one sets of suction apertures (or other openings as discussed above). The suctions apertures may be arranged in zones or separate segments. For example, as shown in FIGS. 17A and 17B, four zones of suction apertures 187 are arranged around a diameter of the tube portion 102 of the first medical device 100. The suction apertures 187 may extend along the first medical device 100 for about the length of the stomach (e.g., about 21 cm). Each of the suction apertures 187 in the same zone are collectively coupled to a pump (e.g., a single pump or individual pumps) and a sensor. For example, a lumen 189 may couple each suction aperture 187 in a respective zone with the pump. Although not shown, the shaping portion 104 may define channels for each of the suction apertures 187 such that the shaping portion 104 does not interfere with suction from the tube portion 102. As the stomach is inflated and the second medical device 300 is being urged against the first medical device 100, suction may be applied to each zone. An example negative pressure may be in a range of about 20 mmHg to about 200 mmHg, in a range of about 115 mmHg to about 135 mmHg, or about 125 mmHg. The system may be configured to determine when the suction apertures 187 in each zone become occluded (e.g., by adjacent tissue). The suction may be discontinued in a zone where the suction apertures 187 have become occluded. Based on the number of zones that are occluded or which specific zones are occluded, the system and/or the surgeon may be able to determine the position of the surrounding tissue before clamping the second medical device. For example, two of four zones being occluded may indicate that the lesser curvature 16 of the stomach is grounded to the first medical device. Additionally, all of the zones being occluded may be an indication that the tissue surrounding the first medical device 100 is in the desired position and the second medical device 300 may be clamped.

It will be recognized that the number and configuration of suction zones may vary. For example, with reference to FIGS. 18A-18D, the first medical device may include 8 suction zones. The shaping portion 104 of the first medical device 100 may include a separate lumen 190 for each zone. The lumens 190 may each extend from a closed proximal end 192 to an open distal end 194 and be in communication with a plurality of suction apertures 196. The tube portion 102 of the first medical device 100 may include tube openings 198, each of which correspond to a separate lumen 190. The tube openings 198 may be collectively coupled to a pump. In an embodiment, the tube openings 198 are positioned on a sidewall 200 of the tube portion 102 adjacent the distal end 108. Each tube opening 198 and corresponding lumen 190 are in fluid communication with each other. For example, the shaping portion 104 may include a manifold cap 202 that couples each tube opening 198 to the corresponding lumen 190. The manifold cap 202 may be segmented, and the number of segments may correspond to the number of suction zones. The manifold cap 202 may include an inner wall 204 defining a channel 206 sized to receive the distal end 108 of the tube portion 102. The inner wall 204 also defines apertures 207 configured to align with the tube openings 198 when the tube portion 102 extends into the channel 206. Extending from the inner wall 204 are dividers 208 that define a series of chambers 210, each chamber 210 corresponding to one of the apertures 207. When assembled, each chamber 210 fluidly couples each aperture 207 with a corresponding open distal end 194 of a lumen 190. The dividers 208 prevent or substantially prevent airflow between each chamber 210. With such a configuration, one source of suction is coupled to multiple independent zones. The manifold cap 202 may also include an outlet 212 at its distal end. The outlet 212 may allow the lumen 120 in the tube portion 102 to be in communication with the stomach lumen (e.g., to control the pressure in the stomach lumen). As described above, the zones of suction may be used by the surgeon or system to determine the position of tissue surrounding the first medical device 100 and/or when to clamp the second medical device 300.

Figure 19A:
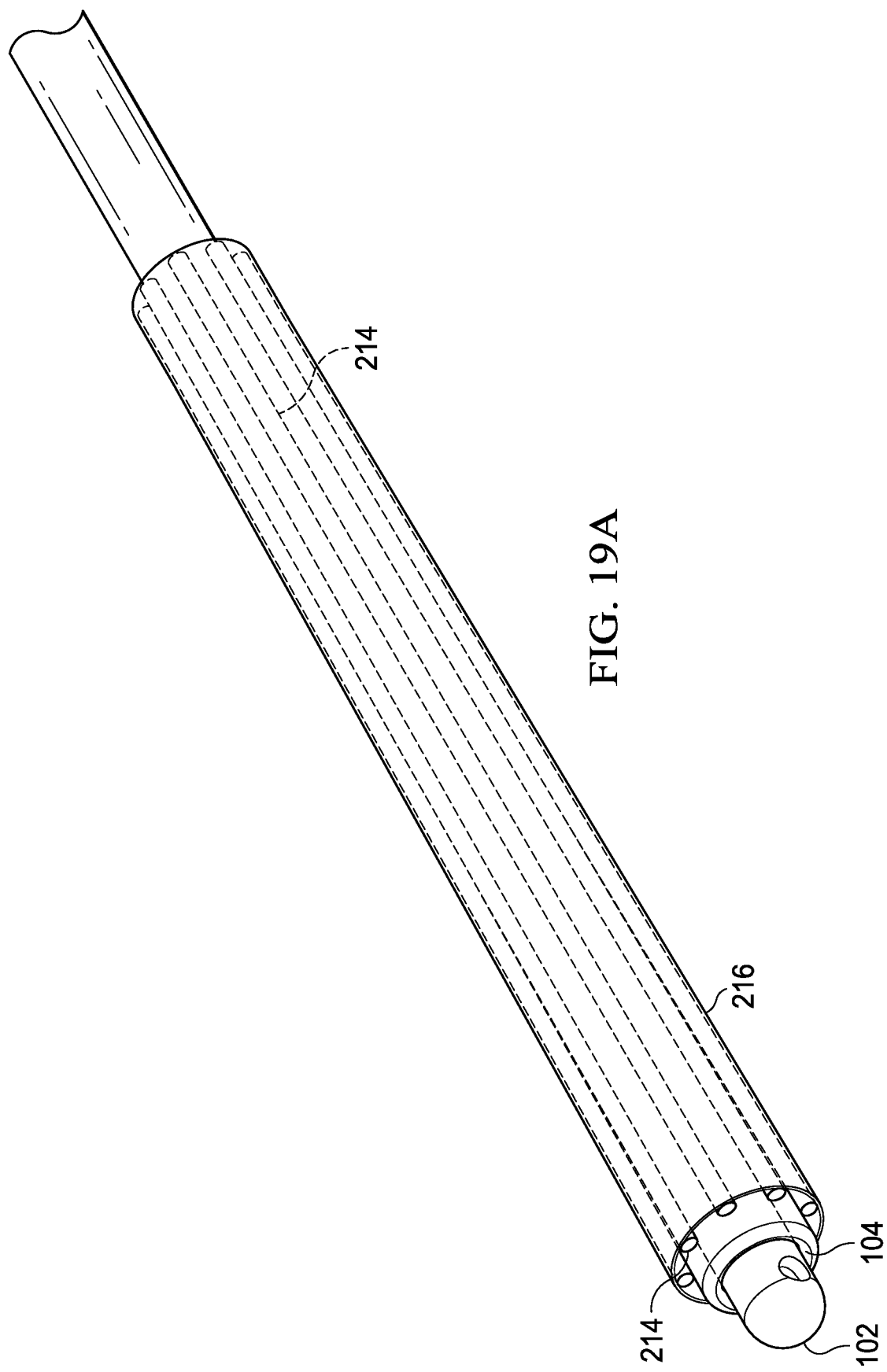
FIG. 19A depicts a cross-sectional view of a first medical device including suction zones in accordance with another embodiment.
Figure 19B:
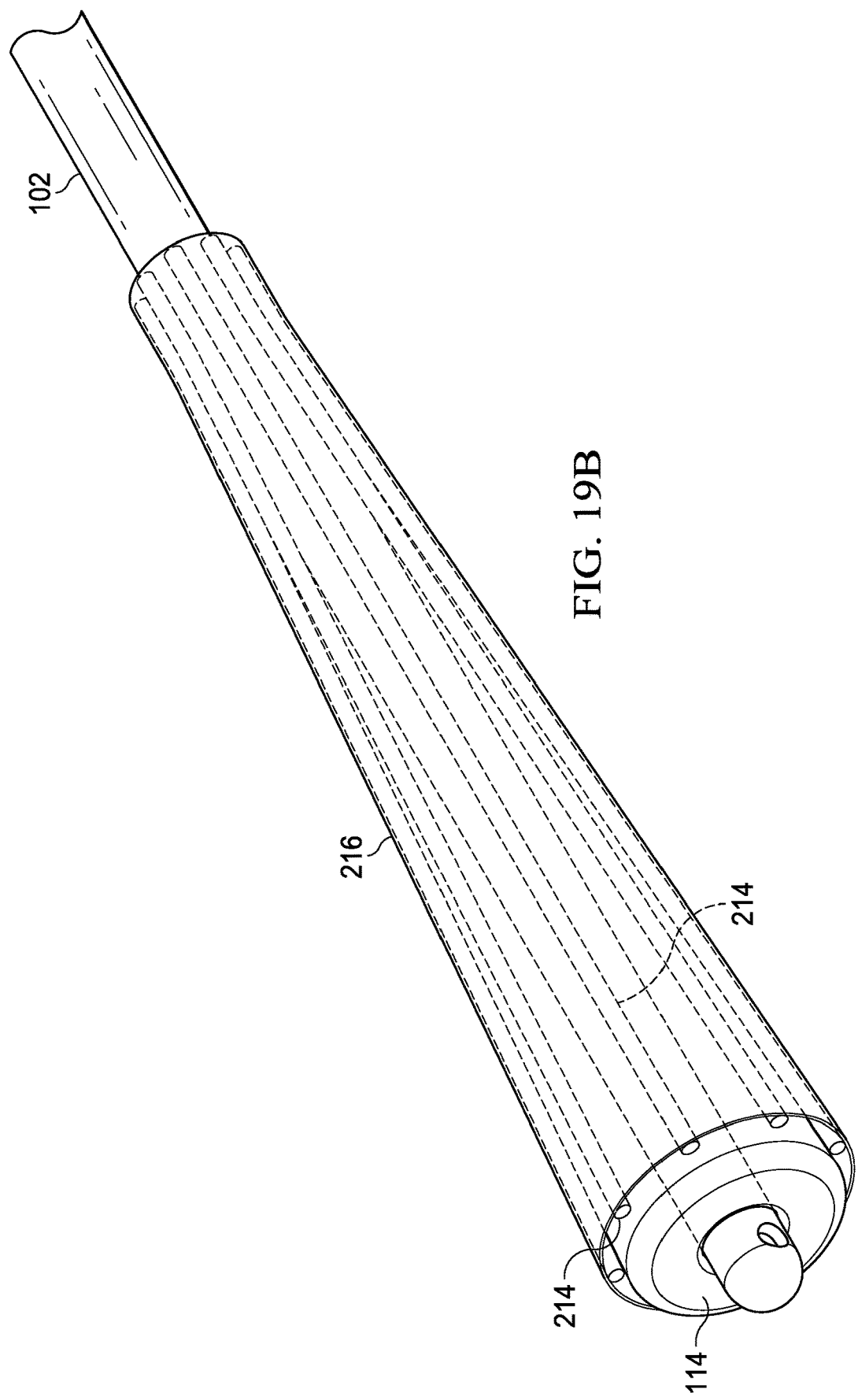
FIG. 19B depicts a cross-sectional view of a first medical device of FIG. 19A with the shaping portion inflated.

With reference to FIGS. 19A and 19B, in various embodiments, the first medical device 100 may include suction lumens 214 positioned on an exterior of the shaping portion 104. Each suction lumen 214 may include one or more suction apertures (not shown for clarity purposes). The suction lumens 214 may each be coupled to a pump. The system may be configured to measure the suction applied through each lumen 214. For example, each lumen 214 may be coupled to a sensor. In an embodiment, the suction lumens 214 are positioned longitudinally around a diameter of the shaping portion 104. The suction lumens 214 may be flexible to allow for expansion when the shaping portion 104 is inflated or expanded. In various embodiments, the suction lumens 214 may be coupled to the shaping portion 104 or held in position on the shaping portion 104 by, for example, an outer elastic sheath 216. The elastic sheath 216 is porous or otherwise perforated to allow suction from the suction lumens 214 through the elastic sheath 216. As discussed above, the system may be configured to determine when the suction apertures in each lumen 214 become occluded (e.g., by adjacent tissue), which can be used to inform the system or the surgeon about the current state of the procedure or whether it is time to clamp the second medical device.

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Versions of the devices described above may be actuated mechanically or electromechanically (e.g., using one or more electrical motors, solenoids, etc.). However, other actuation modes may be suitable as well including but not limited to pneumatic and/or hydraulic actuation, etc. Various suitable ways in which such alternative forms of actuation may be provided in a device as described above will be apparent to those of ordinary skill in the art in view of the teachings herein.

Versions of the devices described above may have various types of construction. By way of example only, any of the devices described herein, or components thereof, may be constructed from a variety of metal and/or plastic materials.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. An apparatus for performing a sleeve gastrectomy, the apparatus comprising:
   (a) a bougie for insertion into an interior of a stomach, the bougie having a proximal bougie end and a distal bougie end;
   (b) an inflation lumen having a proximal lumen end and a distal lumen end, the inflation lumen extending from the proximal bougie end through the distal bougie end;
   (c) a fluid delivery system coupled with the proximal lumen end, the fluid delivery system having a first mode in which the fluid delivery system delivers positive pressure in a predetermined positive pressure range into the stomach prior to the stomach being resected, the predetermined positive pressure range being based on a size or a shape of the stomach prior to the stomach being resected, and a second mode after the stomach has been resected; and
   (d) a monitor coupled with the proximal lumen end operably configured for the monitoring of pressure or volume within the stomach, and to provide an indication when the predetermined positive pressure range is reached,
   wherein the bougie is operably configured to define a resection line for the sleeve gastrectomy when the predetermined positive pressure range is achieved within the stomach, wherein the resection line is defined at least partially by the position of the bougie relative to a second medical device clamped externally on the stomach laterally adjacent to the bougie at a first amount of compression or a second amount of compression, wherein the second amount of compression is both greater than the first amount of compression and operably configured to immovably retain the stomach while at the predetermined positive pressure range, wherein the bougie includes at least one sensor coupled with the distal bougie end for monitoring a pressure within the stomach, wherein the monitor is configured to provide the indication that the predetermined positive pressure range is reached to the second medical device based on output of the at least one sensor, and wherein the indication is configured to cause the second medical device to clamp the stomach at the second amount of compression, and wherein the apparatus is configured to simultaneously deliver the positive pressure and provide suction.

2. The apparatus of claim 1, wherein the bougie includes at least one balloon portion positioned at the distal bougie end.

3. The apparatus of claim 1, wherein the inflation lumen can be used for both inflation and suction.

4. The apparatus of claim 1, wherein the fluid delivery system is a hand pump or a foot pump.

5. The apparatus of claim 1, wherein the monitor comprises a visual indicator or an audible indicator, and wherein the monitor is configured to provide the indication that the predetermined positive pressure range is reached to a user via the visual indicator or the audible indicator.

6. The apparatus of claim 1, wherein the monitor comprises a control system for metering a fluid delivered through the inflation lumen.

7. The apparatus of claim 1, wherein the bougie includes a shaping portion positioned at the distal bougie end.

8. The apparatus of claim 7, wherein the shaping portion is a balloon.

9. The apparatus of claim 7, wherein the bougie includes an articulating tip, wherein the suction is provided at the articulating tip.

10. The apparatus of claim 1, further comprising an overtube positioned on the distal bougie end.

11. The apparatus of claim 1, wherein the bougie includes a multi-lumen catheter.

12. The apparatus of claim 1, wherein the predetermined positive pressure range is from 15 mmHG to 20 mmHG.

13. An apparatus for performing a sleeve gastrectomy, the apparatus comprising:
(a) a bougie for insertion into an interior of a stomach, the bougie having a proximal bougie end and a distal bougie end;
(b) an inflation lumen having a proximal lumen end and a distal lumen end, the inflation lumen extending from the proximal bougie end through the distal bougie end;
(c) a fluid delivery system coupled with the proximal lumen end, the fluid delivery system having a first mode in which the fluid delivery system delivers positive pressure in a predetermined positive pressure range of positive pressure into the stomach prior to the stomach being resected, the predetermined positive pressure range being based on a size or a shape of the stomach prior to the stomach being resected, and a second mode after the stomach has been resected; and
(d) a control system coupled with the proximal lumen end for the metering and monitoring of pressure or volume within the stomach, wherein the control system is configured to provide an indication when the predetermined positive pressure range is reached, wherein the bougie is operably configured to cooperate with a stapler or clamp that is clamped externally on the stomach laterally adjacent to the bougie at a first amount of compression or a second amount of compression to define a resection line for the sleeve gastrectomy when the predetermined positive pressure range is achieved within the stomach, wherein the second amount of compression is both greater than the first amount of compression and operably configured to immovably retain the stomach while at the predetermined positive pressure range, wherein the bougie includes at least one sensor coupled with the distal bougie end for monitoring a pressure within the stomach, wherein the control system is configured to provide the indication that the predetermined positive pressure range is reached to the stapler or clamp based on output of the at least one sensor, and wherein the indication is configured to cause the stapler or clamp to clamp the stomach at the second amount of compression, and wherein the apparatus is operably configured to simultaneously deliver the positive pressure and provide suction.

14. The apparatus of claim 13, wherein the bougie includes at least one balloon portion positioned at the distal bougie end.

15. The apparatus of claim 13, wherein the inflation lumen can be used for both inflation and suction.

16. The apparatus of claim 13, wherein the fluid delivery system is a hand pump or a foot pump.

17. The apparatus of claim 13, wherein the control system comprises a visual indicator or an audible indicator, and wherein the control system is configured to provide the indication that the predetermined positive pressure range is reached to a user via the visual indicator or the audible indicator.

18. The apparatus of claim 13, wherein the control system comprises a control system for metering and monitoring a fluid delivered through the inflation lumen.

19. The apparatus of claim 13, wherein the bougie includes a shaping portion positioned at the distal bougie end.

20. The apparatus of claim 19, wherein the shaping portion is a balloon.

21. The apparatus of claim 19, wherein the bougie includes an articulating tip, wherein the suction is provided at the articulating tip.

22. The apparatus of claim 13, further comprising an overtube positioned on the distal bougie end.

23. The apparatus of claim 13, wherein the bougie includes a multi-lumen catheter.

24. The apparatus of claim 13, wherein the predetermined positive pressure range is from 15 mmHG to 20 mmHG.

25. A system for performing a sleeve gastrectomy, the system comprising:
(a) a first medical device, the first medical device including;
(i) a bougie for insertion into an interior of a stomach, the bougie having a proximal bougie end and a distal bougie end,
(ii) an inflation lumen having a proximal lumen end and a distal lumen end, the inflation lumen extending from the proximal bougie end through the distal bougie end,
(iii) a pump coupled with the proximal lumen end, the pump having a first mode in which the pump delivers positive pressure in a predetermined positive pressure range into the stomach prior to the stomach being resected, the predetermined positive pressure range being based on a size or a shape of the stomach prior to the stomach being resected, and a second mode after the stomach has been resected, (iv) a monitor coupled with the proximal lumen end for the monitoring of pressure or volume of the stomach, and configured to provide an indication when the predetermined positive pressure range is reached, and (v) a shaping portion, the shaping portion being positioned at the distal bougie end, wherein the shaping portion is operably configured to position a portion of the stomach, wherein the first medical device is operably configured to simultaneously deliver the positive pressure and provide suction, and (b) a second medical device, the second medical device being a stapler or clamp positioned externally on the stomach laterally adjacent to the first medical device;

wherein the first medical device and the second medical device are operably configured to define a resection line for the sleeve gastrectomy when the predetermined positive pressure range is achieved within the stomach, wherein the resection line is defined at least partially by the position of the first medical device relative to the second medical device;

wherein the first medical device includes at least one sensor coupled with the distal bougie end for monitoring a pressure or volume within the stomach, wherein the monitor is configured to provide the indication that the predetermined positive pressure range is reached to the second medical device based on output of the at least one sensor, and wherein the indication is configured to cause the second medical device to clamp the stomach at the second amount of compression; and wherein the second amount of compression is both greater than the first amount of compression and operably configured to immovably retain the stomach while at the predetermined positive pressure range.

26. The system of claim 25, wherein the bougie includes at least one balloon portion positioned at the distal bougie end operably configured to shape a sleeve resulting from the sleeve gastrectomy.

27. The system of claim 25, wherein the monitor comprises a visual indicator or an audible indicator, and wherein the monitor is configured to provide the indication that the predetermined positive pressure range is reached to a user via the visual indicator or the audible indicator.

* * * * *